US010231767B2

(12) United States Patent
Campbell et al.

(10) Patent No.: US 10,231,767 B2
(45) Date of Patent: Mar. 19, 2019

(54) BONE REPAIR SYSTEM, KIT AND METHOD

(71) Applicants: The Penn State Research Foundation, University Park, PA (US); Thermoplastic Products Corporation, Hummelstown, PA (US)

(72) Inventors: Christopher A. Campbell, West Chester, PA (US); Christoph A. Roth, West Chester, PA (US); Bryan Griffiths, Atglen, PA (US); Mark Grady, West Chester, PA (US); Barry M. Fell, Hummelstown, PA (US); Peter W. Dillon, Harrisburg, PA (US); Donald R. Mackay, Hershey, PA (US); Randy S. Haluck, Litiz, PA (US)

(73) Assignees: The Penn State Research Foundation, University Park, PA (US); Barry M. Fell, Hummelstown, PA (US)

( * ) Notice: Subject to any disclaimer, the term of this patent is extended or adjusted under 35 U.S.C. 154(b) by 760 days.

(21) Appl. No.: 13/835,719

(22) Filed: Mar. 15, 2013

(65) Prior Publication Data
US 2014/0277175 A1    Sep. 18, 2014

(51) Int. Cl.
*A61B 17/80* (2006.01)
*A61B 17/84* (2006.01)
(Continued)

(52) U.S. Cl.
CPC ........ *A61B 17/809* (2013.01); *A61B 17/1615* (2013.01); *A61B 17/17* (2013.01);
(Continued)

(58) Field of Classification Search
CPC ... A61B 17/809; A61B 17/8864; A61B 17/17; A61B 17/29; A61B 17/86;
(Continued)

(56) References Cited

U.S. PATENT DOCUMENTS 3,709,219 A    1/1973  Halloran
4,119,091 A   10/1978  Partridge
(Continued)

FOREIGN PATENT DOCUMENTS

CA    2361282 A1 *  3/2003  ............. A61B 19/54
CN    201617934 U    11/2010
(Continued)

OTHER PUBLICATIONS

European Patent Office, Extended European Search Report for the corresponding European Patent Application No. 10794703.8 dated Jul. 14, 2014.
(Continued)

*Primary Examiner* — Zade Coley
*Assistant Examiner* — Jessica Weiss
(74) *Attorney, Agent, or Firm* — Brooks Kushman P.C.

(57) ABSTRACT

A bone repair system, kit and method for percutaneous repair of a bone segment containing a first bone segment and a second bone segment in a patient, each bone segment having a drill hole. The system comprises a longitudinal member configured to contact the first bone segment and the second bone segment and having at least one opening and cleats on the side adapted to contact the first bone segment and the second bone segment; a first fastener assembly configured to be disposed through the opening of the longitudinal member to hold the longitudinal member in place through the opening and the hole in the first bone segment; and a second fastener assembly configured to be disposed through the opening of the longitudinal member to hold the longitudinal member in place through the opening and the hole in the second bone segment.

18 Claims, 53 Drawing Sheets

(51) Int. Cl.
*A61B 17/17* (2006.01)
*A61B 17/86* (2006.01)
*A61B 17/88* (2006.01)
*A61B 17/16* (2006.01)
*A61B 17/68* (2006.01)
*A61B 90/92* (2016.01)
*A61B 90/00* (2016.01)

(52) U.S. Cl.
CPC ........ *A61B 17/1728* (2013.01); *A61B 17/683* (2013.01); *A61B 17/808* (2013.01); *A61B 17/8042* (2013.01); *A61B 17/8052* (2013.01); *A61B 17/8076* (2013.01); *A61B 17/86* (2013.01); *A61B 17/8625* (2013.01); *A61B 17/8665* (2013.01); *A61B 17/8861* (2013.01); *A61B 17/8872* (2013.01); *A61B 17/8886* (2013.01); *A61B 17/8897* (2013.01); *A61B 90/92* (2016.02); *A61B 17/1792* (2016.11); *A61B 2017/867* (2013.01); *A61B 2090/062* (2016.02)

(58) Field of Classification Search
CPC ............ A61B 17/8042; A61B 17/8052; A61B 17/808; A61B 17/3468; A61B 17/7008; A61B 17/685
USPC ...... 606/70–71, 280–299; 411/366.1, 44, 81, 411/84–93
See application file for complete search history.

(56) References Cited

U.S. PATENT DOCUMENTS

| | | | |
|---|---|---|---|
| 4,185,624 A | 1/1980 | Gentile | |
| 4,535,764 A | 8/1985 | Ebert | |
| 4,796,612 A | 1/1989 | Reese | |
| 5,002,544 A * | 3/1991 | Klaue | A61B 17/80 606/280 |
| 5,151,103 A * | 9/1992 | Tepic | A61B 17/8052 606/280 |
| 5,167,664 A | 12/1992 | Hodorek | |
| 5,167,665 A | 12/1992 | McKinney | |
| 5,217,462 A | 6/1993 | Asnis et al. | |
| 5,250,049 A | 10/1993 | Michael | |
| 5,269,784 A * | 12/1993 | Mast | A61B 17/60 606/286 |
| 5,356,417 A | 10/1994 | Golds | |
| 5,498,265 A | 3/1996 | Asnis et al. | |
| 5,549,612 A * | 8/1996 | Yapp | A61B 17/7059 411/200 |
| 5,616,144 A * | 4/1997 | Yapp | A61B 17/7059 606/280 |
| 5,643,274 A | 7/1997 | Sander et al. | |
| 5,707,373 A * | 1/1998 | Sevrain | A61B 17/688 411/338 |
| 5,722,976 A | 3/1998 | Brown | |
| 5,989,255 A | 11/1999 | Pepper et al. | |
| 5,997,538 A | 12/1999 | Asnis et al. | |
| 6,004,327 A | 12/1999 | Asnis et al. | |
| 6,013,083 A | 1/2000 | Bennett | |
| 6,200,318 B1 * | 3/2001 | Har-Shai | A61B 17/823 140/123.6 |
| 6,302,887 B1 | 10/2001 | Spranza et al. | |
| 6,309,393 B1 * | 10/2001 | Tepic | A61B 17/80 606/280 |
| 6,368,326 B1 | 4/2002 | Dakin et al. | |
| 6,416,518 B1 | 7/2002 | DeMayo | |
| 6,514,274 B1 | 2/2003 | Boucher et al. | |
| 6,685,707 B2 | 2/2004 | Roman et al. | |
| 6,761,722 B2 | 7/2004 | Cole | |
| 6,786,909 B1 * | 9/2004 | Dransfeld | A61B 17/8052 606/280 |
| 6,902,567 B2 | 6/2005 | Del Medico | |
| 6,918,912 B2 | 7/2005 | Seemann | |
| 6,942,668 B2 | 9/2005 | Padget et al. | |
| 6,971,995 B2 | 12/2005 | Rolnick et al. | |
| 7,225,813 B2 | 6/2007 | Easter | |
| 7,255,700 B2 * | 8/2007 | Kaiser | A61F 2/0811 606/304 |
| 7,615,069 B2 * | 11/2009 | Paul | A61B 17/86 606/287 |
| 7,833,255 B2 * | 11/2010 | Chow | A61B 17/68 606/300 |
| 7,837,717 B2 | 11/2010 | Deffenbaugh et al. | |
| 8,821,580 B2 | 9/2014 | DaSilva | |
| 9,028,547 B2 | 5/2015 | Lebeau et al. | |
| 9,101,426 B2 * | 8/2015 | Forderer | A61B 17/82 |
| 2002/0077659 A1 | 6/2002 | Johnson et al. | |
| 2002/0123750 A1 | 9/2002 | Eisermann et al. | |
| 2002/0161319 A1 | 10/2002 | Matsumoto et al. | |
| 2002/0188297 A1 | 12/2002 | Dakin et al. | |
| 2002/0192051 A1 * | 12/2002 | LeVey | B21H 3/02 411/411 |
| 2003/0078585 A1 | 4/2003 | Johnson et al. | |
| 2003/0105461 A1 | 6/2003 | Putnam | |
| 2004/0116930 A1 * | 6/2004 | O'Driscoll | A61B 17/8061 606/281 |
| 2004/0147928 A1 | 7/2004 | Landry et al. | |
| 2004/0153075 A1 | 8/2004 | Roger | |
| 2005/0015088 A1 | 1/2005 | Ringeisen | |
| 2005/0043742 A1 | 2/2005 | Bruneau et al. | |
| 2005/0080421 A1 * | 4/2005 | Weaver | A61B 17/8057 606/282 |
| 2005/0085819 A1 | 4/2005 | Ellis et al. | |
| 2005/0149032 A1 | 7/2005 | Vaughen et al. | |
| 2005/0240188 A1 | 10/2005 | Chow et al. | |
| 2005/0273104 A1 | 12/2005 | Oepen et al. | |
| 2006/0004367 A1 | 1/2006 | Alamin et al. | |
| 2006/0085000 A1 | 4/2006 | Mohr et al. | |
| 2006/0167393 A1 | 7/2006 | Bolla | |
| 2006/0271198 A1 | 11/2006 | McAfee | |
| 2007/0123883 A1 | 5/2007 | Ellis et al. | |
| 2007/0213727 A1 | 9/2007 | Bottlang et al. | |
| 2007/0225715 A1 | 9/2007 | Deffenbaugh et al. | |
| 2007/0270852 A1 | 11/2007 | Tormala et al. | |
| 2007/0299448 A1 | 12/2007 | Chin et al. | |
| 2008/0027360 A1 | 1/2008 | Smith | |
| 2008/0108997 A1 * | 5/2008 | Berrevoets | A61B 17/7044 606/251 |
| 2008/0234753 A1 * | 9/2008 | Trieu | A61B 17/7022 606/297 |
| 2008/0234754 A1 | 9/2008 | McCarthy et al. | |
| 2008/0281364 A1 | 11/2008 | Chirico et al. | |
| 2009/0012571 A1 * | 1/2009 | Perrow | A61B 17/1671 606/280 |
| 2009/0048575 A1 | 2/2009 | Waters | |
| 2009/0091391 A1 | 4/2009 | Ranjan et al. | |
| 2009/0312802 A1 | 12/2009 | DaSilva | |
| 2009/0318977 A1 * | 12/2009 | Di Giacomo | A61B 17/809 606/286 |
| 2010/0004691 A1 * | 1/2010 | Amato | A61B 17/80 606/280 |
| 2010/0030276 A1 * | 2/2010 | Huebner | A61B 17/8061 606/280 |
| 2010/0036431 A1 | 2/2010 | Haidukewych | |
| 2010/0121382 A1 * | 5/2010 | Weiman | A61B 17/7059 606/264 |
| 2010/0131012 A1 * | 5/2010 | Ralph | A61B 17/80 606/280 |
| 2010/0131013 A1 * | 5/2010 | Ralph | A61B 17/80 606/286 |
| 2010/0168799 A1 | 7/2010 | Schumer | |
| 2010/0331892 A1 * | 12/2010 | Fell | A61B 17/8076 606/286 |
| 2011/0004252 A1 * | 1/2011 | Velikov | A61B 17/80 606/280 |
| 2012/0010662 A1 | 1/2012 | O'Neil et al. | |

(56) References Cited

U.S. PATENT DOCUMENTS

2014/0316471 A1 10/2014 Fell et al.
2015/0094773 A1* 4/2015 Clasbrummel .... A61B 17/8052
606/291

FOREIGN PATENT DOCUMENTS

| JP | H03500487 A | 2/1991 |
| JP | H07313522 A | 12/1995 |
| JP | H1014936 A | 1/1998 |
| JP | 2003534094 A | 11/2003 |

OTHER PUBLICATIONS

Acute Innovations, BioBridge, Resorbable Chest Wall Stabilization Plate brochure, Nov. 2010, pp. 1-3.
Acute Innovations, RibLoc, Rib Fracture Plating System, Technique Guide, Jul. 2008, pp. 1-2.
J. Hugh Devitt, MD, FRCPC, Blunt Thoracic Trauma: Assessment, Management and Anaesthesia, Winterlude 1995, pp. 1-10.
Sandra Wanek, MD et al., Blunt Thoracic Trauma: flail chest, pulmonary contusion, and blast injury, Critical Care Clinics 20 (2004) pp. 71-81.
Renata Bastos, MD et al., Flail Chest and Pulmonary Contusion, Thoracic and Cardiovascular Surgery, 2008, vol. 20, pp. 39-45.
Dr. Pradnya P. Kadam et al., Management of Chest Wall Injuries: A Comparison of Ventilatory and Non-Ventilatory Therapy, Indian J. Anaesth., 2003; 47(2), pp. 100-104.
Christine Engel, MD et al., Operative Chest Wall Fixation with Osteosynthesis Plates, The Journal of Trauma, vol. 58, pp. 181-186, 2005.
Silvana F. Marasco et al., Mode of Failure of Rib Fixation with Absorbable Plates: A Clinical and Numerical Modeling Study, Journal of Trauma, vol. 68, No. 5, May 2010, pp. 1225-1233.
Guglielmo M. Actis Dato et al., Surgical Management of Flail Chest, The Annals of Thoracic Surgery 1999, vol. 67, pp. 1826-1827.
Surgical Stabilization of Severe Flail Chest, www.iconocast.com, pp. 1-6, Jun. 14, 2005.
ClinicalTrials.gov archive, View of NCT00810251 on Dec. 17, 2008, Efficacy of MatrixRIB Implants for Surgical Stabilization of Flail Chest Injuries, pp. 1-3.
M. Mohta et al.., Experiences with Chest Trauma: Where do we stand today, Indian J. Crit. CareMed., Jan.-Mar. 2006, vol. 10(1), pp. 25-28.
PCT Search Report and Written Opinion for PCT/US2010/040596 dated Sep. 1, 2010.
International Preliminary Report on Patentability for PCT/2010/040596 dated Jan. 12, 2012.
U.S. Office Action for U.S. Appl. No. 14/252,064, dated Jun. 27, 2016, 8 pages.
Chinese Office Action and English translation for Application No. 201480015849, dated Jun. 19, 2017, 23 pages.
U.S. Office Action for U.S. Appl. No. 15/433,499, dated Sep. 10, 2018, 8 pages.

* cited by examiner

BONE REPAIR SYSTEM, KIT AND METHOD

CROSS-REFERENCE TO RELATED APPLICATIONS

This application does not claim the benefit of any other application.

TECHNICAL FIELD

This invention relates to a system, kit and method for the repair of fractured or broken bones, such as ribs.

BACKGROUND

Chest wall fractures, and in particular, fractures of rib bones of the rib cage, can cause potentially life-threatening respiratory insufficiencies, accounting for up to 50% of the mortality in thorax injuries. Fracture of a rib bone can occur at any location along the bone. Most rib fractures are treated conservatively using pain management and/or bracing techniques, but often the pain experienced by the patient during healing can be severe and last for one to two months. In addition, fractured ribs in a flail chest, a condition that occurs when a minimum of three adjacent ribs are broken, treated in such a manner may undergo progressive displacement during the healing phase, resulting in considerable deformity, volume loss, atelectasis, and chronic pain. Long-term problems of patients with flail chest injuries treated nonoperatively include subjective chest tightness, thoracic cage pain, and dyspnea.

Four categories of fixation devices for operative chest wall fixation have been utilized, namely plates, intramedullary devices, vertical bridging, and wiring. The results of these repair techniques are often less than desirable because of the difficulty in correctly locating the broken rib ends with one another. Stabilizing rib fractures is challenging because large incisions are typically needed to accommodate fixation, which leads to a more morbid procedure. In addition, ribs are narrow with a thin cortex that surrounds soft marrow, making reliable fixation problematic under conditions that include upwards of 25,000 breathing cycles per day, as well as coughing.

Currently, the surgery involves a significant operative procedure with mobilization of fractured ribs or open thoracotomy. The problems and risks of an operative approach include the surgical trauma itself and the loosening and migration of implants. The surgery involves a major incision through the muscle directly down to the ribs, which can have complications such as loss of muscle function, blood loss, and damage to surrounding vascular and neural tissue. The ribs that are to be fixed need to be adequately exposed in order to obtain a good placement of metal fixation plates. A wide incision is performed, and myocutaneous flaps may need to be raised to allow visualization of all segments. Posterior injuries are usually challenging due to the presence and required exposure of large muscle fibers (e.g., latissimus dorsi, trapezius, rhomboids, paraspinous muscles).

United States Patent Application 2010/0331892 to Fell et al, the disclosure of which is incorporated herein by reference, represents an improvement over the above-described prior art. However, the system, kit and method of the invention described in the instant specification represents a significant improvement over the teaching of Fell et al.

SUMMARY

Figure 1:
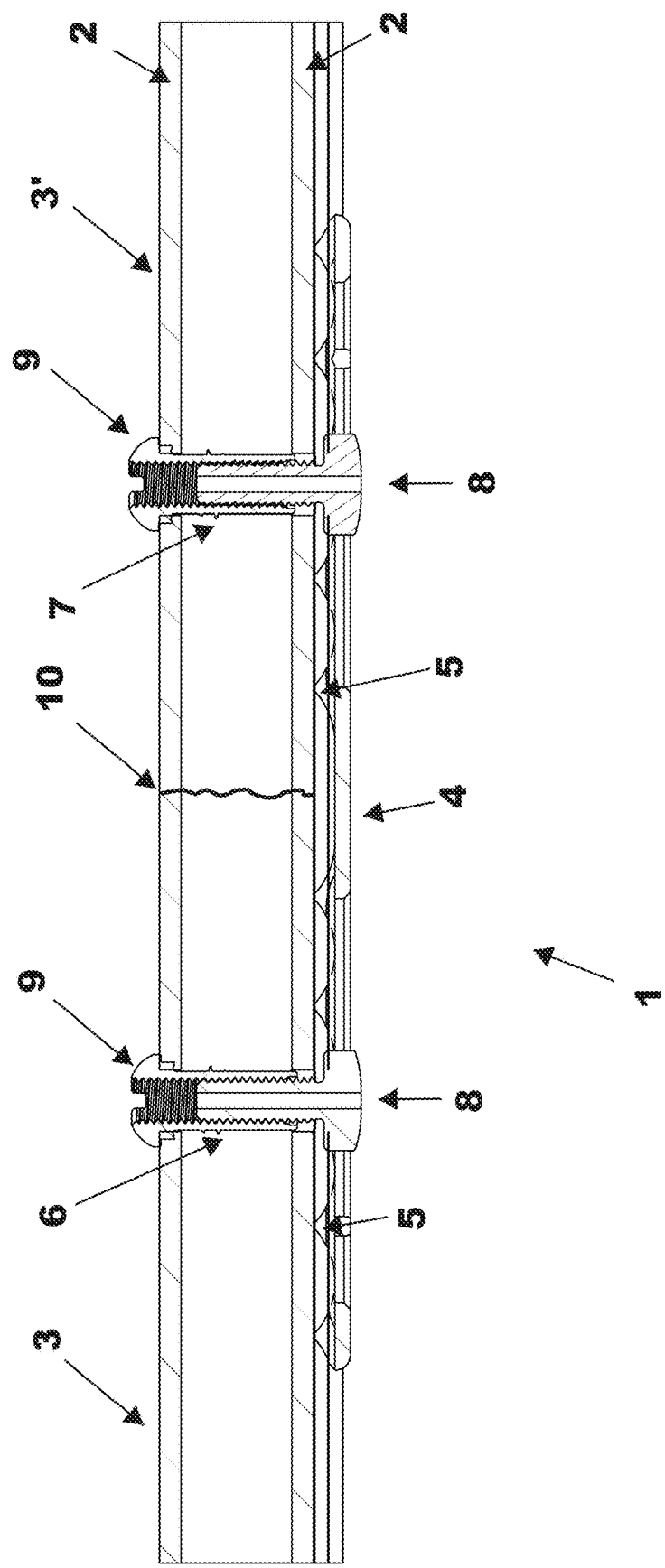
FIG. 1 is a side view of a bone repair system in accordance with an aspect of an illustrative embodiment.
Figure 2:
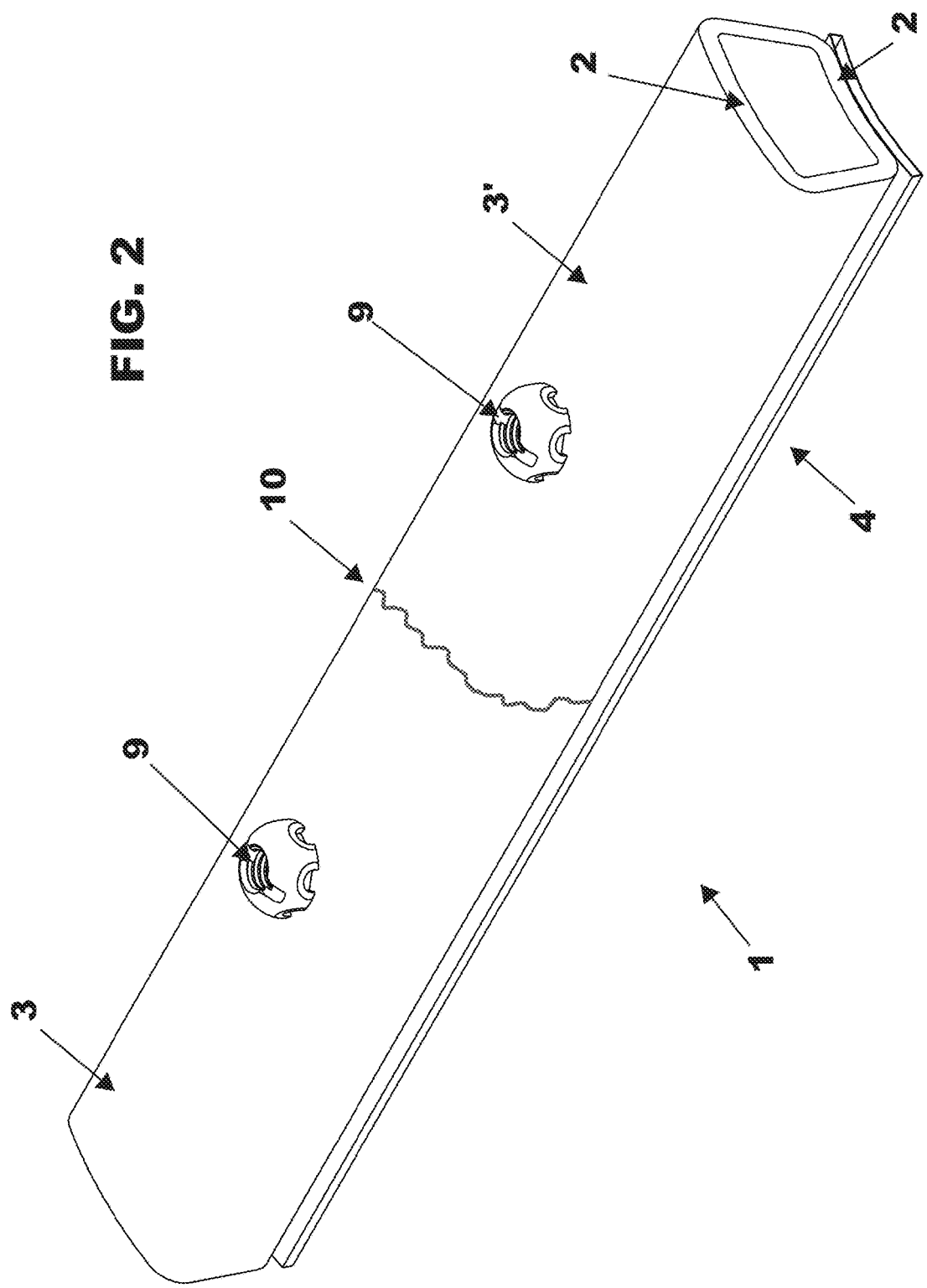
FIG. 2 is a top perspective of a bone repair system in accordance with an aspect of an illustrative embodiment.
Figure 3:
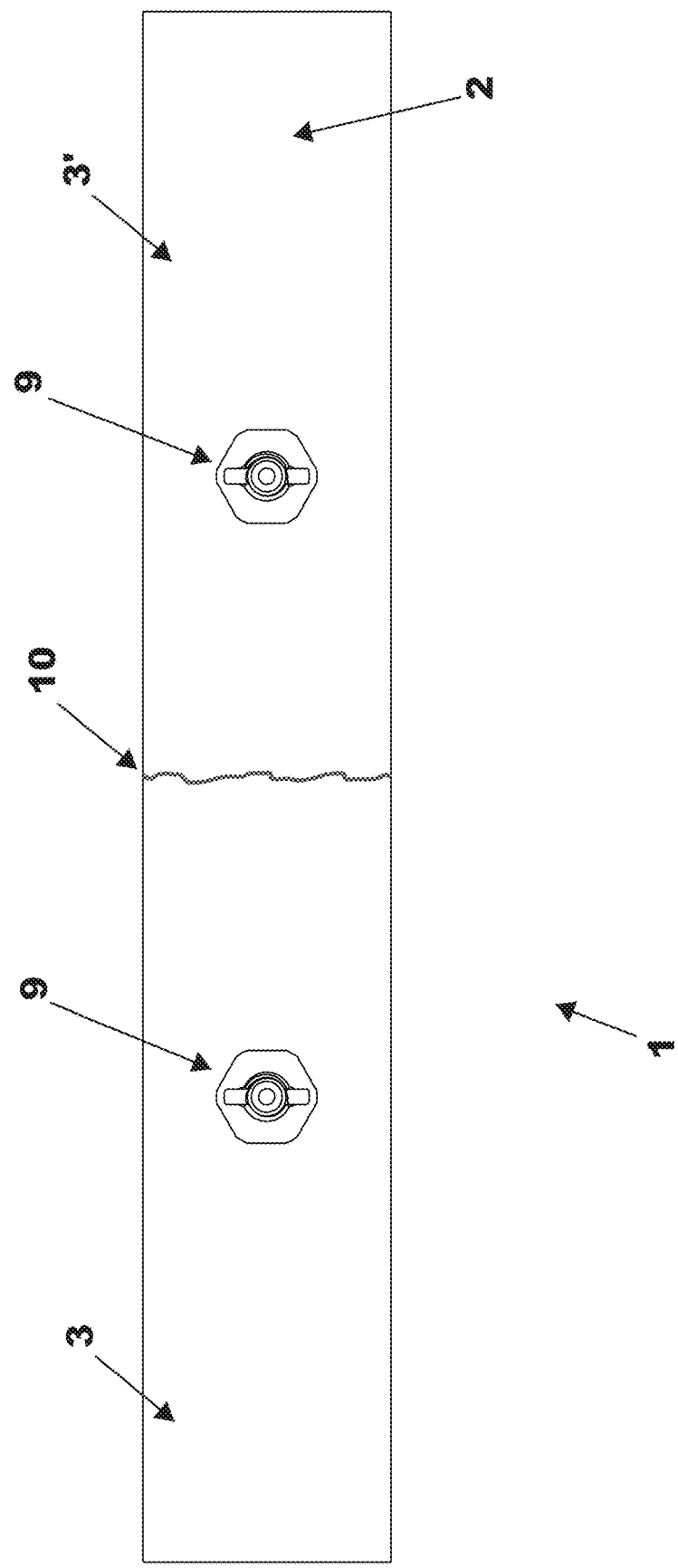
FIG. 3 is a top view of a bone repair system in accordance with an aspect of an illustrative embodiment.
Figure 4:
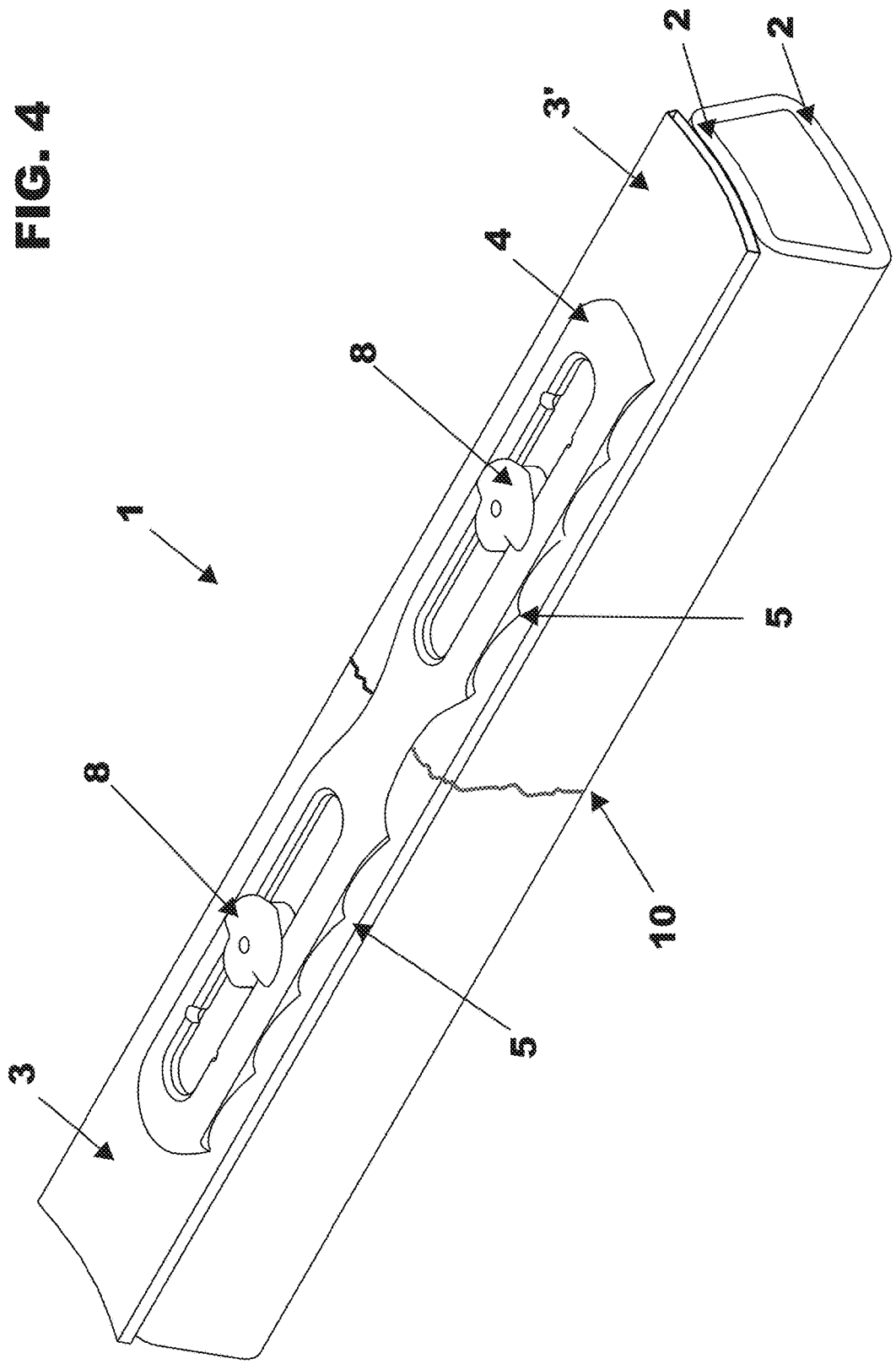
FIG. 4 is a bottom perspective view of a bone repair system in accordance with an aspect of an illustrative embodiment.
Figure 5:
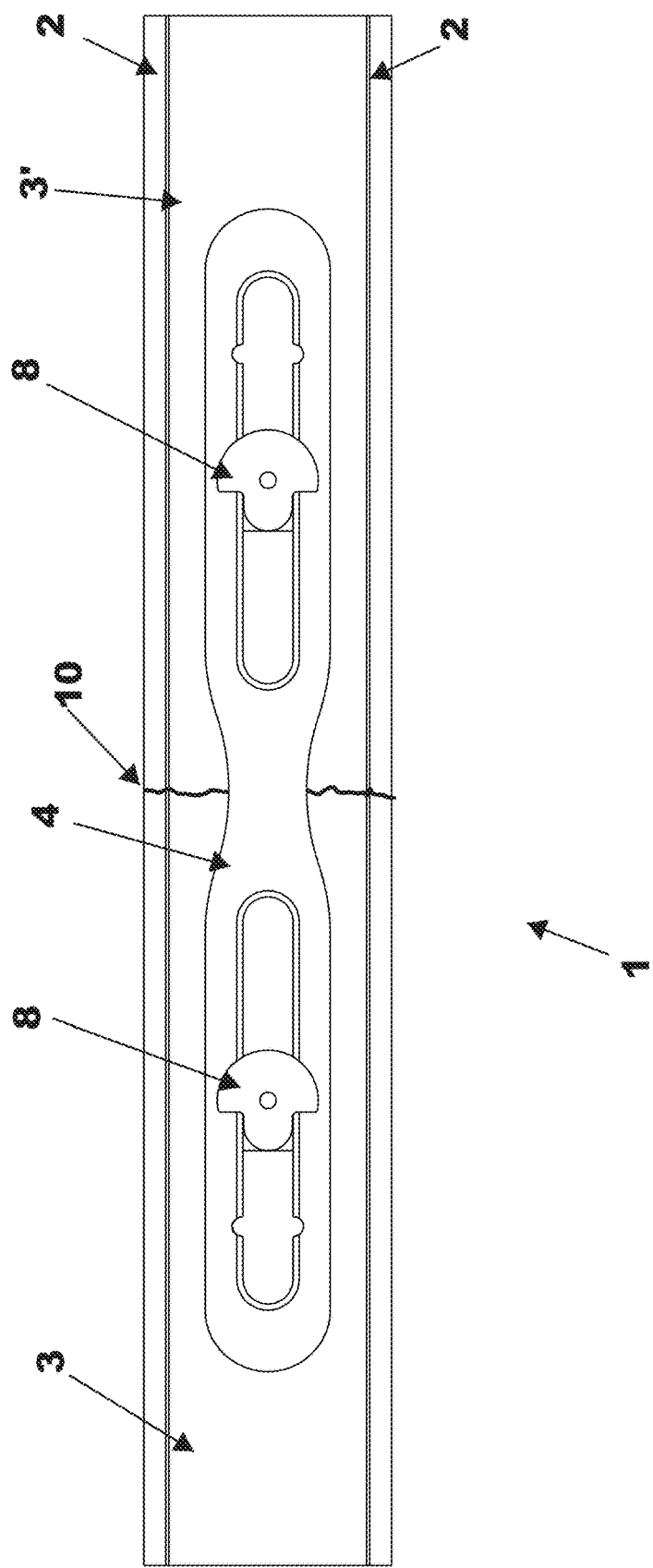
FIG. 5 is a bottom view of a bone repair system in accordance with an aspect of an illustrative embodiment.

An improved bone repair system, kit and method are described herein. In one aspect, a system for the percutaneous repair of a first bone segment and a second bone segment of a fractured bone having a drill hole in each bone segment in a patient is shown comprising: a longitudinal member configured to contact the first bone segment and the second bone segment and having at least one opening and cleats on the side adapted to contact the first bone segment and the second bone segment; a first fastener assembly configured to be disposed through the opening of the longitudinal member to hold the longitudinal member in place through the opening and the hole in the first bone segment; and a second fastener assembly configured to be disposed through the opening of the longitudinal member to hold the longitudinal member in place through the opening and the hole in the second bone segment. In a preferred embodiment, the first bone segment and the second bone segment are rib bone segments.

In another aspect, the longitudinal member contains a first opening and a second opening and the first fastener assembly is configured to be disposed through the first opening of the longitudinal member to hold the longitudinal member in place through the first opening and the hole in the first bone segment; and wherein the second fastener assembly is configured to be disposed through the second opening of the longitudinal member to hold the longitudinal member in place through the second opening and the hole in the second bone segment.

In a preferred embodiment, the hole in the first bone segment and the hole in the second bone segment are generally centered over the width of the respective bone segment.

In another preferred embodiment, the first fastener assembly includes a first inner fastener and a first outer fastener, and the second fastener assembly includes a second inner fastener and a second outer fastener. In an even more preferred embodiment, the first outer fastener and the second outer fastener are selected based upon the thickness of the first bone segment and the second bone segment respectively.

In another preferred embodiment, the longitudinal member is flexible such that the stiffness of the longitudinal member is similar to the stiffness of the bone segment to which it is attached. Use of a flexible longitudinal member promotes bone healing and avoids unintended fractures and pain to the patient. In still another preferred embodiment, the cleats on the longitudinal member are shaped so as to dig into the first bone segment and the second bone segment when the longitudinal member is contacted with the first bone segment and the second bone segment. The cleats may be of a variety of shapes including pyramidal and trapezoidal.

In a preferred embodiment, the first outer fastener is a locking cap and the second outer fastener is a locking cap. In another preferred embodiment, the first inner fastener is a pivoting locking post and the second inner fastener is a pivoting locking post, wherein the longitudinal member has slots adapted to receive the pivoting locking posts. The locking posts can pivot between a collapsed position and an extended position.

In another preferred embodiment, the first outer fastener is a locking cap shaped so as to be turnable by an external drive and the second outer fastener is a locking cap shaped so as to be turnable an external drive.

In another preferred embodiment, either the locking caps or the pivoting locking posts have lobed locking threads.

In another preferred embodiment, the locking caps have cutouts spaced around the cap so as to grip and dig into the outer cortex of a bone segment when contacted against a bone segment and wherein the cutouts are of sufficient depth to restrain the caps from being overtightened. In still another preferred embodiment, the portion of the locking caps that has cutouts is rounded in shape and has at least one external drive feature. A locking cap with between one and eight drive features is preferred. More preferably, there are four drive features. Also preferred are six drive features.

In a preferred embodiment for engaging the external drive features of the locking cap, an external drive tool is used. A preferred embodiment of the external drive tool is a self-retaining hex drive.

In another aspect, a kit for surgical repair of a fractured bone involving a first bone segment and a second bone segment is disclosed comprising: a first tether and a second tether each having a proximal end and a distal end configured to be inserted into a first guide tube and a second guide tube respectively; a longitudinal member having at least one opening configured to receive a first fastener assembly and a second fastener assembly wherein the longitudinal member is configured to be in contact with the first and second bone segments and has cleats on the side configured to be in contact with the first and second bone segments; a first fastener assembly having a longitudinal channel configured for passing the first tether therethrough and further configured to hold the longitudinal member against the first bone segment; and a second fastener assembly having a longitudinal channel configured for passing the second tether therethrough and further configured to hold the longitudinal member against the second bone segment.

In a preferred embodiment, the longitudinal member has a first opening configured to receive the first fastener assembly and a second opening configured to receive the second fastener assembly.

In a preferred embodiment, the kit further comprises a first guide tube and a second guide tube. In still another preferred embodiment, the kit further comprises an incision template.

In another preferred embodiment, the kit further comprises a positioning forceps configured to engage a bone segment and a drill guide configured to be received through the positioning forceps for facilitating drilling a hole in a bone segment.

In another preferred embodiment, the kit further comprises further comprises a drive tool having a longitudinal channel configured to pass a tether therethrough.

In another preferred embodiment, the first fastener assembly comprises an inner and outer fastener and the second fastener assembly comprises an inner and an outer fastener. In another preferred embodiment, the kit contains a plurality of outer fasteners configured to fit in bone segments of various thicknesses.

In another preferred embodiment, the first outer fastener is a locking cap and the second outer fastener is a locking cap. Also preferred is an embodiment where the first inner fastener is a pivoting locking post and the second inner fastener is a pivoting locking post, and wherein the longitudinal member has slots adapted to receive the pivoting locking posts.

In another preferred embodiment, the cleats on the longitudinal member are shaped so as to dig into the first bone segment and the second bone segment when the longitudinal member is contacted with the first bone segment and the second bone segment.

In still another preferred embodiment, the kit further comprises a removal driver.

In yet another preferred embodiment, the kit further comprises packaging containing the kit components. The kit may comprise packaging containing the longitudinal member, the first tether, the second tether, the first fastener assembly, and the second fastener assembly and wherein the longitudinal member, the first tether, the second tether, the first fastener assembly and the second fastener assembly have been sterilized.

In another aspect, a method of percutaneously fixing a first bone segment to a second bone segment in a body of a patient is disclosed comprising drilling a first hole through the first bone segment and a second hole through the second bone segment; feeding a first guide tube through the first hole and a second guide tube through the second hole, each guide tube having a proximal end and a distal end; withdrawing the first and second guide tube distal ends from the body while the first and second guide tube proximal ends have not passed through the first and second bone segments respectively; feeding a first tether through the first guide tube and a second tether through the second guide tube, each tether having a proximal end and a distal end; withdrawing the first and second tether distal ends from the body while the first and second tether proximal ends have not passed through the first and second bone segments respectively; removing the guide tubes from the body while keeping the first and second tethers in the body; passing a longitudinal member having at least one opening and cleats on the side contacting the first bone segment and the second bone segment onto the first and second tether ends; pulling the longitudinal member into engagement with the first and second bone segments guided by the tethers; and securing the longitudinal member to the first bone segment with a first fastener assembly through the first hole and the opening in the longitudinal member and to the second bone segment with a second fastener assembly through the second hole and the opening in the longitudinal member to fix the first bone segment to the second bone segment.

In another preferred embodiment, the longitudinal member comprises a first opening and a second opening, and wherein the step of passing the longitudinal member onto the first and second tether ends comprises passing the first tether end through the first opening and the second tether end through the second opening.

In a preferred embodiment of the method, the first bone segment and the second bone segment are rib bone segments.

In another preferred embodiment of the method, the method further comprises making a percutaneous incision above the first bone segment and the second bone segment. Thus, a person of ordinary skill would understand that a single incision could be used instead of two separate incisions. This includes making one incision and mobilizing soft tissue to drill a hole over a separate location. Alternatively, the method may also comprise making a first percutaneous incision above the first bone segment and a second percutaneous incision above the second bone segment wherein an incision template is used to align the location of the first and second percutaneous incisions. The incision template is an optional but advantageous feature of the method.

In still another preferred embodiment, the method comprises making a third percutaneous incision for withdrawing the distal ends of the guide tubes from the body. Instead of a percutaneous incision, the method may comprise making a port for withdrawing the distal ends of the guide tubes from the body.

In yet another preferred method, the method further comprises using a first positioning forceps containing a drill bit guide to align a drill over the first bone segment and a second positioning forceps containing a drill bit guide to align a drill over the second bone segment. It should be understood that first forceps and the second forceps may be the same. That is, a surgeon could use a forceps on one bone segment and then switch the forceps to the other bone segment.

In another preferred method, the method comprises using the first and second positioning forceps to align the drill such that each hole is generally centered over the width of the bone segment.

The method may involve preferred structures used in the above-described system. Thus, the method may involve a first fastener assembly that includes a first inner fastener and a first outer fastener, and a second fastener assembly that includes a second inner fastener and a second outer fastener. In a preferred embodiment, the method comprises the step of selecting the first outer fastener and the second outer fastener based upon the thickness of the first bone segment and the second bone segment respectively.

In another preferred embodiment of the method, the first outer fastener is a locking cap and the second outer fastener is a locking cap. In yet another preferred embodiment of the method, the first inner fastener is a pivoting locking post and the second inner fastener is a pivoting locking post, wherein the longitudinal member has slots adapted to receive the pivoting locking posts.

In another preferred embodiment, the method further comprises the step of pulling the longitudinal member into the body towards the first and second bone segments wherein the pivoting locking posts are collapsed into the reinforcing member as the reinforcing member moves through the body towards the first and second bone segments.

In another preferred embodiment, the first outer fastener is a locking cap shaped so as to be turnable by an external drive and the second outer faster is a locking cap shaped so as to be turnable by an external drive. In still another preferred embodiment, the method further comprises the step of tightening the first and second outer fasteners with an external drive wherein the external drive has a longitudinal channel for passing a tether therethrough.

In yet another preferred embodiment of the method, either the locking caps or the pivoting lock posts have lobed locking threads. In another preferred embodiment, the method further comprises the step of locking the locking cap and the pivoting locking post via the lobed locking threads.

In another preferred embodiment of the method, the locking cap has cutouts spaced around the cap so as to grip and dig into the outer cortex of a bone segment and wherein the cutouts are of sufficient depth to resist the cap from being overtightened.

In another preferred embodiment of the method, the longitudinal member has been preassembled such that first and second tethers pass therethrough prior to feeding the first and second tethers into the guide tubes. Thus, it should be understood by those of skill in the art that this would encompass pre-assembly of the longitudinal member/tether combination by a manufacturer so that a surgeon need not prepare the assembly prior to or during surgery. However, it would also encompass pre-assembly by the surgeon or other healthcare facility staff.

In another preferred embodiment of the method, the method further comprises tightening the first fastener assembly and the second fastener assembly so that the cleats on the longitudinal member dig into the first bone segment and the second bone segment.

DETAILED DESCRIPTION OF ILLUSTRATIVE EMBODIMENTS

As required, detailed illustrative embodiments are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the illustrative embodiments disclosed herein.

Disclosed herein is a system, kit and method for repairing fractured or broken bones, such as ribs. The system, kit and method according to the present invention allow bone repair to be performed in a minimally invasive manner, thereby lessening patient recovery time. Although the system, kit and method are shown and described herein as being applied to the repair of fractured ribs, it is understood that their application to the repair of other broken bones is fully contemplated. For example, the system and method according to the present invention may also be utilized for the minimally invasive repair of bone segments such as a fractured clavicle, fractured tibia, fractured pelvis, fractured spine, or fractured joint surface where there are displaced and/or multiple bone fragments that would otherwise require a large open surgical exposure to repair.

In overview, in accordance with an aspect of the illustrative embodiments, fixation of bone segments such as fractured ribs includes the placement of tethered repair components through a percutaneous skin incision down to the bone and delivery of repair components into the pleural space. Assistance may be provided by a video-thorascope, imaging technologies, or other minimally invasive observation method. The tethered repair components include a longitudinal member with cleats on the side configured to contact the bone, such as a bone plate, and a fastener assembly, such as a locking cap and pivoting locking post or other compressive fastener assembly, wherein the broken rib segment is stabilized by securing the longitudinal member against the rib with the fastener assembly. The longitudinal member may be attached to the rib on its internal surface, the side of the rib lining the pleural space. The tether, such as a cable, cord, or rod, serves to facilitate the procedure by guiding and providing control over the repair components, and to provide safety and efficiency for the surgeon.

The use of such a system of rib fixation according to the one aspect of an illustrative embodiment allows for the passage of fastener hardware through the central, thickest portion of the rib, thus reducing the risk of inadvertent damage to the peripheral neurovascular anatomy. Further, the rib is a very small bone that typically has only a thin cortical shell or, in some cases, is comprised of largely cartilaginous material. Thus, a traditional repair utilizing typical bone screws has a chance of the screw loosening over time.

A rib fracture repair can be performed in accordance with an aspect of an illustrative embodiment utilizing one or more small percutaneous incisions. One or more incisions may be utilized to percutaneously locate and drill holes for the passage of fasteners which allow for simultaneous capture and engagement with both inner and outer portions of the rib and mechanical interlock with the longitudinal member. Another incision or port allows for the percutaneous insertion of fasteners and reinforcing members to be placed against the rib via the pleural space. A still further incision or port may be utilized to allow for thorascopic visualization of the fracture site. In the drawings provided herein, although not shown, it is understood that the patient's skin overlies the ribs and the above-described incisions are made therethrough.

With reference to FIGS. 1 to 5, a system for bone repair 1 in accordance with an aspect of the present invention is shown. System 1 contacts a first bone segment 3 in rib 2 to a second bone segment 3' in rib 2. The bone 2 has a fracture 10. System 1 contacts the bone segments 3, 3' in rib 2 using longitudinal member 4. Longitudinal member 4 can take a variety of shapes and has cleats 5 on the side of the member contacting the bone. Longitudinal member 4 is held in place by first fastener assembly 6 and second fastener assembly 7. The first and second fastener assemblies preferably comprise an inner fastener 8 and an outer fastener 9. In a preferred embodiment, inner fastener 8 is a pivoting locking post and outer fastener 9 is a locking cap. It should be understood that the fasteners could be reversed so that the outer fastener would be switched with the inner fastener and vice versa.

Figure 6:
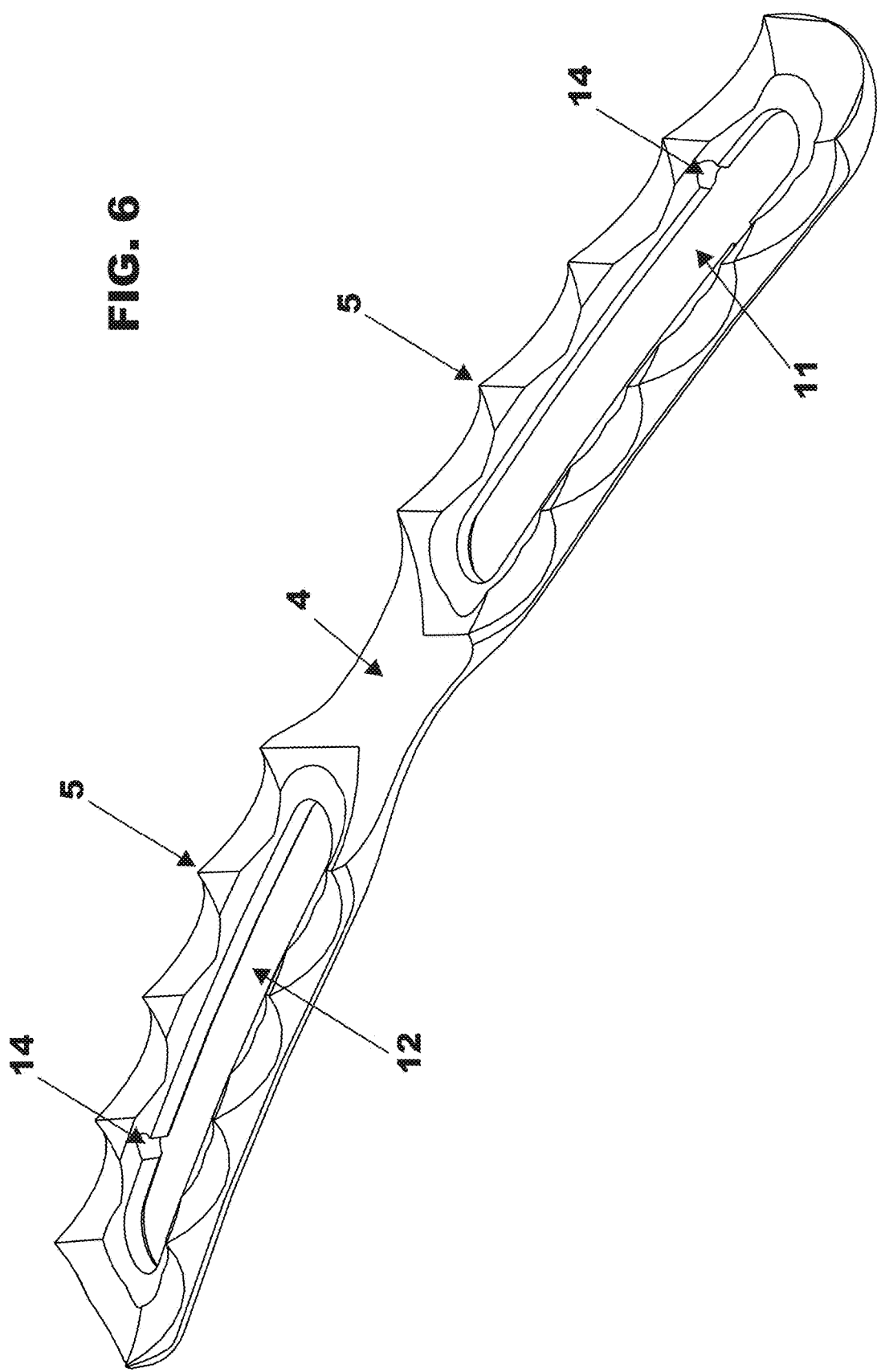
FIG. 6 is a top perspective view of a longitudinal member in accordance with an aspect of an illustrative embodiment.
Figure 7:
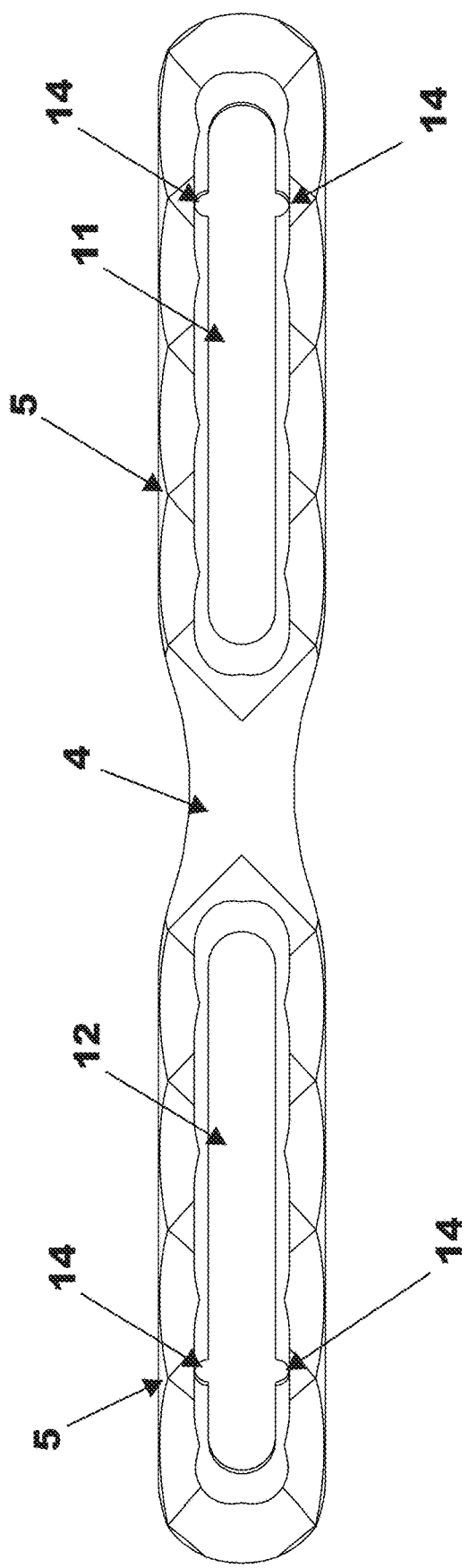
FIG. 7 is a top view of a longitudinal member in accordance with an aspect of an illustrative embodiment.
Figure 8:
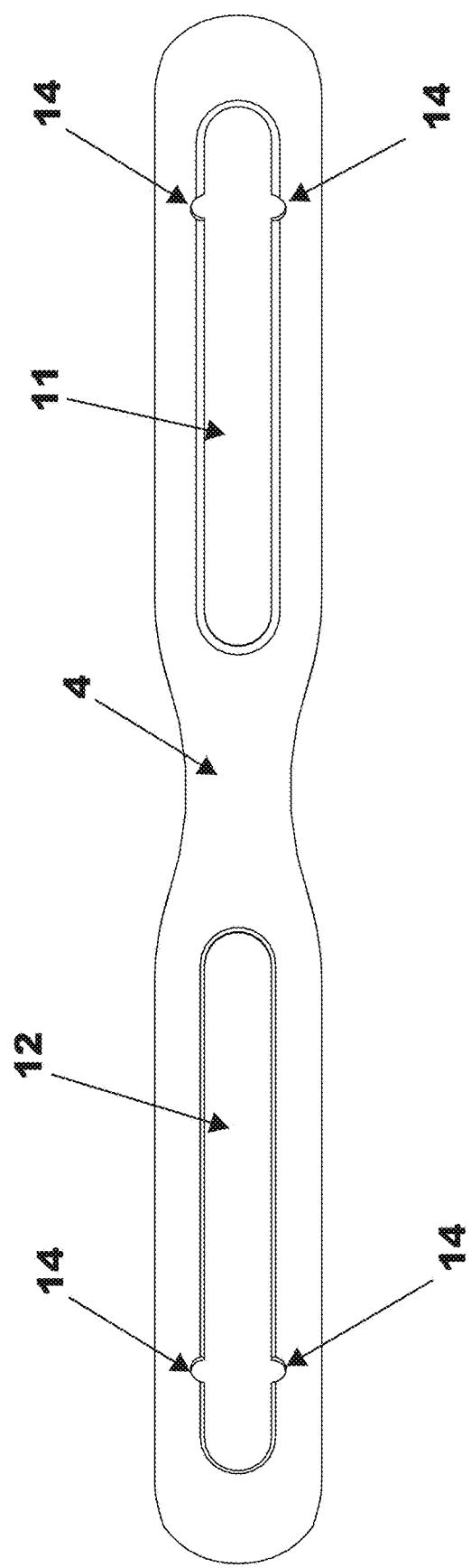
FIG. 8 is a bottom view of a longitudinal member in accordance with an aspect of an illustrative embodiment.
Figure 9:
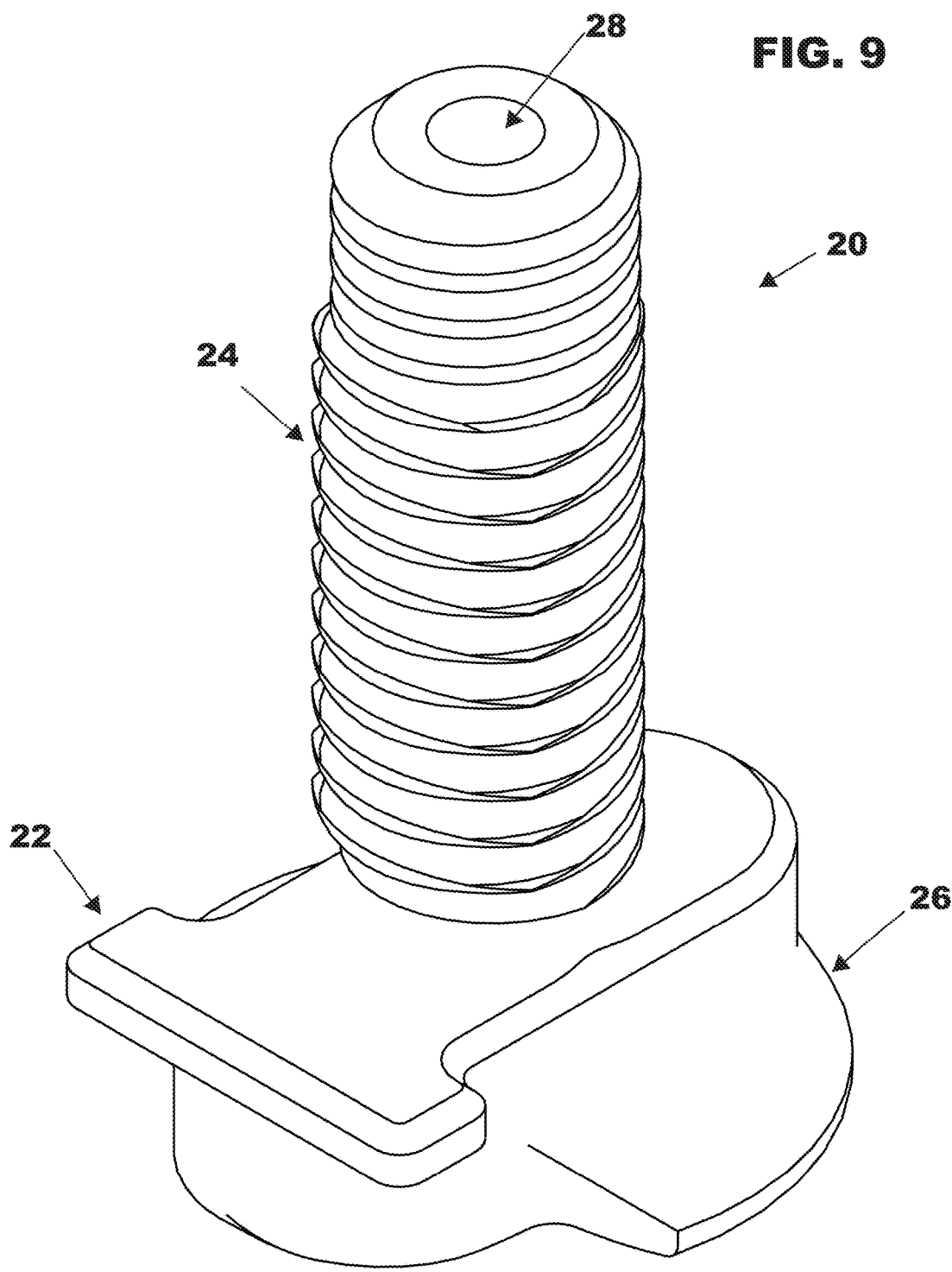
FIG. 9 is a perspective view of a pivoting locking post in accordance with an aspect of an illustrative embodiment.
Figure 10:
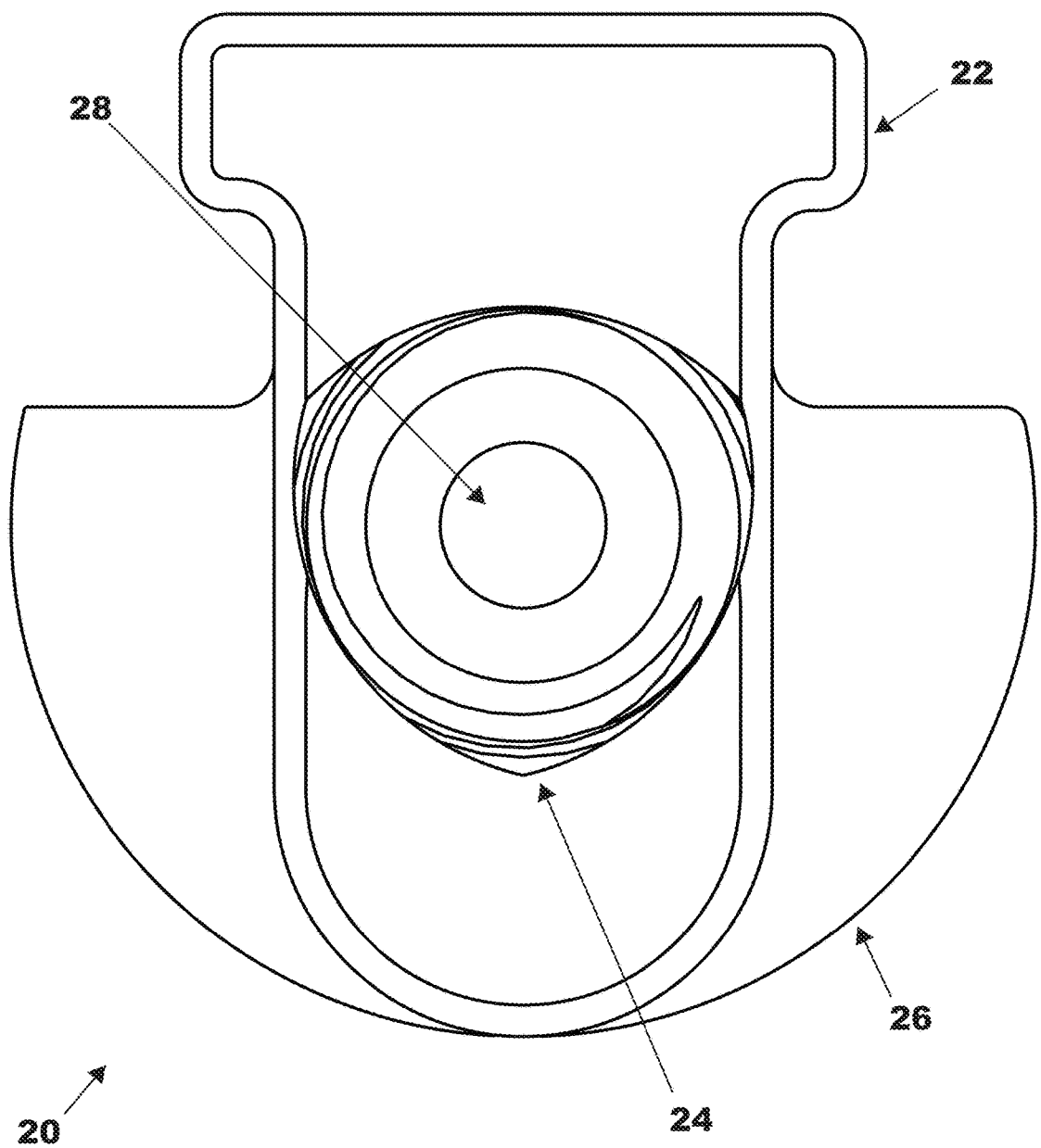
FIG. 10 is a bottom view of a pivoting locking post in accordance with an aspect of an illustrative embodiment.
Figure 11:
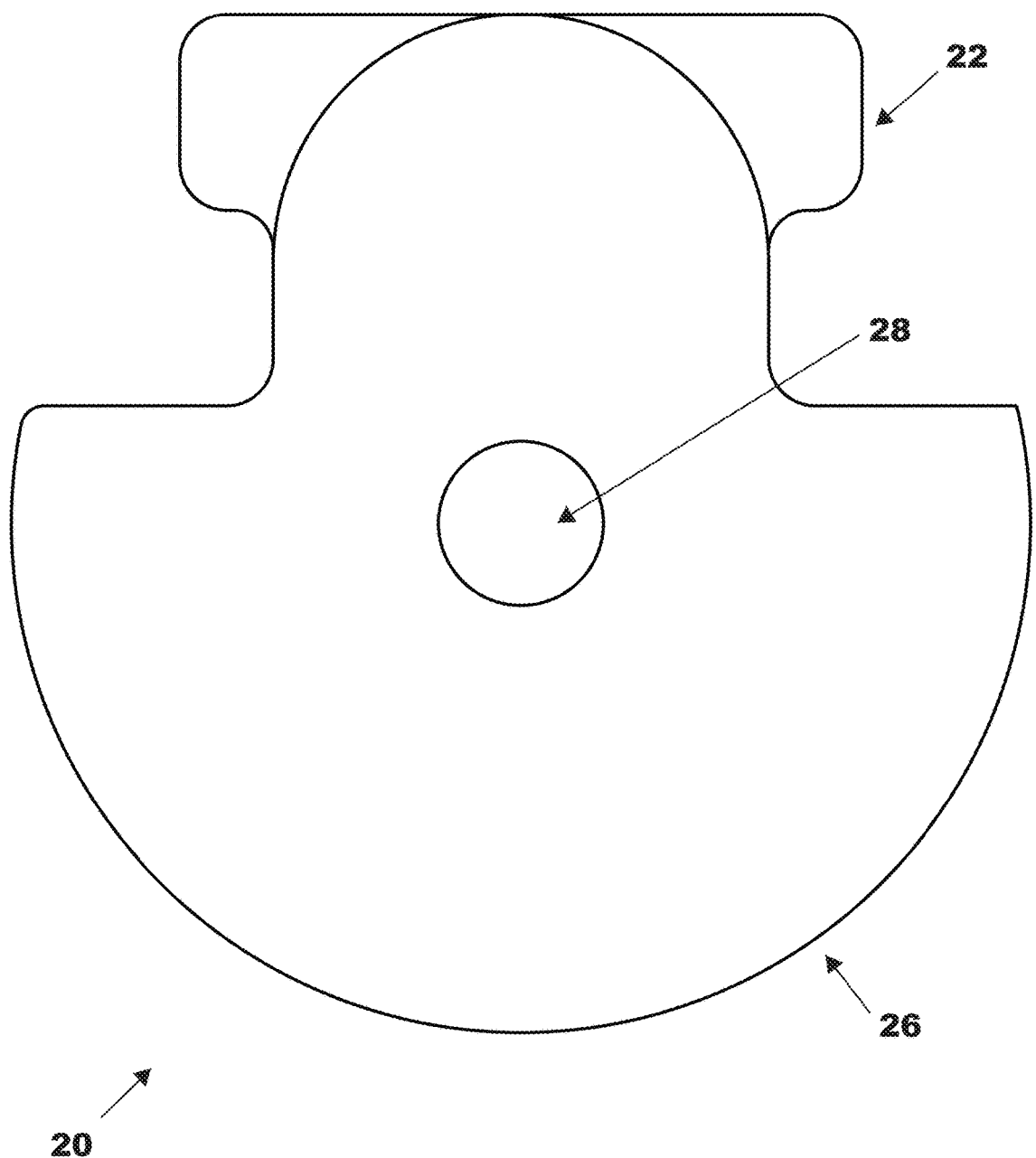
FIG. 11 is a top view of a pivoting locking post in accordance with an aspect of an illustrative embodiment.
Figure 12:
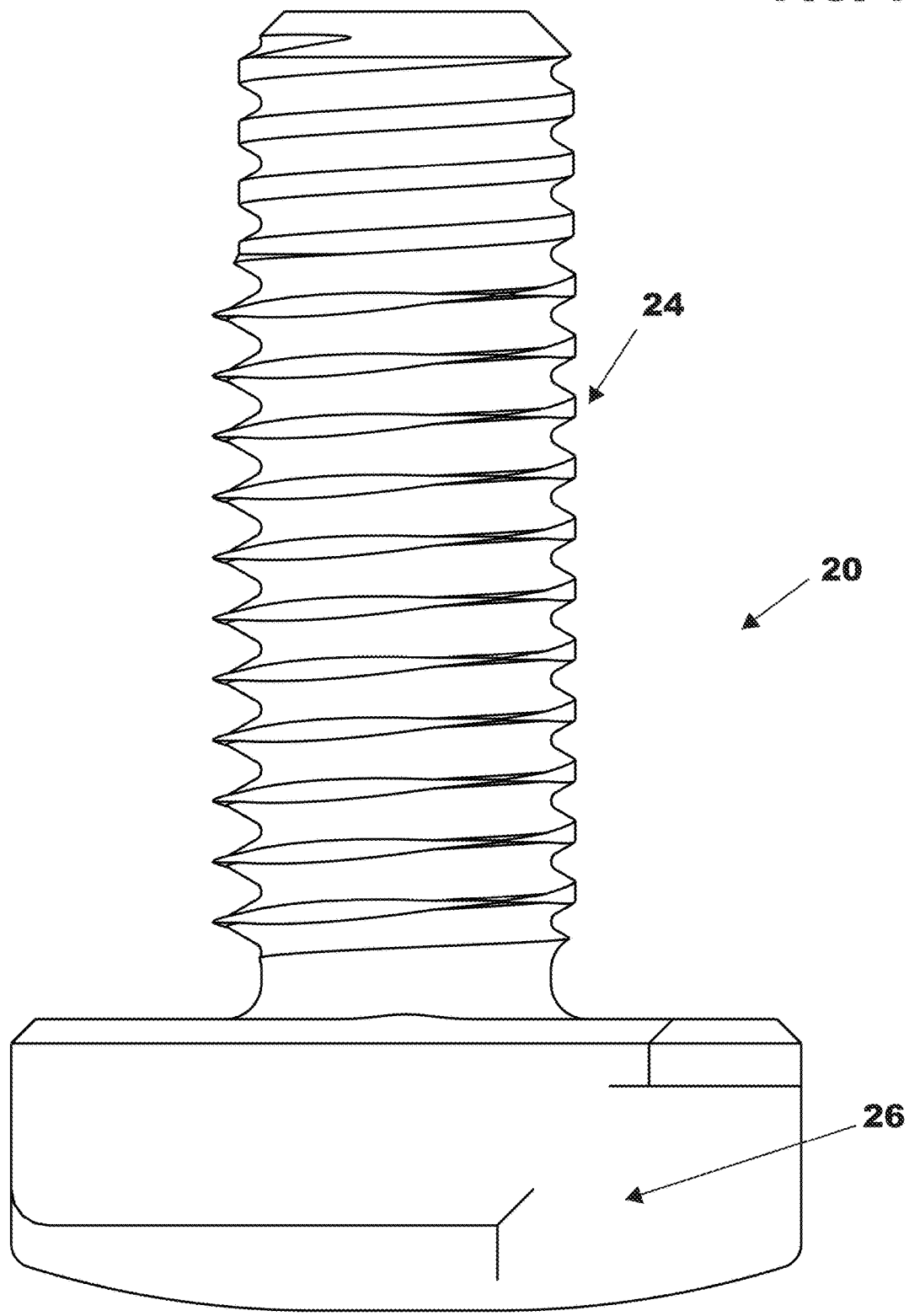
FIG. 12 is a side view of a pivoting locking post in accordance with an aspect of an illustrative embodiment.
Figure 13:
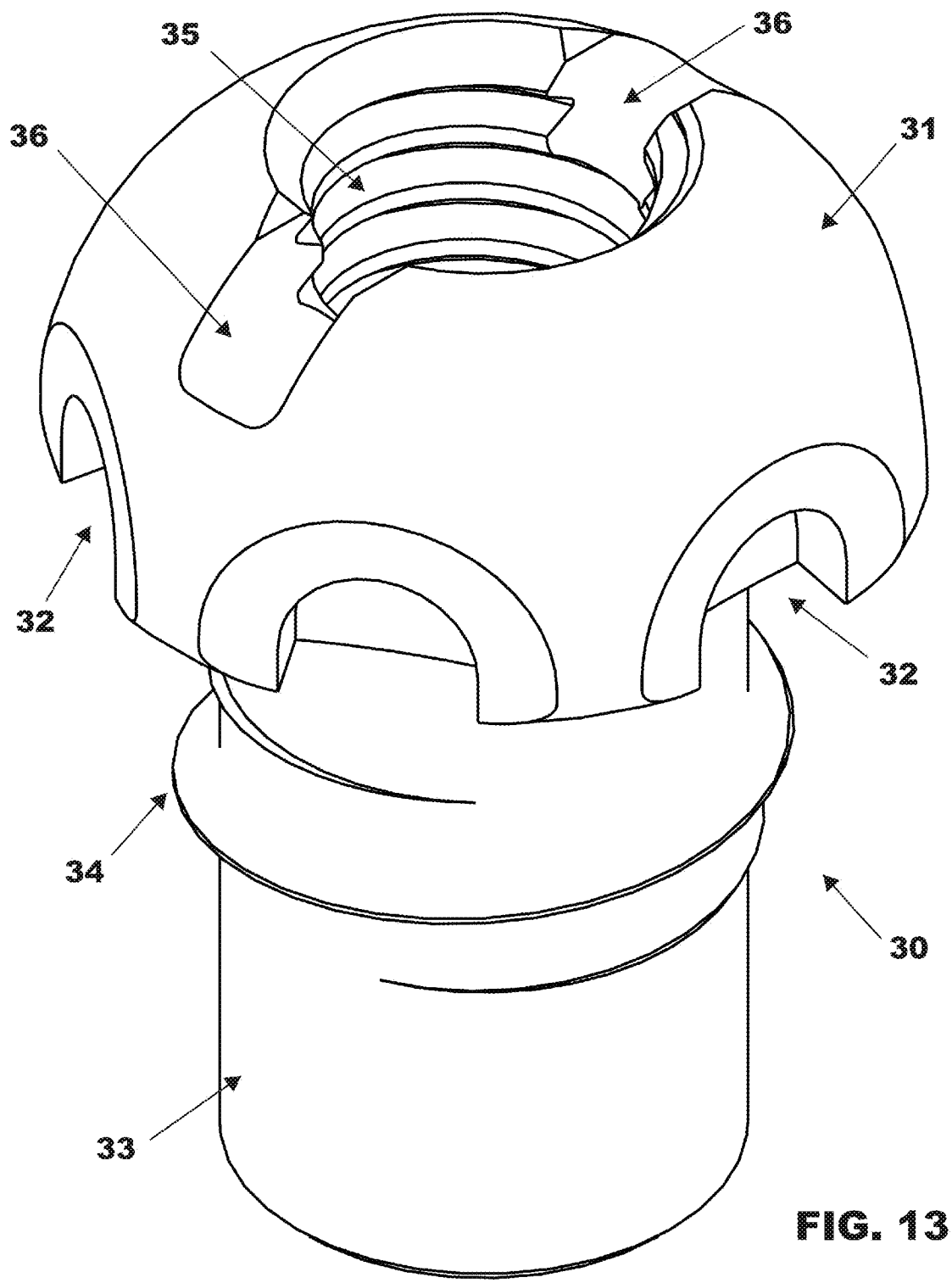
FIG. 13 is a perspective view of a locking cap in accordance with an aspect of an illustrative embodiment.
Figure 14:
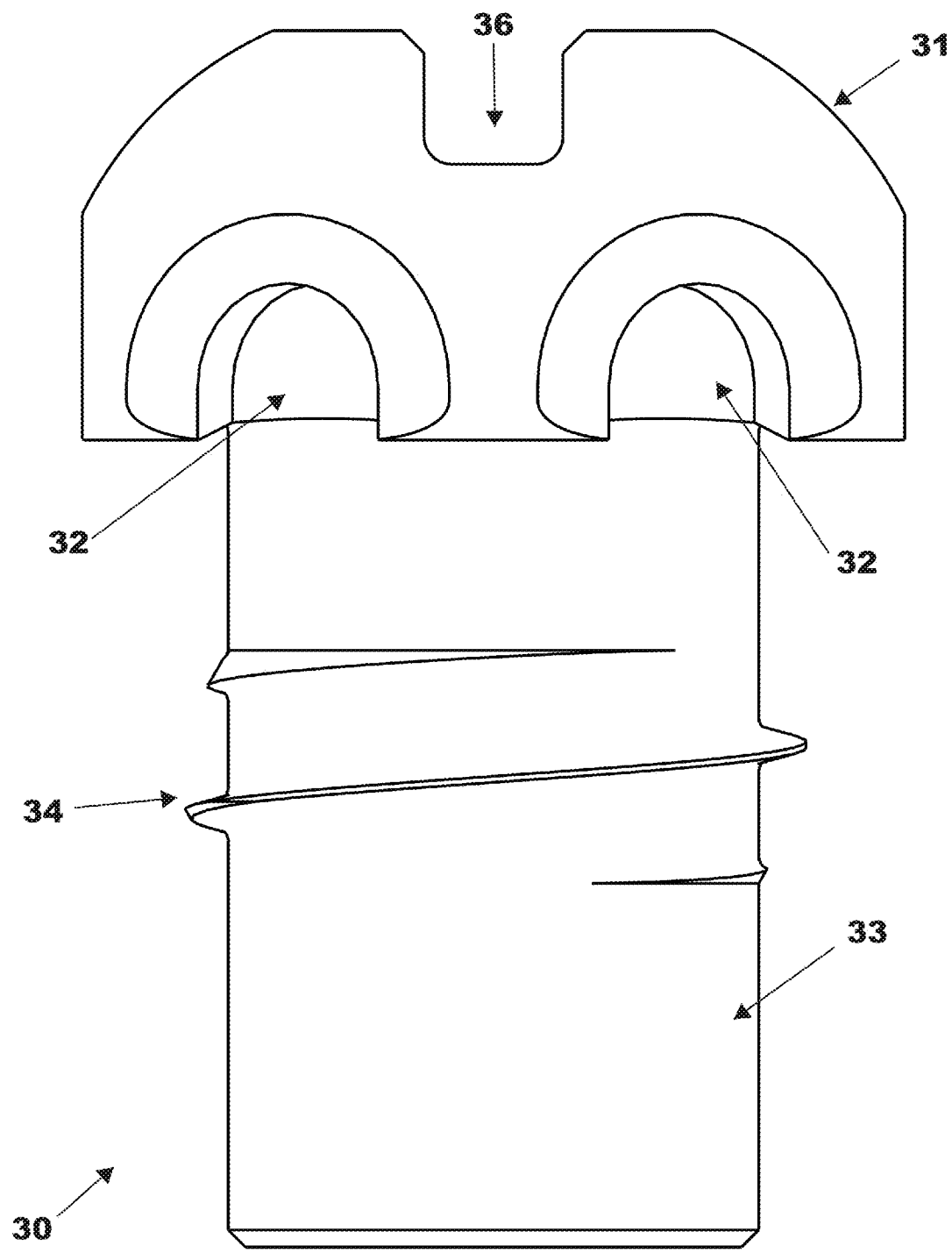
FIG. 14 is a side view of a locking cap in accordance with an aspect of an illustrative embodiment.

Turning to FIGS. 6 to 8, an exemplary longitudinal member 4 is shown in more detail. Longitudinal member 4 is configured to be contacted with bone segments in a broken bone (not shown). Longitudinal member 4 has cleats 5 on the side configured to be contacted with the bone segments. Longitudinal member 4 further comprises a first opening 11 and a second opening 12 for passing first and second inner fasteners (not shown) through to hold longitudinal member 4 against the bone segments. In a preferred embodiment, longitudinal member 4 has slots 14 in openings 11 and 12 to permit insertion of a pivoting locking post (not shown).

Cleats 5 preferably are shaped to distribute stress on longitudinal member 4, for example, by use of a curved portion between cleats. The cleats 5 dissect through the soft tissue surrounding the rib and provide purchase into the inner part of the rib. Preferably, the cleats 5 provide a distributed monocortical fixation of fractured bone which assists to resist rotation of bone segments 3, 3' relative to each other. Cleats 5 preferably have a height range from 0.1 mm to 10 mm, more preferred is 1.5 mm. The cleats 5 need not be sharp. For example, a rounded shape such as a cone may be used. Alternatively, the cleats 5 may be shaped in the form of pins, spikes, pyramids, ridges, trapezoids, or any other suitable shape. The cleats 5 are preferably made of the same material as the longitudinal member 4 described below.

The longitudinal member 4 may be constructed from an appropriate material such as, but not limited to, titanium, stainless steel, polymer, ceramic or a bio-resorbable material or combinations thereof. For the type of repair described herein, according to one non-limiting aspect of an illustrative embodiment, the longitudinal member 4 may be approximately 4-12 mm in width, or more particularly 8 mm in width. The length of the longitudinal member 4 is as needed, but according to one non-limiting aspect of the present invention may range from 30 mm to 300 mm. The thickness of the longitudinal member 4 (not counting cleats 5) can be uniform or variable, such as providing greater thickness near the middle of the longitudinal member to enhance stiffness or to tailor the stiffness to a specific level, such as to match the particular section of the rib bone. According to one non-limiting aspect of an illustrative embodiment, the longitudinal member 4 thickness (not including the cleats) may range from 0.2 mm to 5 mm. The longitudinal member 4 may be generally planar, or may instead be curved.

Turning to FIGS. 9 to 12, a pivoting locking post 20 is shown. The pivoting locking post 20 is comprised of a lobed threaded shaft 24 with an insertion tab 22 and a head flange 26 with a center cannulation 28 running along the center axis. Pivoting locking post 20 has an insertion tab 22 for inserting locking post 20 into the slots 14 in longitudinal member 4. See FIGS. 6 to 8. Pivoting lock post 20 preferably further comprises a lobed threaded shaft 24 for holding the locking tab to an outer fastener (not shown) which is preferably a locking cap. In a standard threading system, the threads are put on round surfaces. In contrast, in a lobed locking system, the threads are put on a lobed surface where the peaks of the lobe act as cutting edges. The cutting edges cut into the mated fastener to retard loosening of the two fasteners. The pivoting locking post 20 may be made of any suitable material including implantable-grade stainless steel or commercially pure titanium or a titanium alloy.

Turning to FIGS. 13 to 16, a locking cap 30 is shown. Locking cap 30 has a generally round top portion 31 containing multiple cut-outs 32 spaced around the top portion 31. The rounded portion is attached to shaft 33. Shaft 33 may optionally have a cortex ridge 34 around shaft 33 for holding the locking cap in a bone segment. Rounded top portion 31 and shaft 33 have a threaded cannulation 35 running along the center axis. Rounded top portion 31 also contains removal slot 36 running across rounded top portion 31. The threaded cannulation 35 in locking cap 30 holds locking cap 30 to an inner fastener (not shown) which is preferably a pivoting locking post. The locking cap 30 may be made of any suitable material including implantable-grade stainless steel or commercially pure titanium or a titanium alloy.

Figure 15:
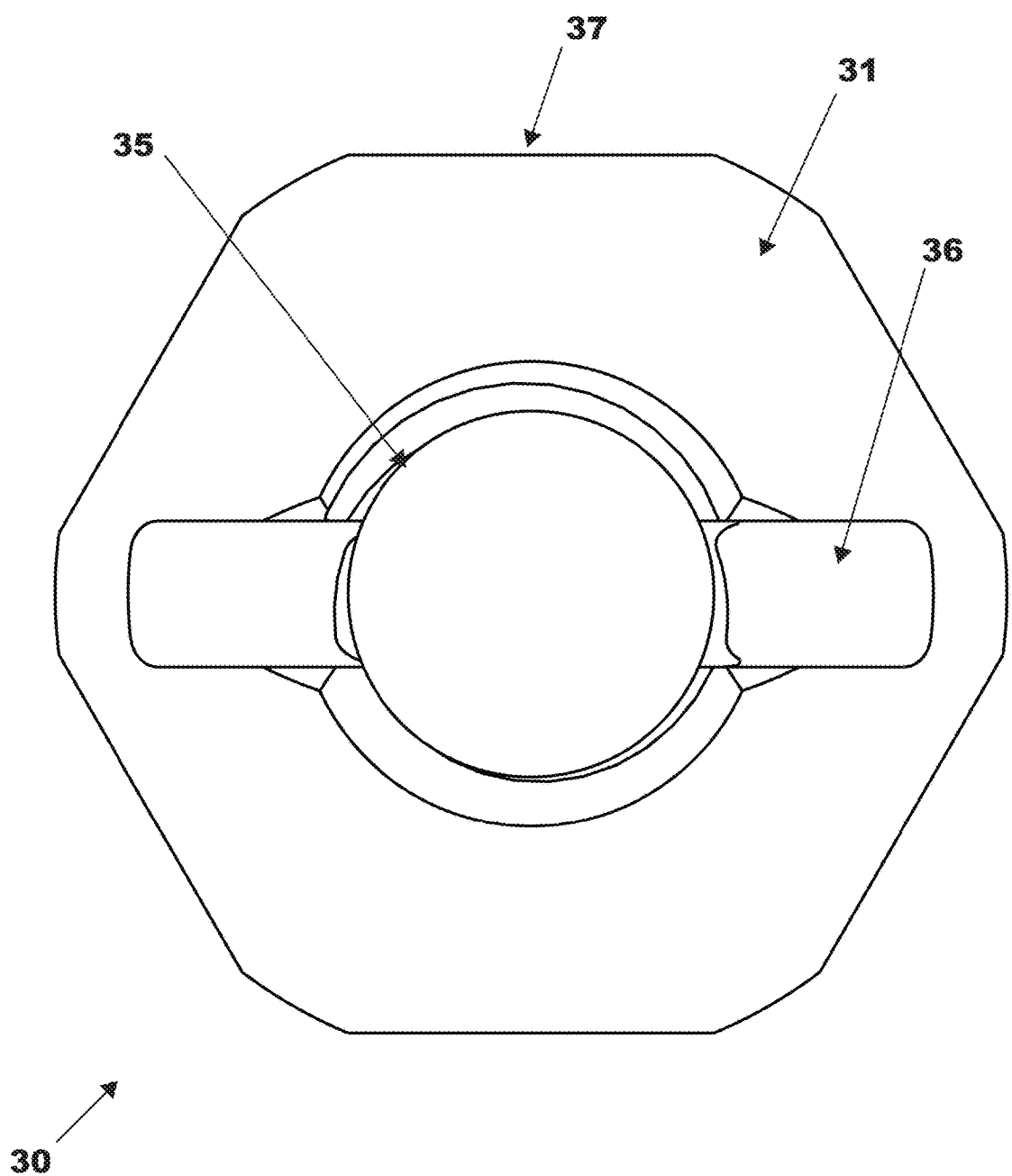
FIG. 15 is a top view of a locking cap in accordance with an aspect of an illustrative embodiment.
Figure 16:
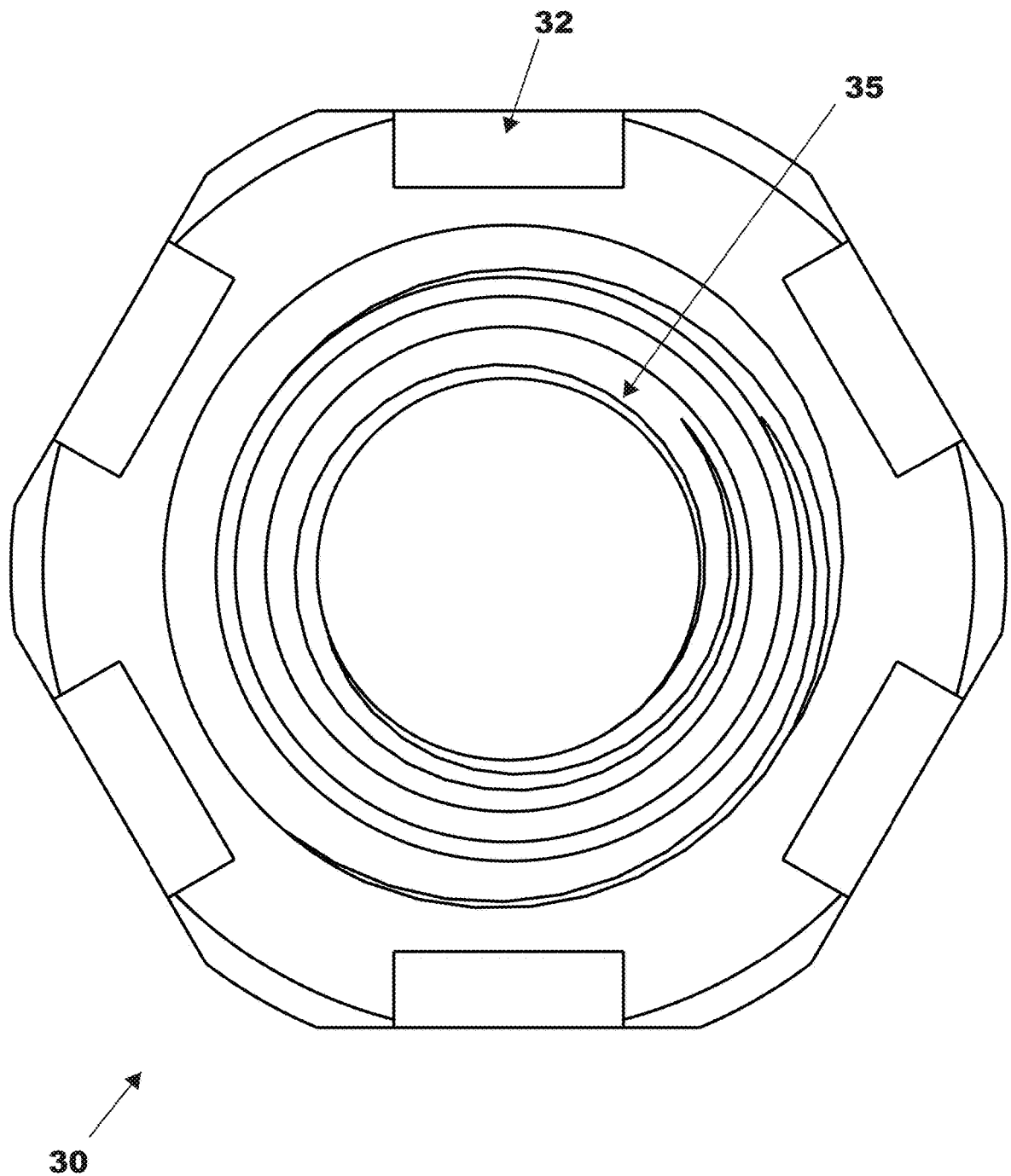
FIG. 16 is a bottom view of a locking cap in accordance with an aspect of an illustrative embodiment.
Figure 17:
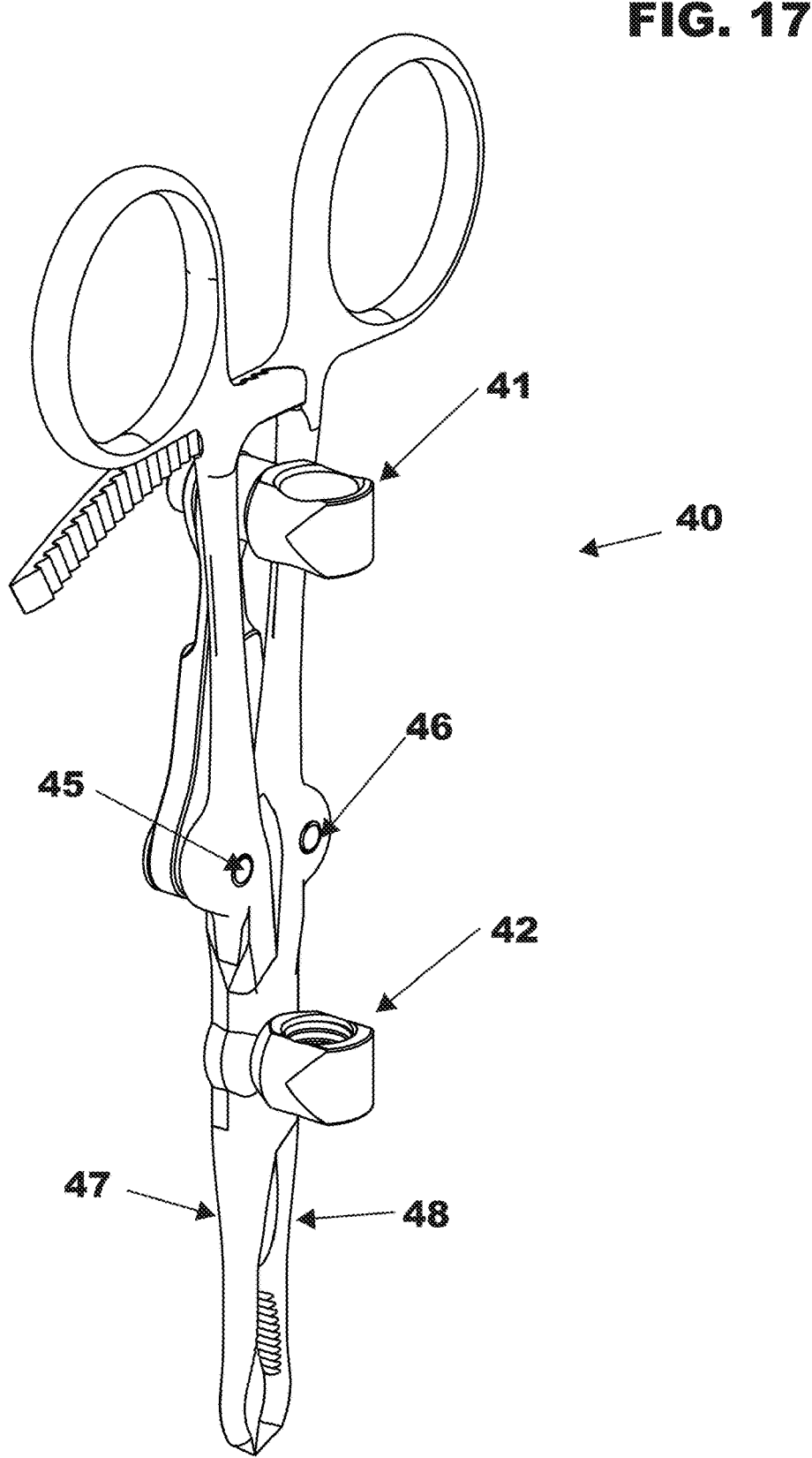
FIG. 17 is a perspective view of a positioning forceps in accordance with an aspect of an illustrative embodiment.
Figure 18:
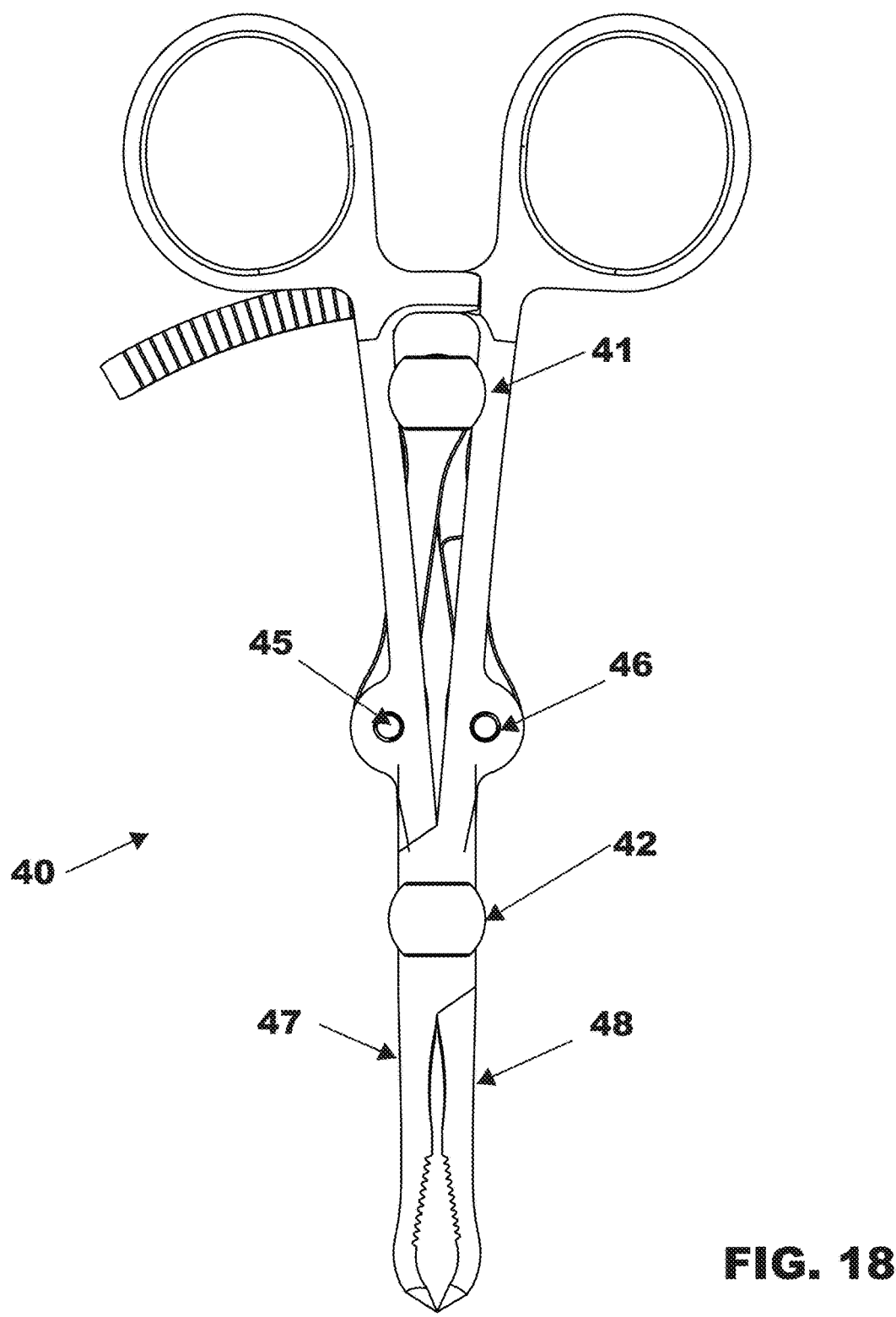
FIG. 18 is a front view of a positioning forceps in accordance with an aspect of an illustrative embodiment.
Figure 19:
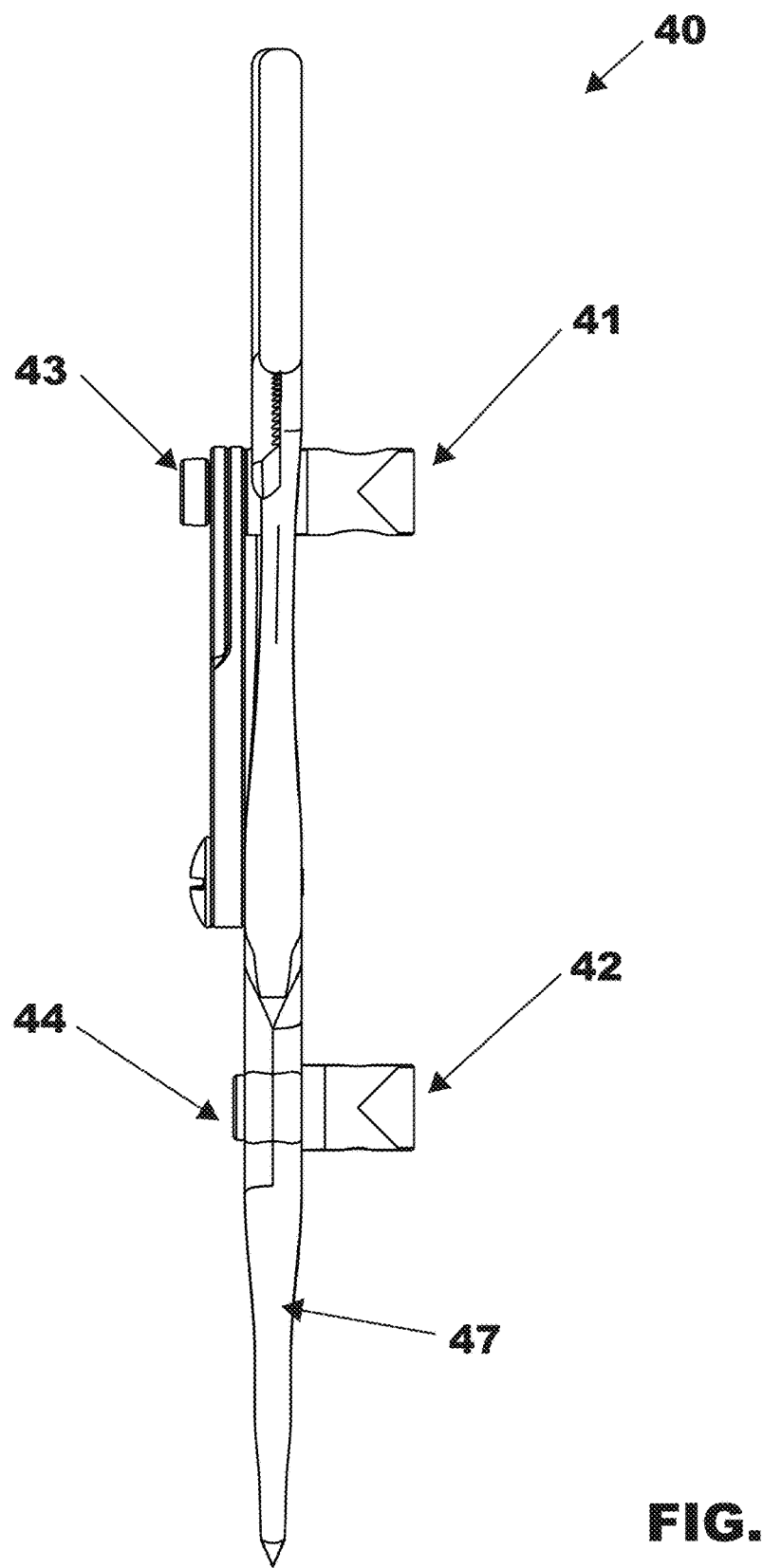
FIG. 19 is a side view of a positioning forceps in accordance with an aspect of an illustrative embodiment.
Figure 20:
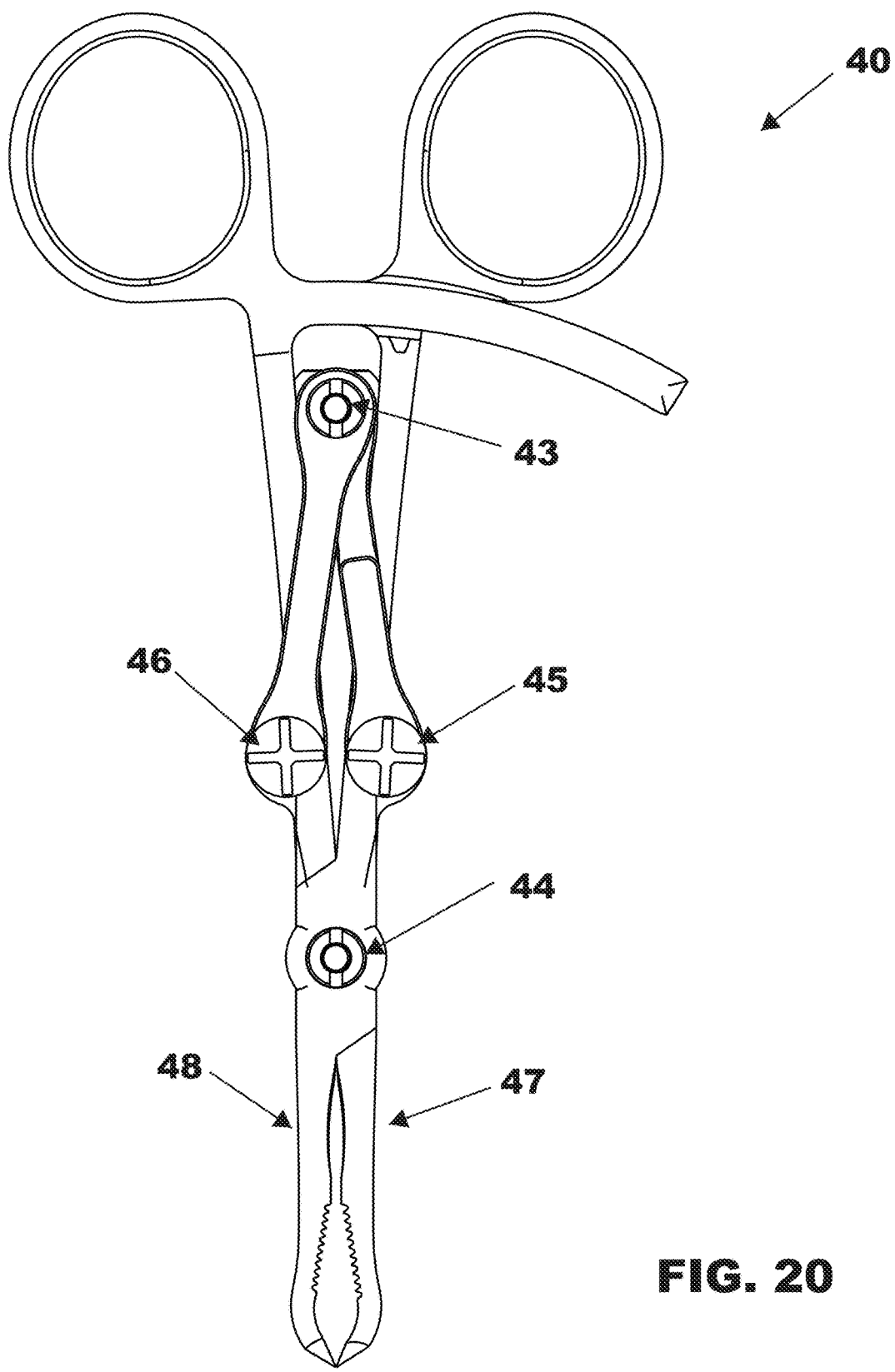
FIG. 20 is a rear view of a positioning forceps in accordance with an aspect of an illustrative embodiment.
Figure 21:
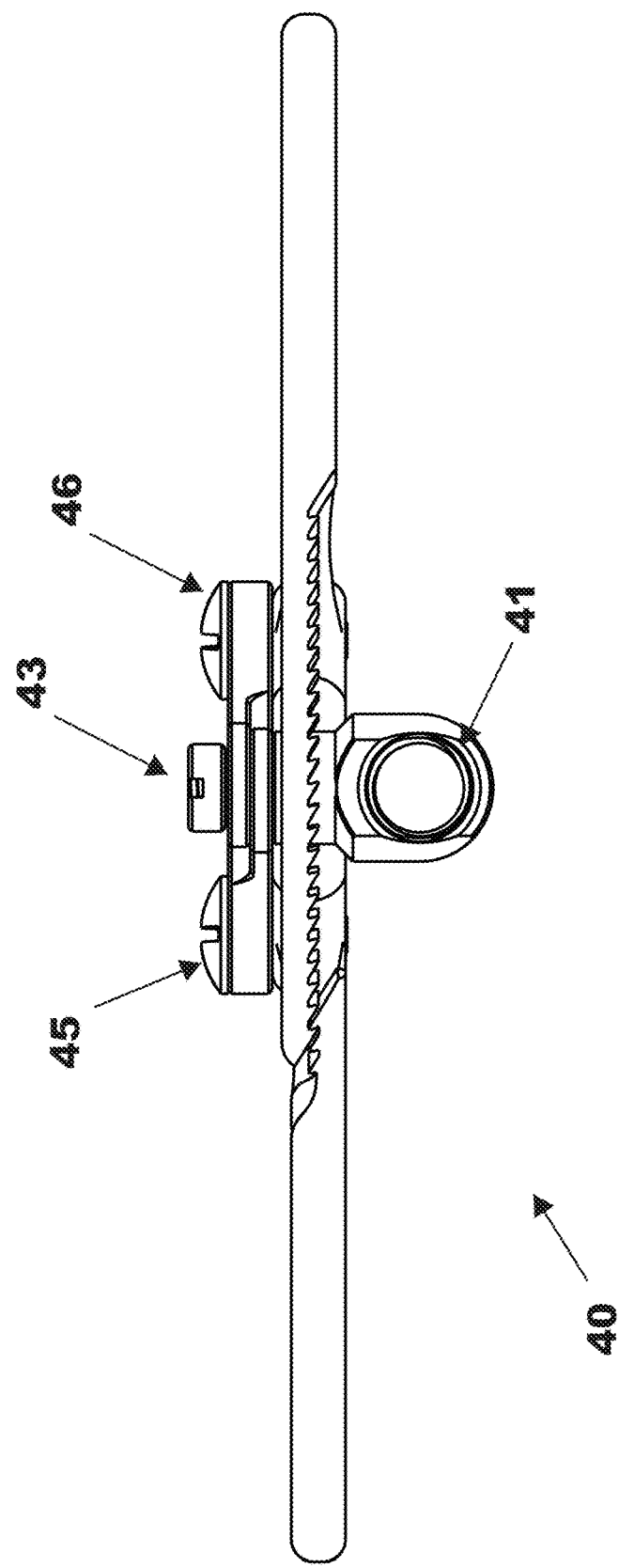
FIG. 21 is a top view of a positioning forceps in accordance with an aspect of an illustrative embodiment.
Figure 22:
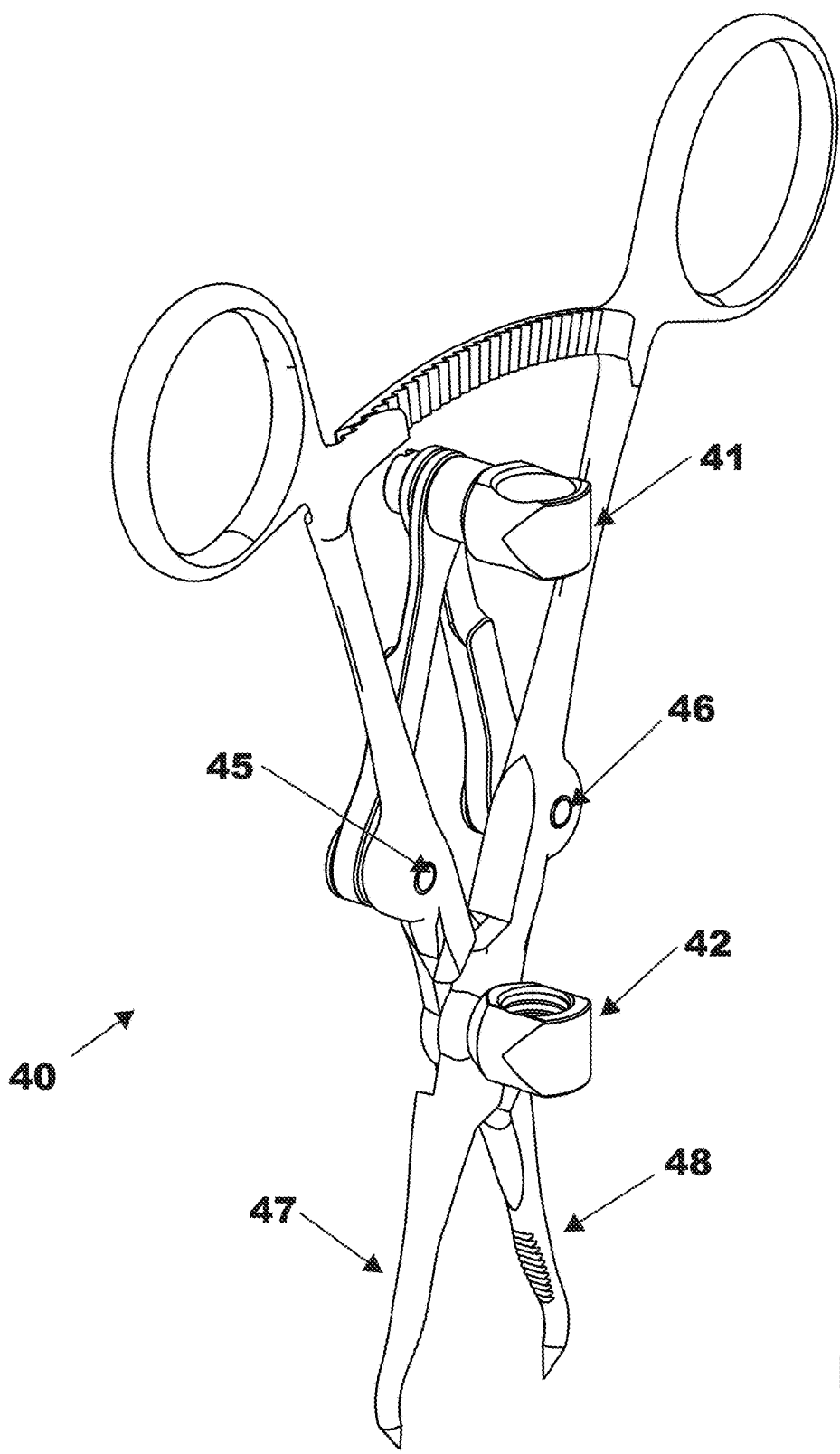
FIG. 22 is a perspective view of a positioning forceps in an open position in accordance with an aspect of an illustrative embodiment.

As shown in FIG. 15, the generally round top portion 31 of locking cap 30 may have an external drive feature 37 around its perimeter. In a preferred embodiment, there are between one to eight drive features. In a more preferred embodiment, there are six drive features 37. In another preferred embodiment, there are four drive features 37. In a preferred embodiment, drive feature 37 may be flat in shape.

When locking cap 30 is tightened by rotating (preferably using a self-retaining hex drive), the bottom of the rounded top portion of locking cap 30 contacts the out cortex of the bone. The edges around cut-out 32 may be sharp so as to cut into the out cortex of the rib itself until the external drive on the lock cap sinks below the outer cortex of the rib. As a result, the external flats are can no longer be engaged by, for example, the self-retaining hex drive.

Turning to FIGS. 17-22, a positioning forceps 40 used in an aspect of an illustrative embodiment is shown. Positioning forceps 40 contains guide holes 41 and 42 that are configured to receive a drill bit guide (not shown). Guide holes 41 and 42 are rotatable around pivots 43 and 44. Positioning forceps 40 also contains reference pivots 45 and 46. Reference pivots 45 and 46 are attached to forceps arms 47 and 48. The positioning forceps is most preferably made of stainless steel. In a preferred embodiment, forceps arms 47 and 48 are each made from a single piece of metal. The double-pivot double guide design of forceps 40 provides stability and the ability of a drill sleeve (not shown) to remain centered over a bone segment (not shown). In a preferred embodiment, pivot 44 is load bearing.

Figure 23:
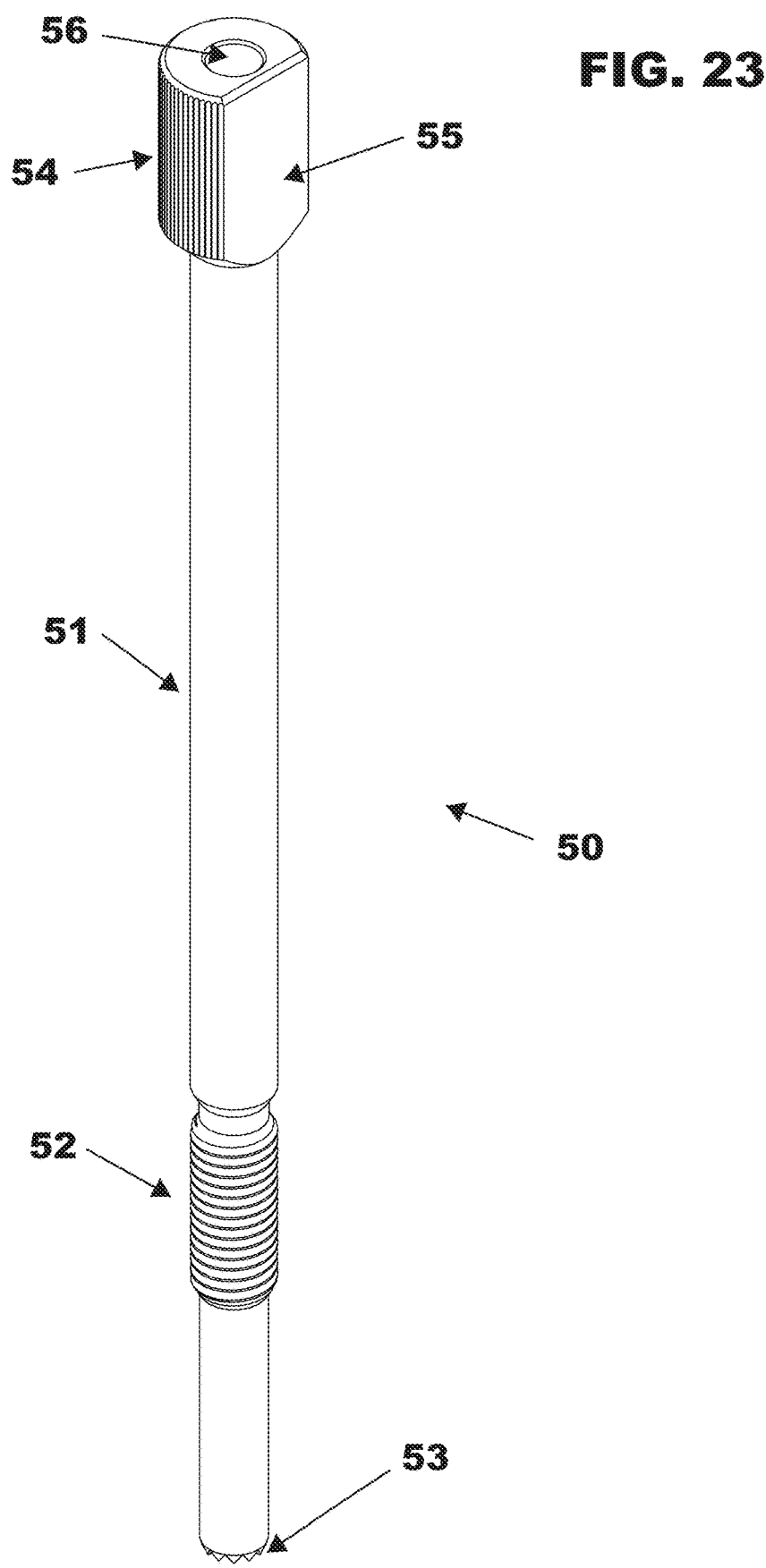
FIG. 23 is a perspective view of a drill bit guide in accordance with an aspect of an illustrative embodiment.

Turning to FIG. 23, a drill bit guide 50 is shown. Drill bit guide 50 has a shaft 51. Shaft 51 has threaded portion 52 to facilitate threading the shaft in guide hole 42 of positioning forceps 40. Shaft 51 also has a serrated edge 53 on the side designed to contact a bone segment. This permits the drill bit 50 guide to cut through tissue surrounding the bone segment. Shaft 51 has a generally rounded knob 54 at its top. Knob 54 has a flat portion 55 to prevent the knob from rolling, for example, on an operating tray. Shaft 51 also has longitudinal channel 56 along its length configured to receive and guide a drill bit (not shown). The drill bit guide 50 is most preferably made of stainless steel.

Figure 24:
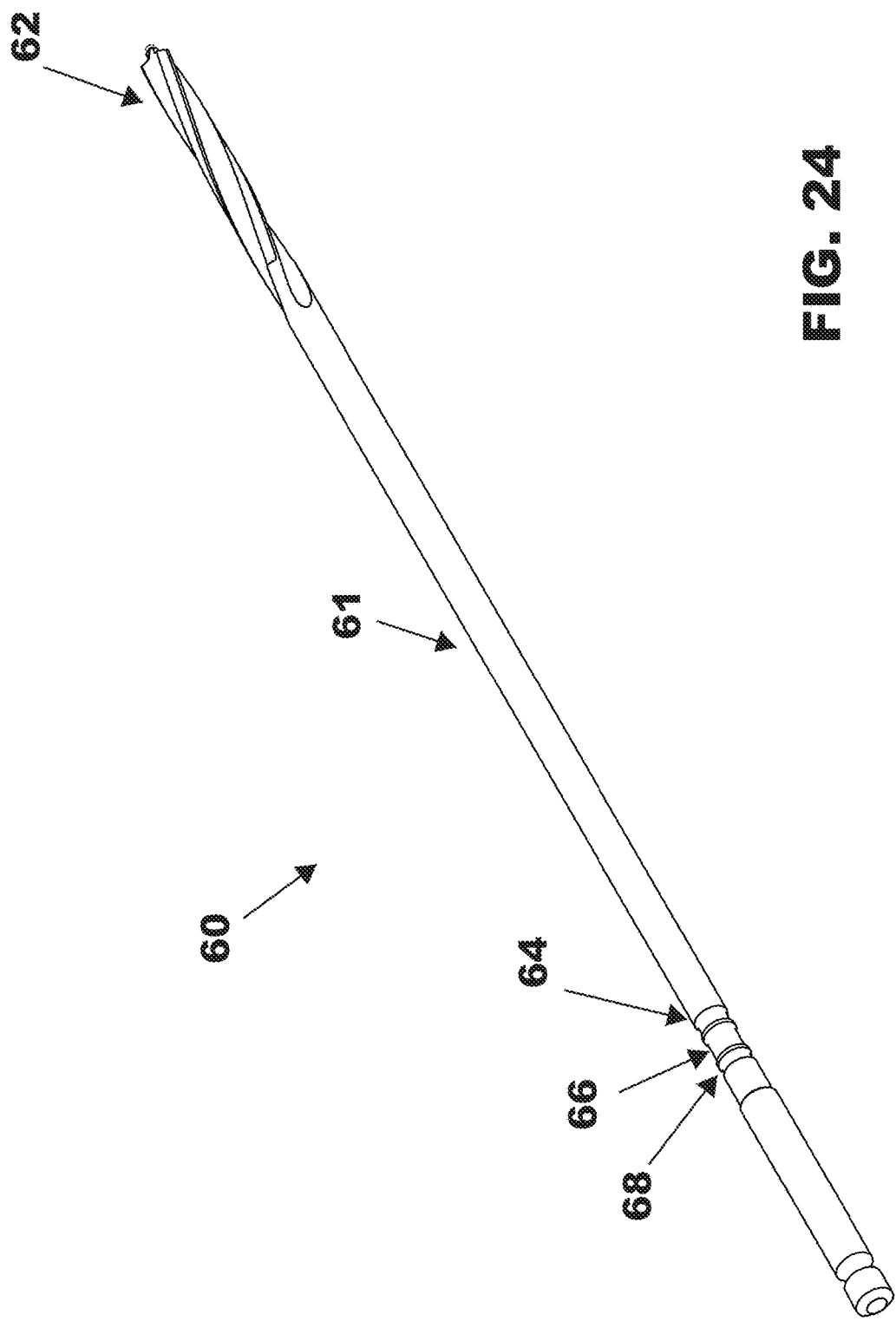
FIG. 24 is a perspective view of a drill bit in accordance with an aspect of an illustrative embodiment.

Turning to FIG. 24, a drill bit 60 is shown. Drill bit 60 has a shaft 61 and a point 62 at one end of shaft 61 of sufficient sharpness to drill into bone. In a preferred embodiment, drill bit 60 has drill depth indicators 64, 66 and 68 to illustrate how deeply a bone has been drilled. These depth indicators may be color coded. For example, depth indicator 64 could be blue-colored. Depth indicator 66 may be red-colored. Depth indicator 68 may be green colored. Drill depth indicators 64, 66 and 68 permit the selection of an outer fastener of different length depending on how deeply a bone has been drilled. The outer fastener may also be color coded to correlate with the color of the drill depth indicator. The drill bit is most preferably made of stainless steel.

Figure 25:
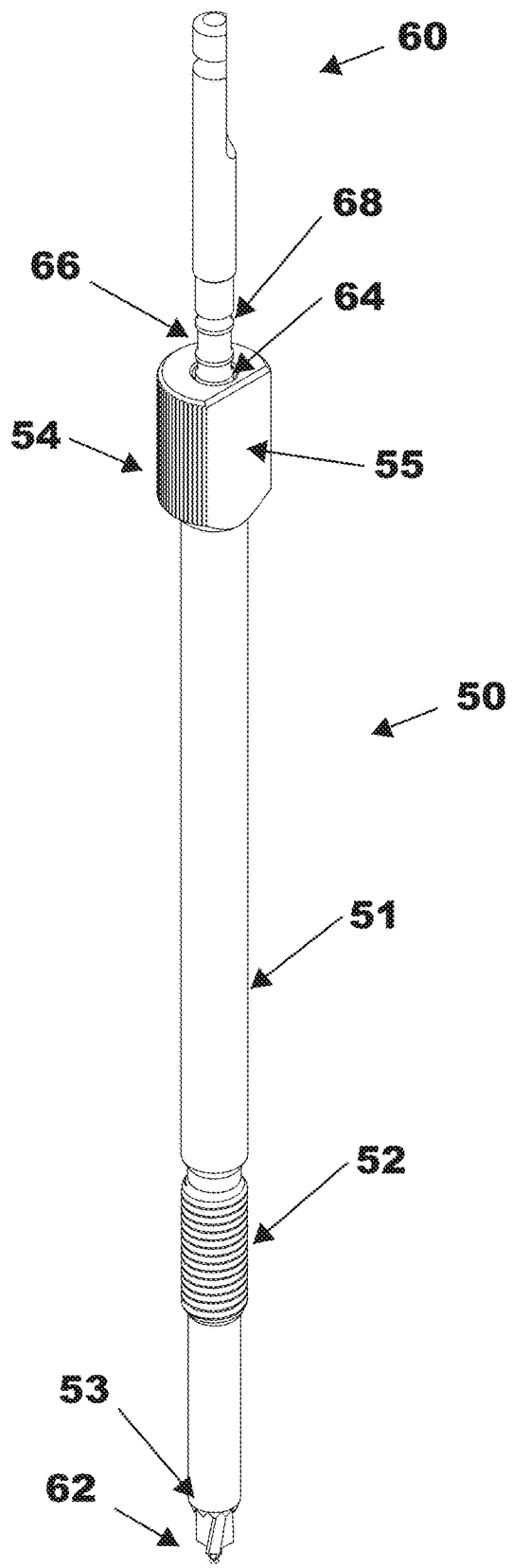
FIG. 25 is a perspective view of a drill bit inserted in a drill bit guide in accordance with an aspect of an illustrative embodiment.

FIG. 25 shows a drill bit guide 50 with drill bit 60 inserted therein. Point 62 protrudes from the bottom of drill guide 50 and drill depth indicators 64, 66 and 68 are also illustrated.

Figure 26:
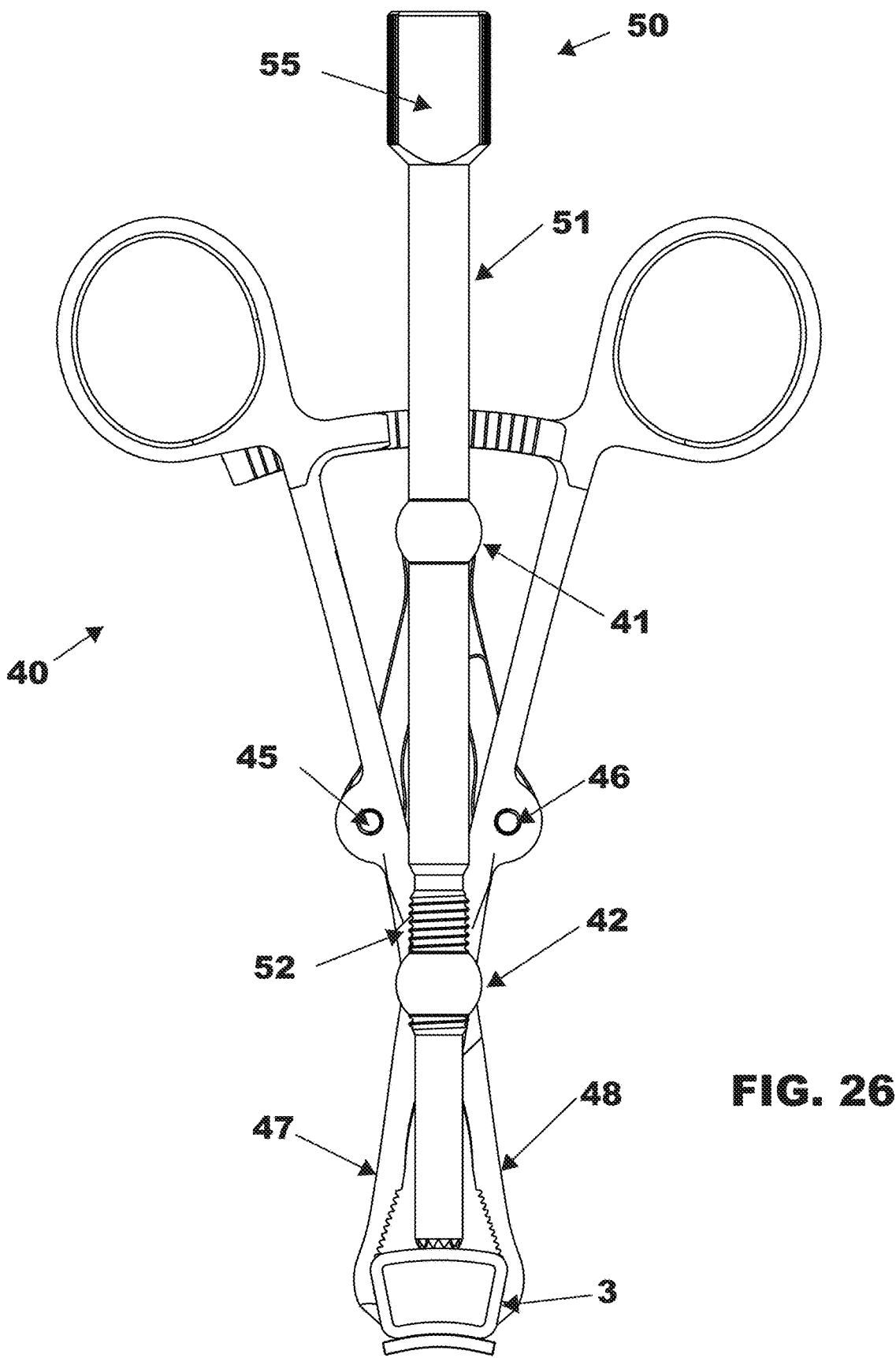
FIG. 26. is a front view of a positioning forceps with a drill bit guide contacting a bone segment in accordance with an aspect of an illustrative embodiment.

FIG. 26 shows a positioning forceps 40 with drill bit guide 50 inserted into guide holes 41 and 42 and contacting bone segment 3 such that drill bit 60 (not shown) is generally centered over the width of bone segment 3.

Figure 27:
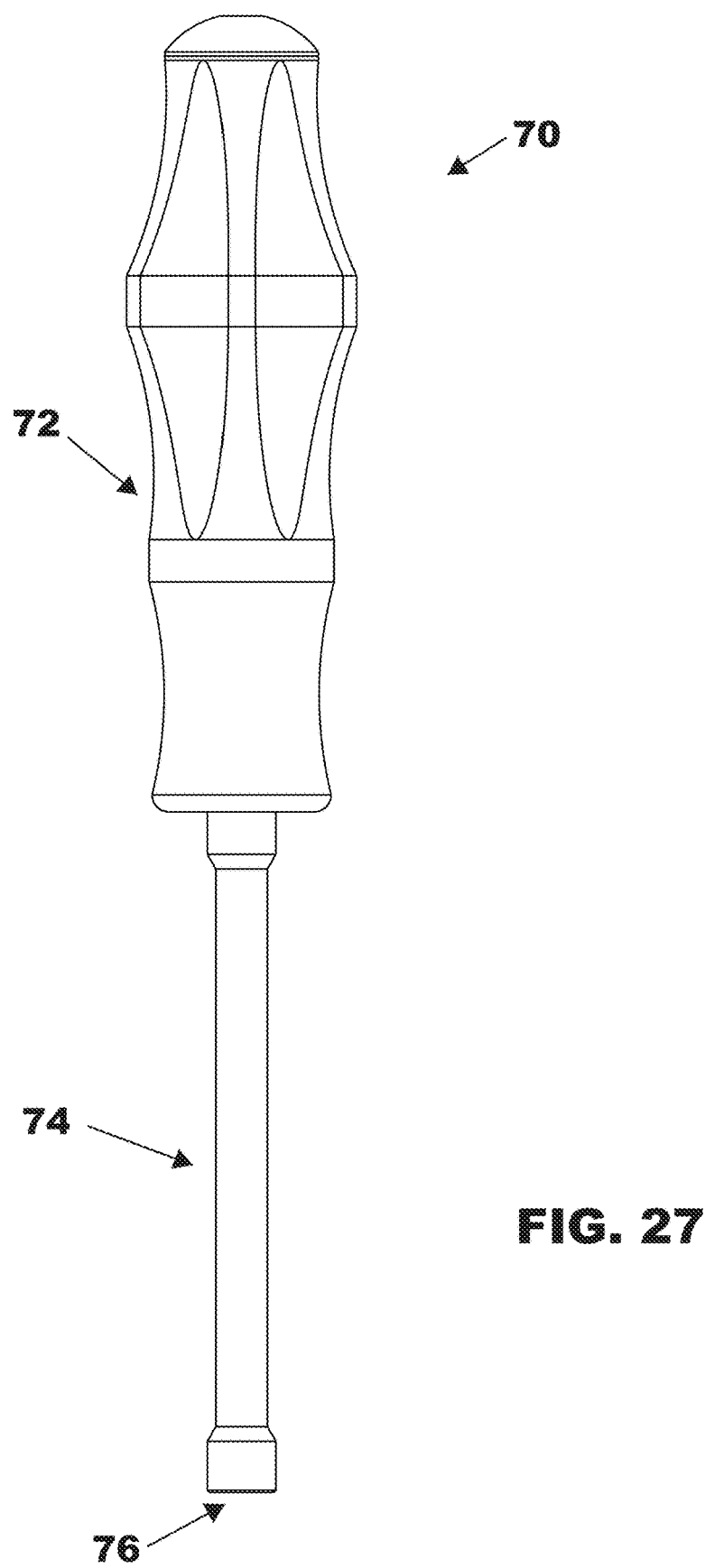
FIG. 27 is a side view of an external drive tool in accordance with an aspect of an illustrative embodiment.
Figure 28:
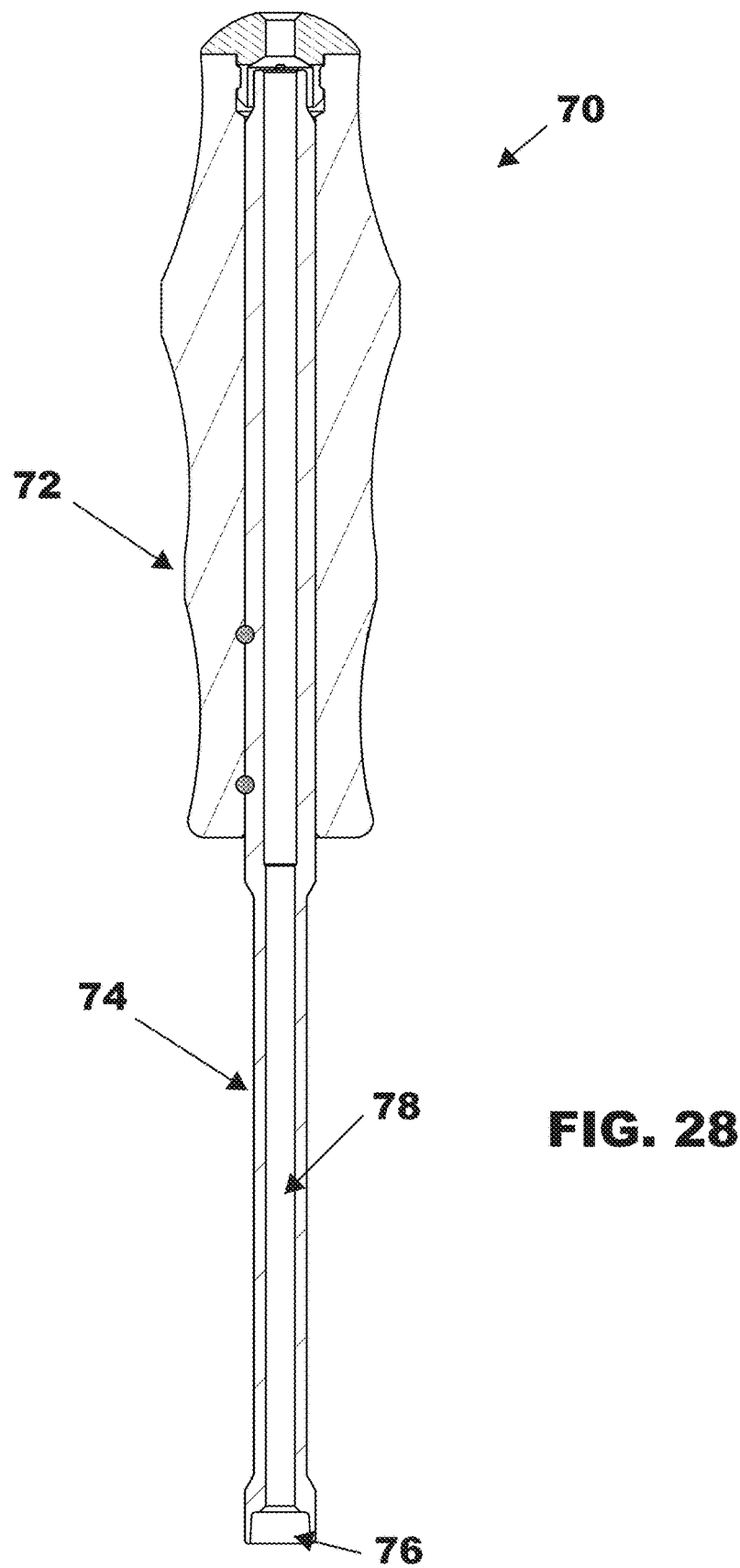
FIG. 28 is a side cut-away view of an external drive tool self-retaining hex drive in accordance with an aspect of an illustrative embodiment.
Figure 29:
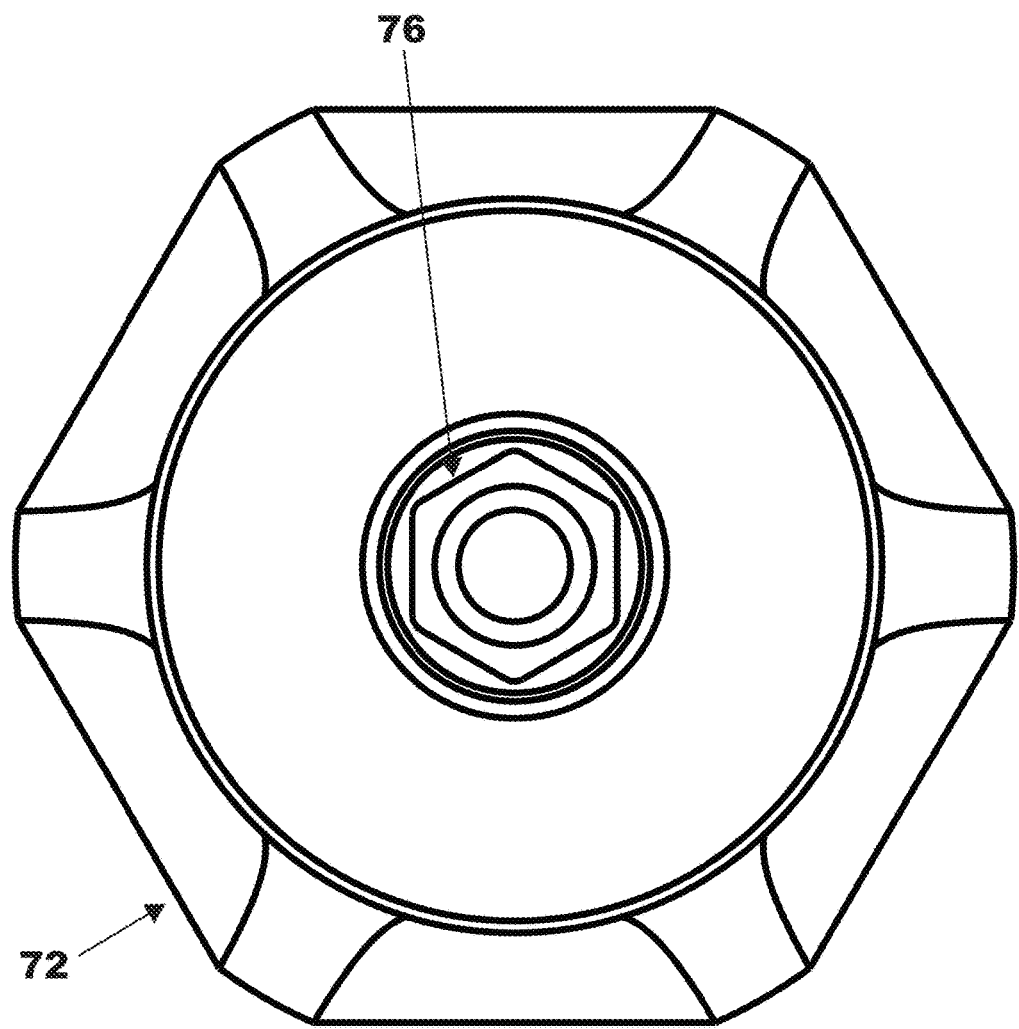
FIG. 29 is a bottom view of an external drive tool in accordance with an aspect of an illustrative embodiment.

FIG. 27 shows an external drive tool. 70. External drive tool 70 has a handle 72 at one end attached to a drive shaft 74 which is connected to a drive portion 76. As shown in FIG. 28 External drive tool 70 further contains a longitudinal channel 78 along its length which is configured to receive a tether (not shown) used in an aspect of an illustrative embodiment. The handle of the drive tool is most preferably made of plastic, rubber, or silicon. The shaft and the drive portion are most preferably made of stainless steel. FIG. 29 shows a head-on view of drive portion 76.

Turning to FIGS. 30-53, a method of using the bone repair system to repair a patient's broken rib is illustrated. It should be understood that additional surgical steps may be performed and still be within the scope of the instant method.

Figure 30:
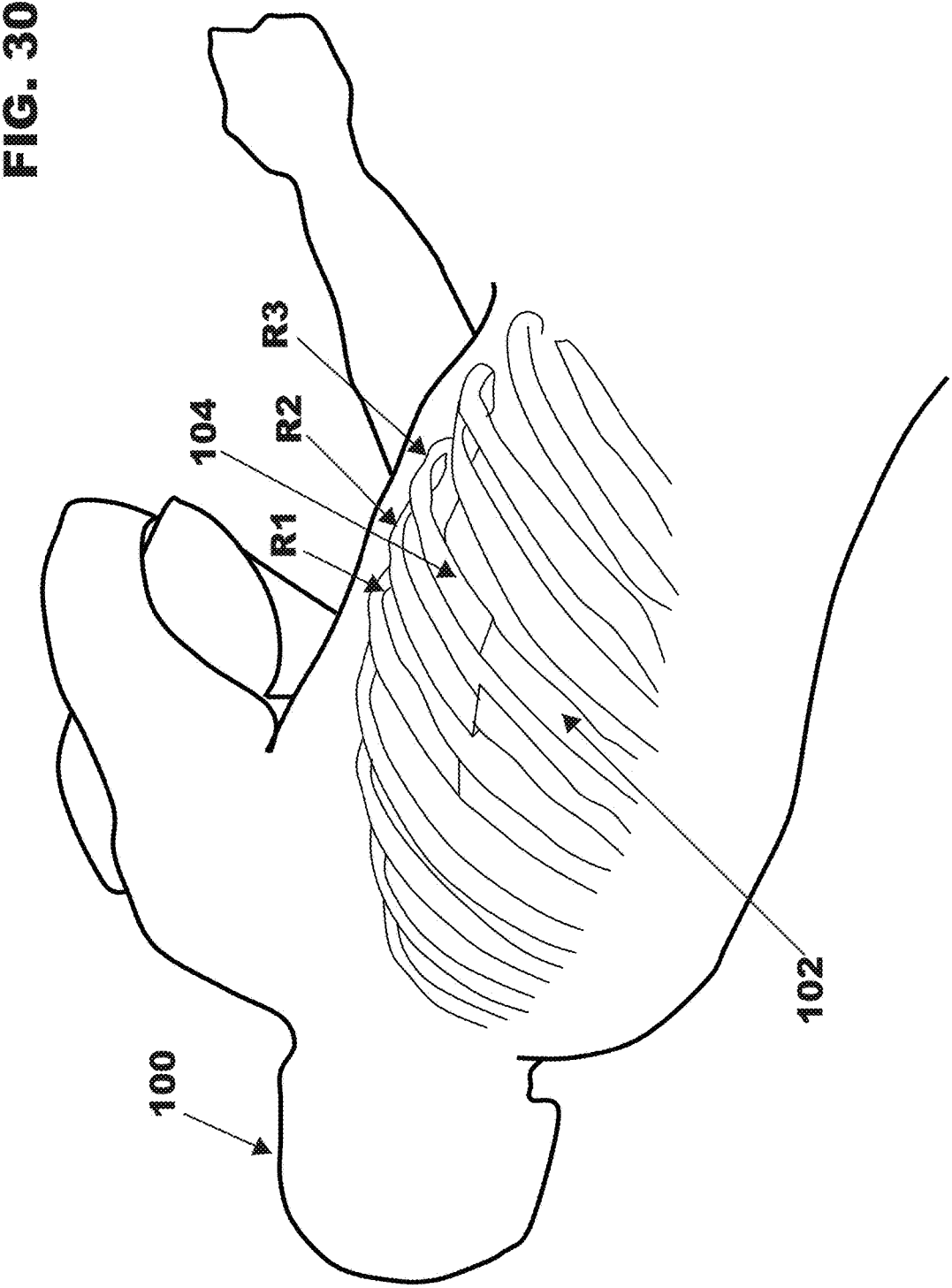
FIG. 30 is an illustration of a patient with broken ribs.
Figure 31:
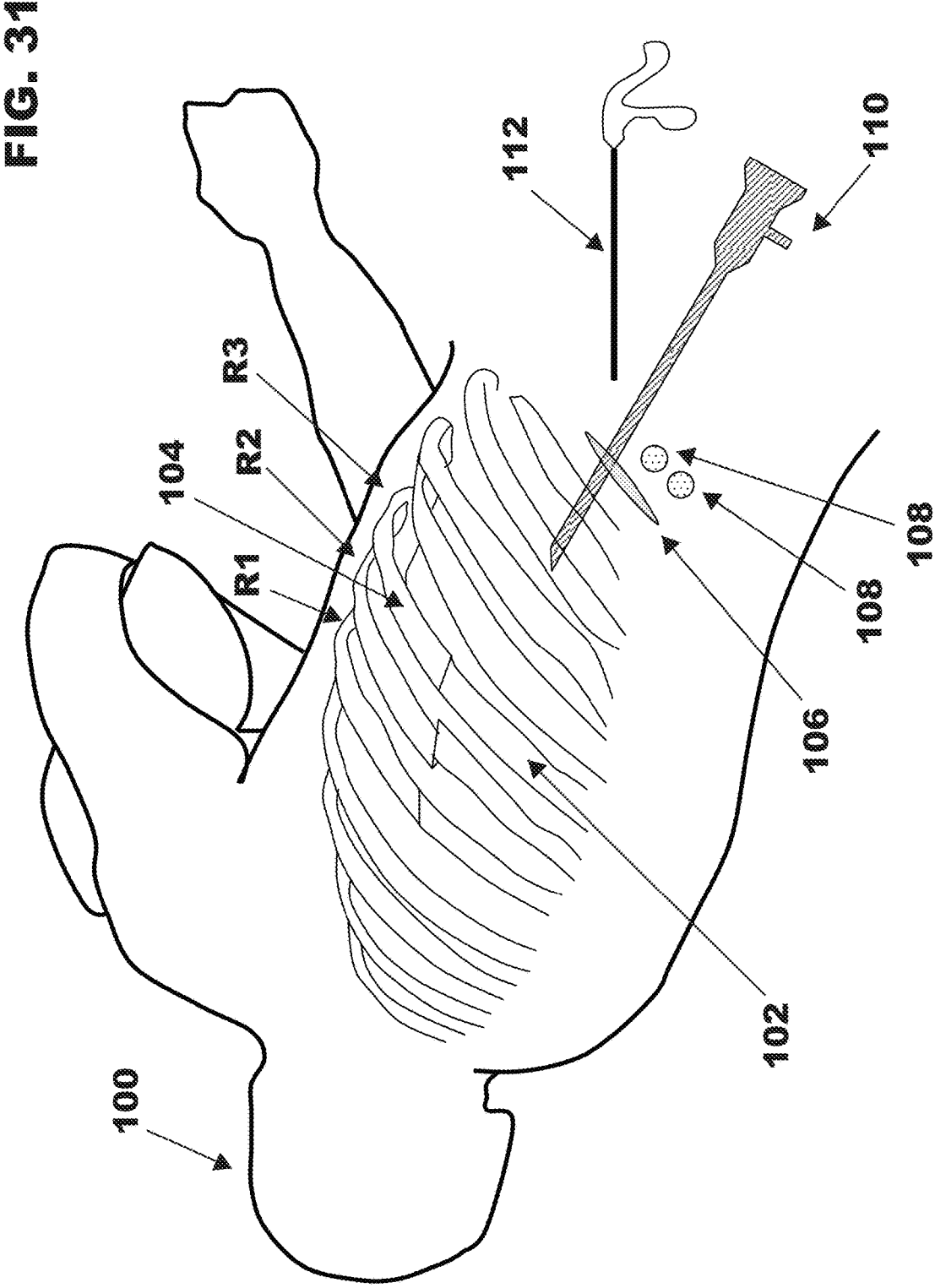
FIG. 31 is an illustration of an incision and ports in accordance with an aspect of an illustrative embodiment.

FIG. 30 shows a patient 100 with three broken ribs R1, R2, and R3. Each broken rib has a first bone segment 102 and a second bone segment 104. FIG. 31 shows an incision 106 and ports 108 made in the patient's 100 body in an area below the rib cage. Incision 106 and ports 108 may be used to insert surgical tools 110 and 112 including such tools as an endoscope. It should be understood that single or multiple incisions could be used in the instant invention. Similarly, one or more ports 108 could be used in the instant invention. Later figures show an incision 106 for convenience of illustration.

Figure 32:
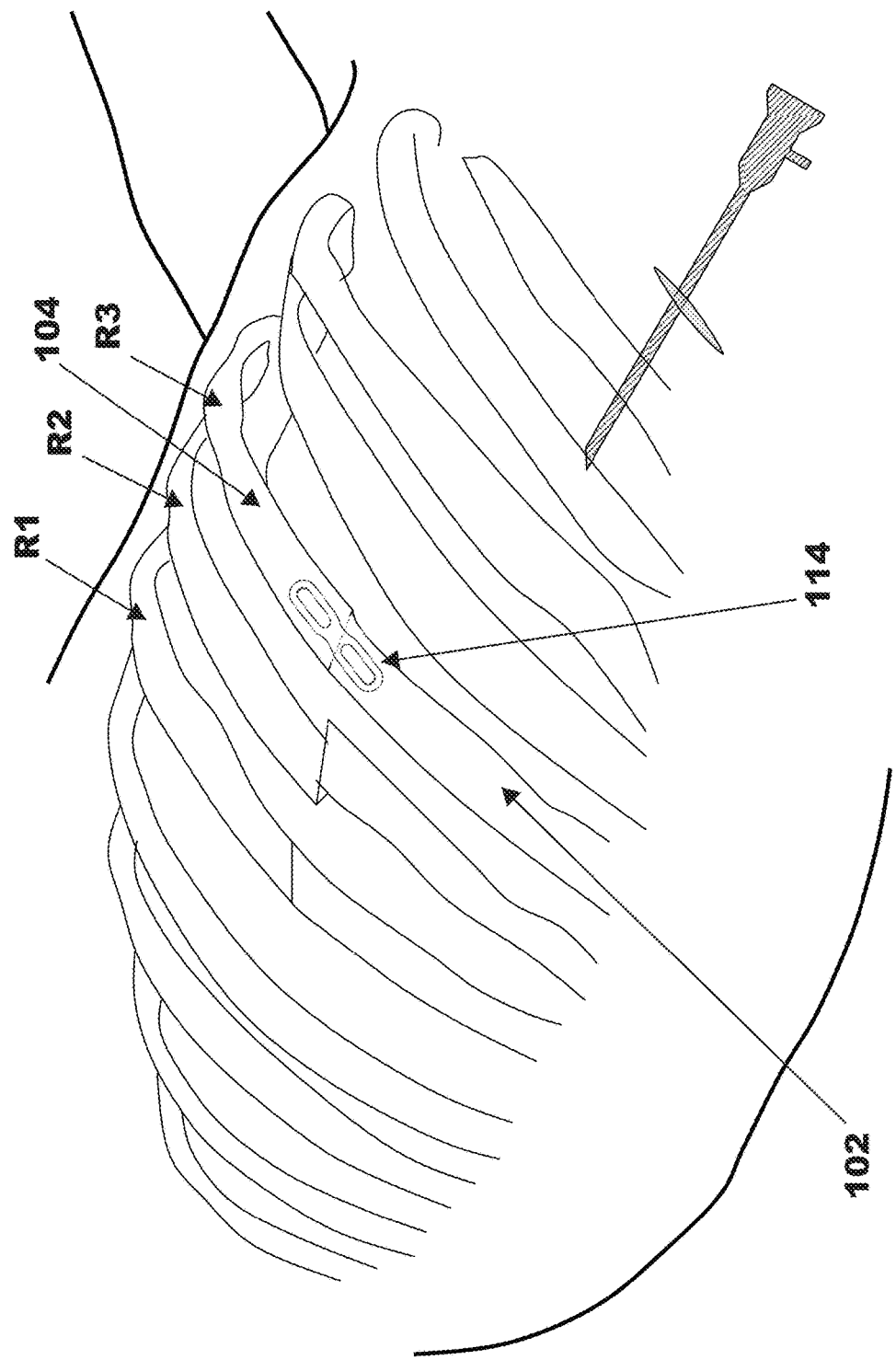
FIG. 32 is an illustration of an incision template placed over a patient's broken ribs in accordance with an aspect of an illustrative embodiment.

FIG. 32 shows an incision template 114 placed over first bone segment 102 and second bone segment 104. The template is an optional feature in an aspect of an illustrative embodiment to assist a surgeon in locating potential points of incision above rib bone segments 102 and 104. The incision template 114 has a similar geometry to longitudinal member 4. The incision template is preferably made of stainless steel.

Figure 33:
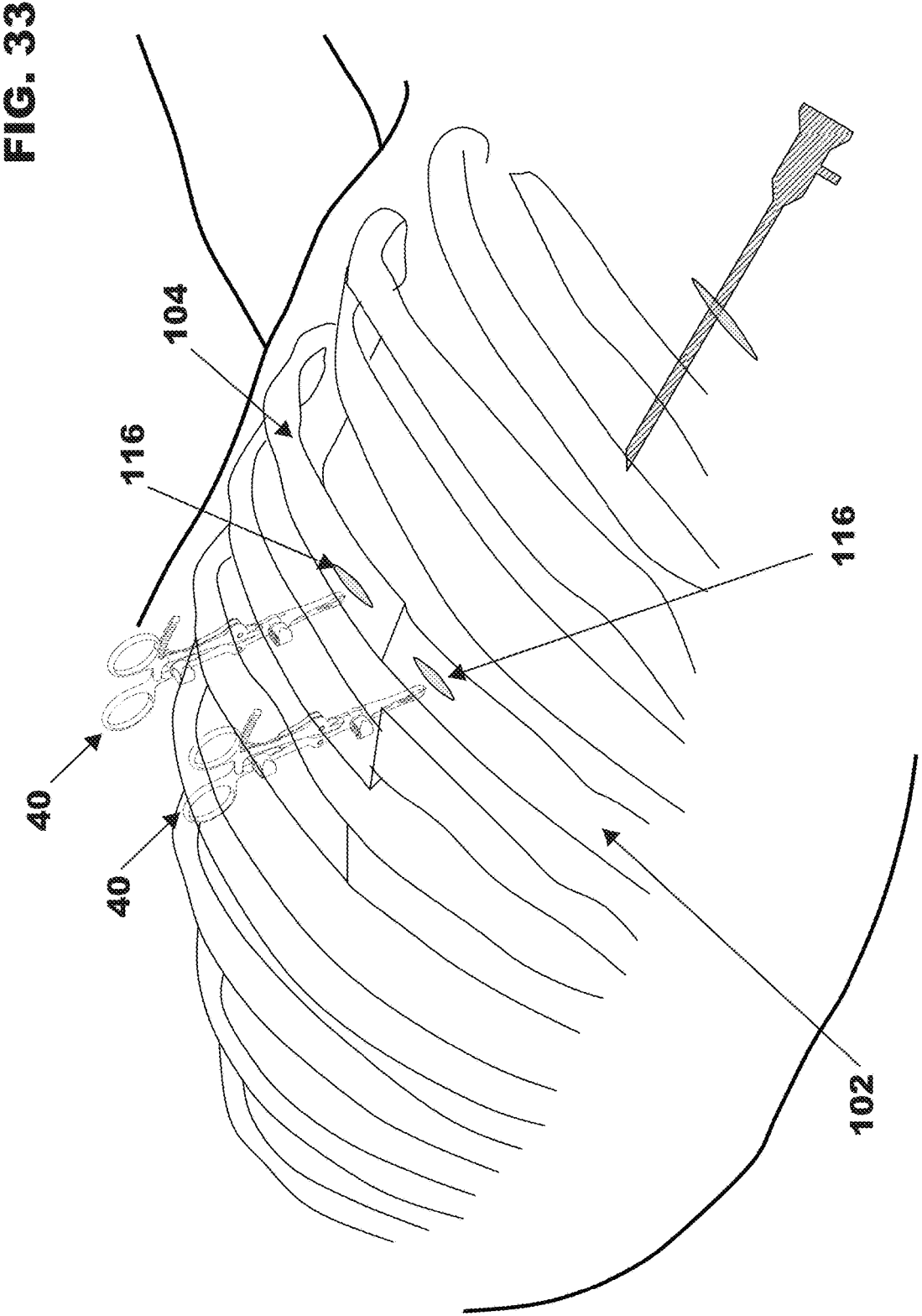
FIG. 33 is an illustration of the positioning forceps about to be inserted into incisions over the patient's broken ribs in accordance with an aspect of an illustrative embodiment.

FIG. 33 shows positioning forceps 40 about to be inserted into incisions 116 made using the incision template 114.

Forceps 40 are preferably inserted in closed position through the skin incision 116. Once the tip of the forceps 40 contacts the outer cortex of the rib, the forceps 40 are opened, thereby allowing the tips of forceps 40 to go over each edge of the rib.

Figure 34:
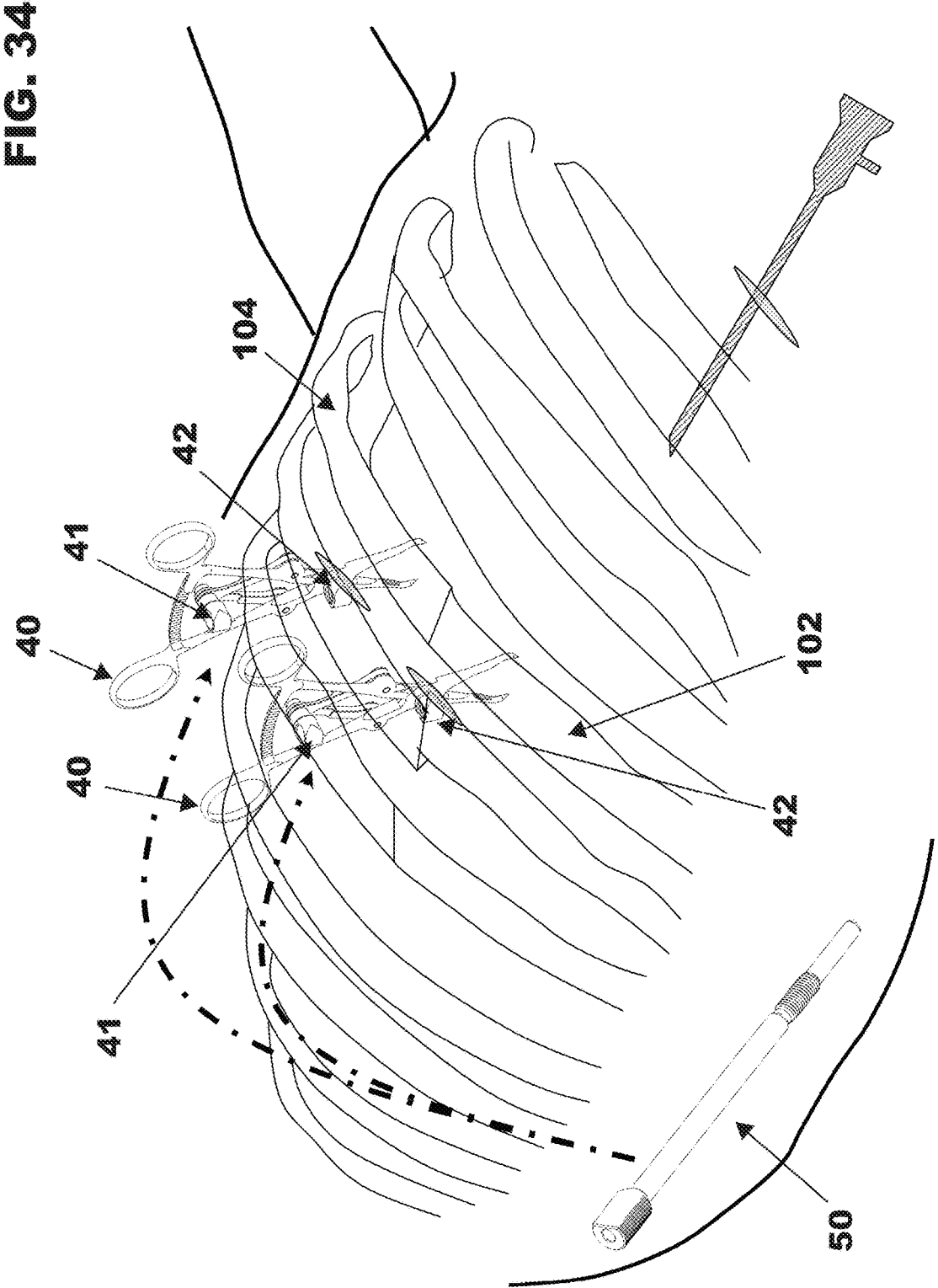
FIG. 34 is an illustration of the positioning forceps contacting bone segments in the patient's broken ribs in accordance with an aspect of an illustrative embodiment.
Figure 35:
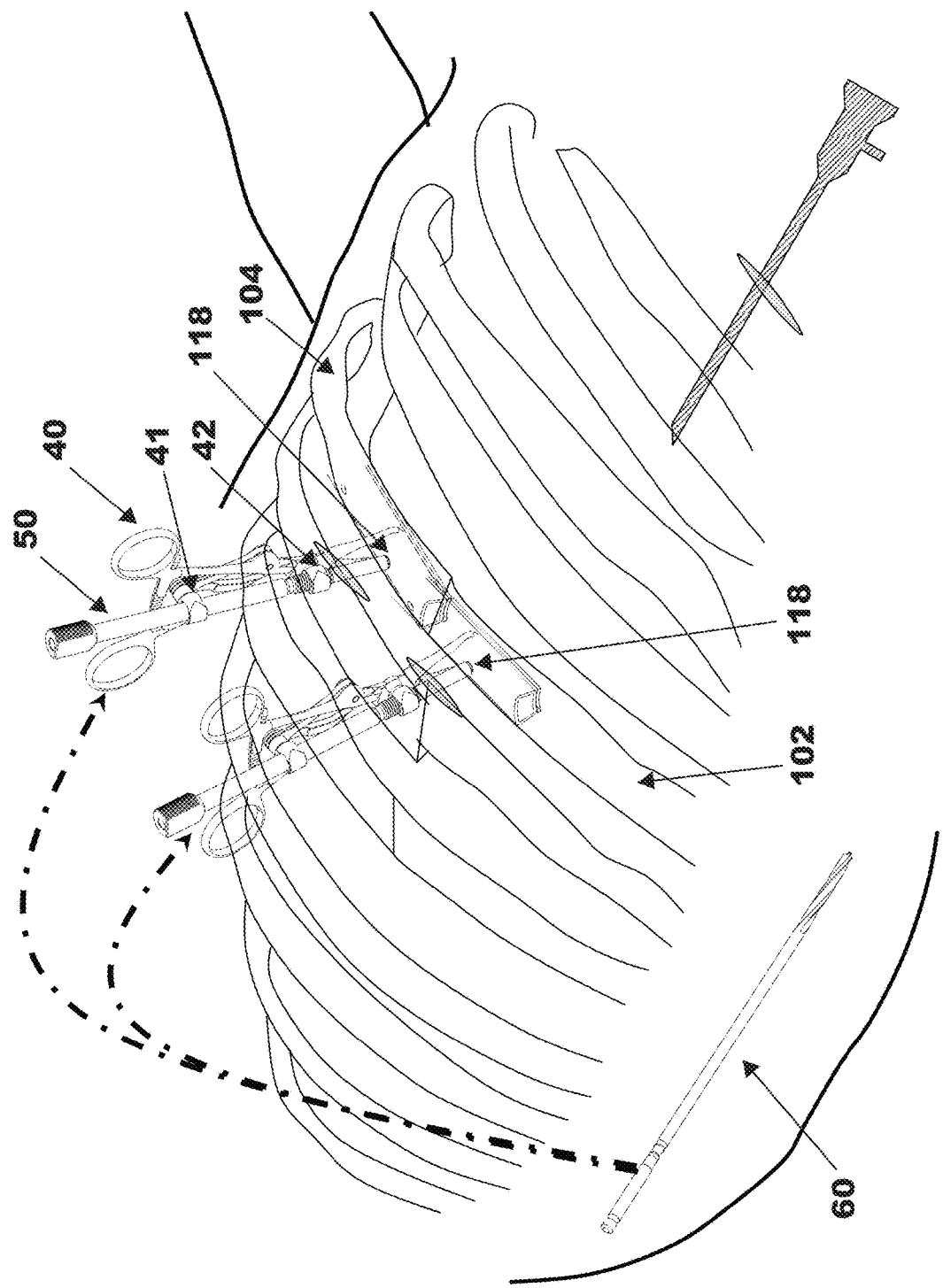
FIG. 35 is an illustration of the positioning forceps of FIG. 34 with drill bit guides inserted into the forceps in accordance with an aspect of an illustrative embodiment.

In FIG. 34, positioning forceps 40 are engaged to bone segments 102 and 104. Drill bit guide 50 is shown prior to insertion in guide holes 41 and 42. In FIG. 35, positioning forceps 40 containing drill bit guide 50 inserted into guide holes 41 and 42 prior to insertion of drill bit 60 into drill bit guide 50. Drill bit 60 is used to drill holes 118 (not explicitly shown) into bone segments 102 and 104.

Figure 36:
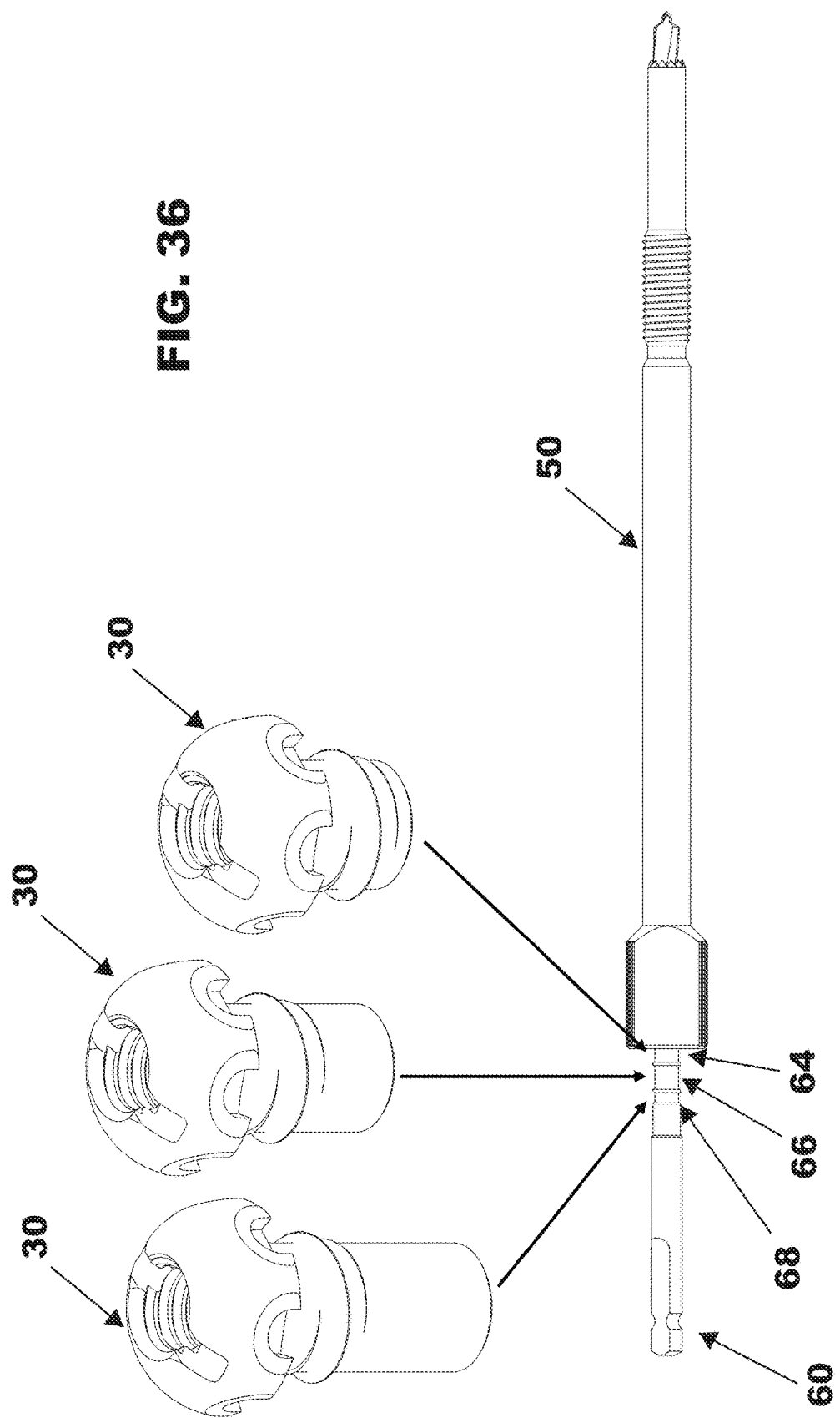
FIG. 36 is a perspective view of a drill bit with indicators for indicating the depth of a hole made by the drill bit along with locking caps configured to be used in drill holes of varying depth in accordance with an aspect of an illustrative embodiment.

In FIG. 36, drill bit 60 is inserted into drill bit guide 50. Drill bit 60 has drill depth indicators 64, 66, and 68 are shown on drill bit 60. In a preferred embodiment, various sizes of locking caps 30 may be selected based on the depth of the hole drilled in a bone segment according to depth indicators 64, 66, and 68.

Figure 37:
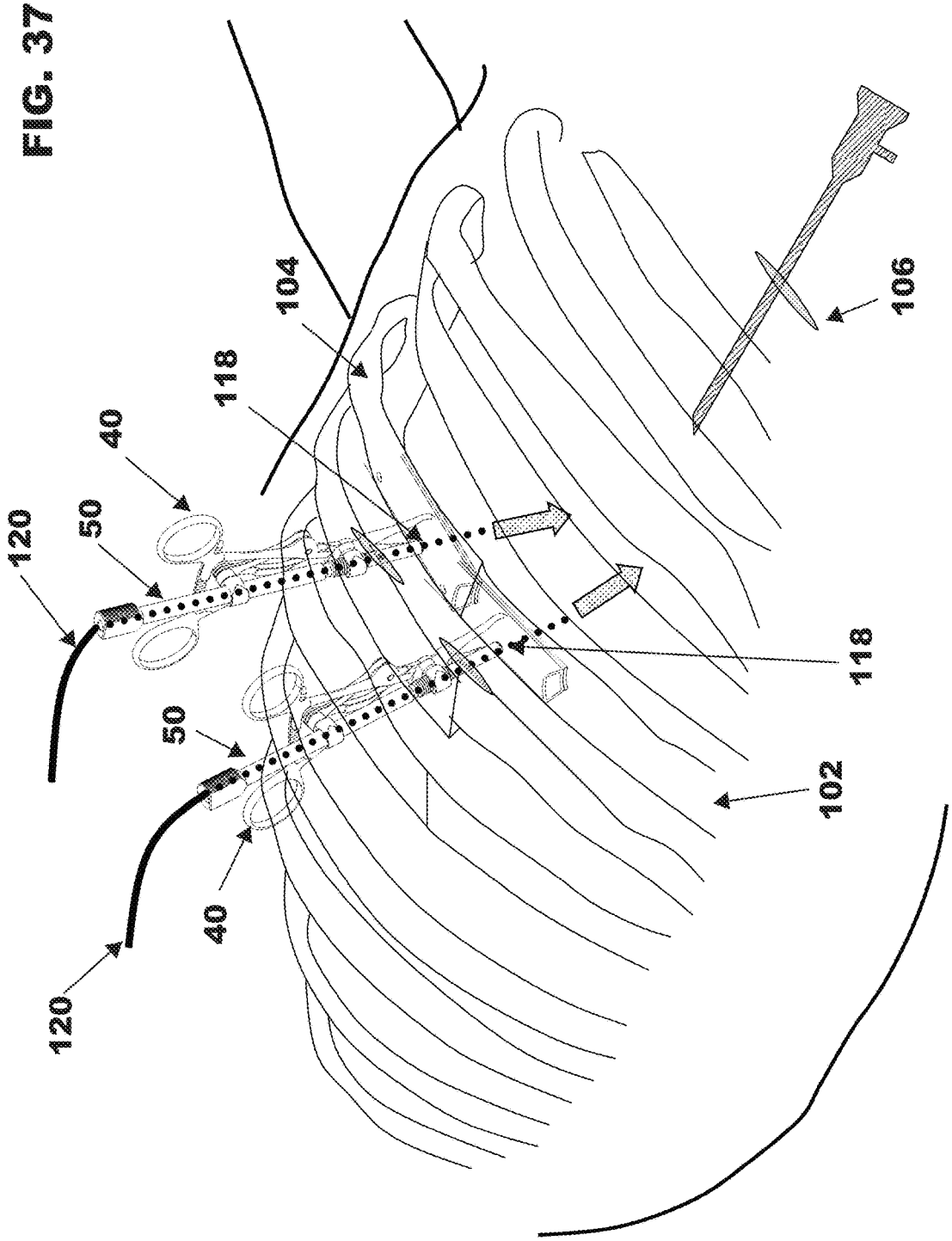
FIG. 37 is an illustration of guide tubes being inserted into the drill bit guides in accordance with an aspect of an illustrative embodiment.
Figure 38:
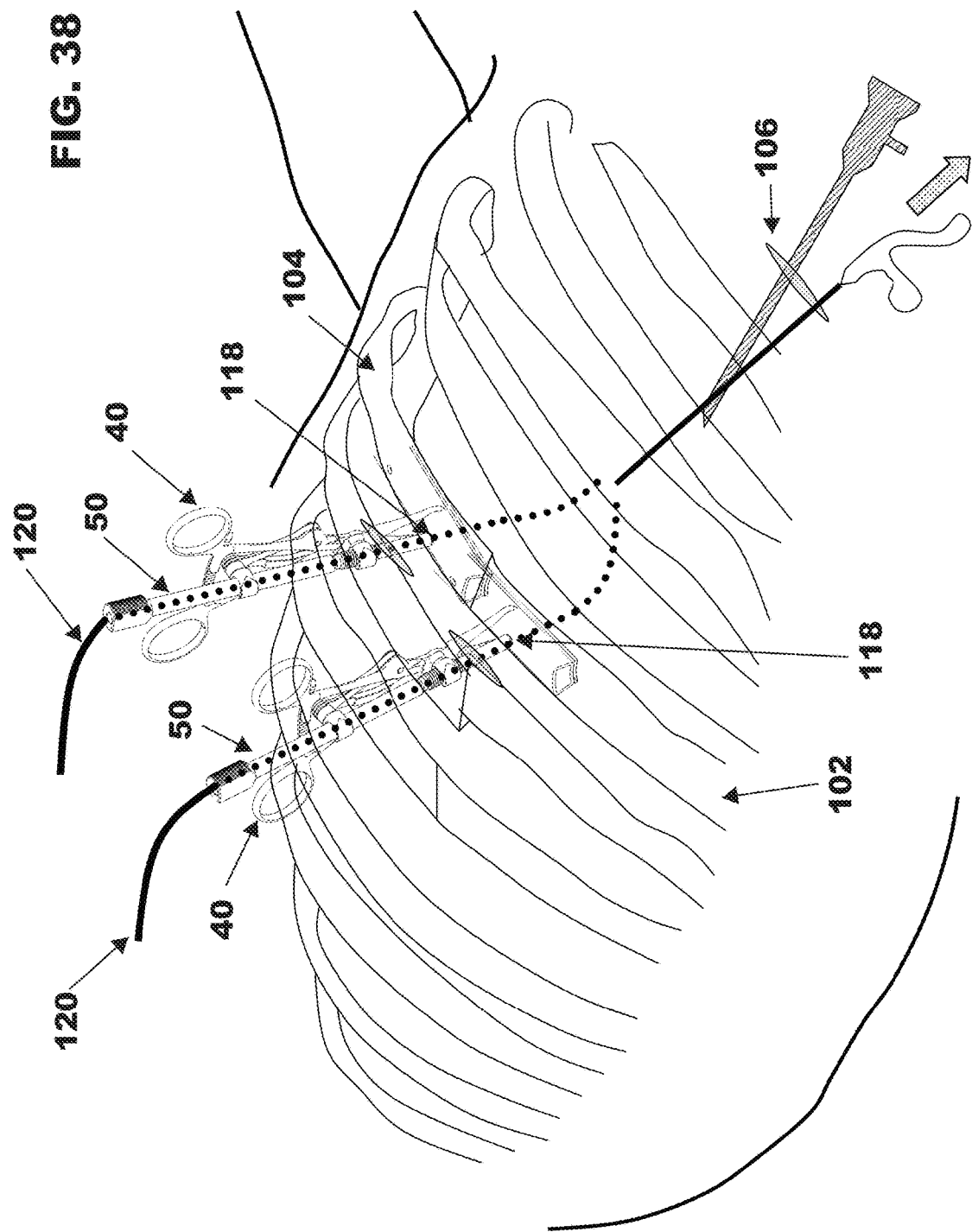
FIG. 38 is an illustration of guide tubes being inserted through holes in the bone segments of the patient's broken ribs in accordance with an aspect of an illustrative embodiment.
Figure 39:
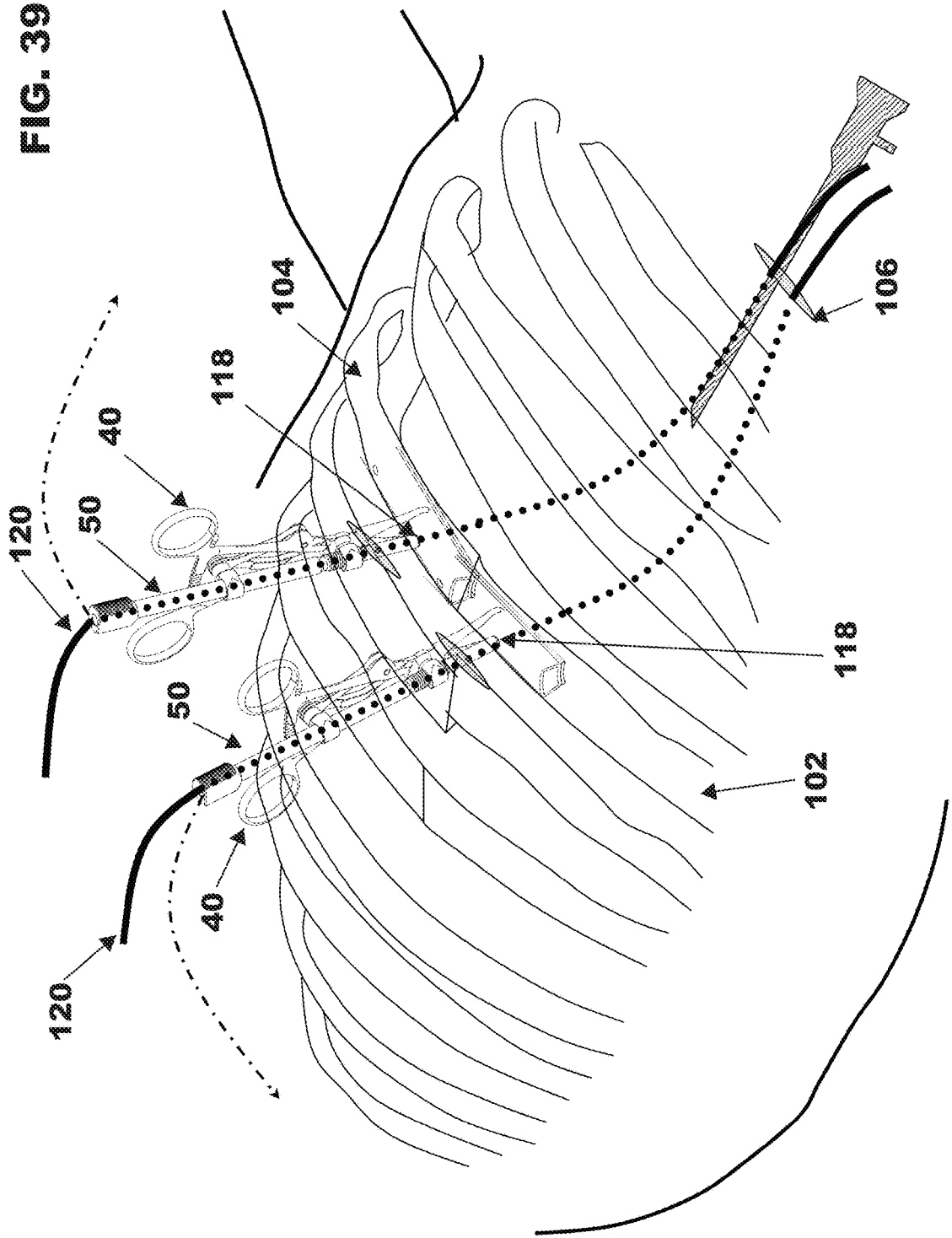
FIG. 39 is an illustration of the ends of the guide tubes being removed from an incision away from the patient's ribs in accordance with an aspect of an illustrative embodiment.

In FIGS. 37 to 39, guide tubes 120 are inserted into drill bit guide 50 and fed through the holes 118 in bone segments 102 and 104. In a preferred embodiment, one end of guide tubes 120 are pulled outside the patient's body through incision 106 while the other end of the guide tubes 120 remains outside the patient's body above bone segments 102 and 104. Guide tubes 120 are most preferably made of fluoropolymer plastic. The guide tubes preferably have an inner diameter in a range from 0.5 to 10 mm. A preferred inner diameter is 1.6 mm. The guide tubes 120 preferably also have a preferred outer diameter from 2 mm to 12 mm. A preferred outer diameter is 3.2 mm. A preferred length is 1000 mm. The use of plastic guide tubes may allow the guide tubes to be directed through the body more easily and safely than bare tethers (which may be made of metal). This may provide for smoother, less traumatic and efficient passage through the body.

Figure 40:
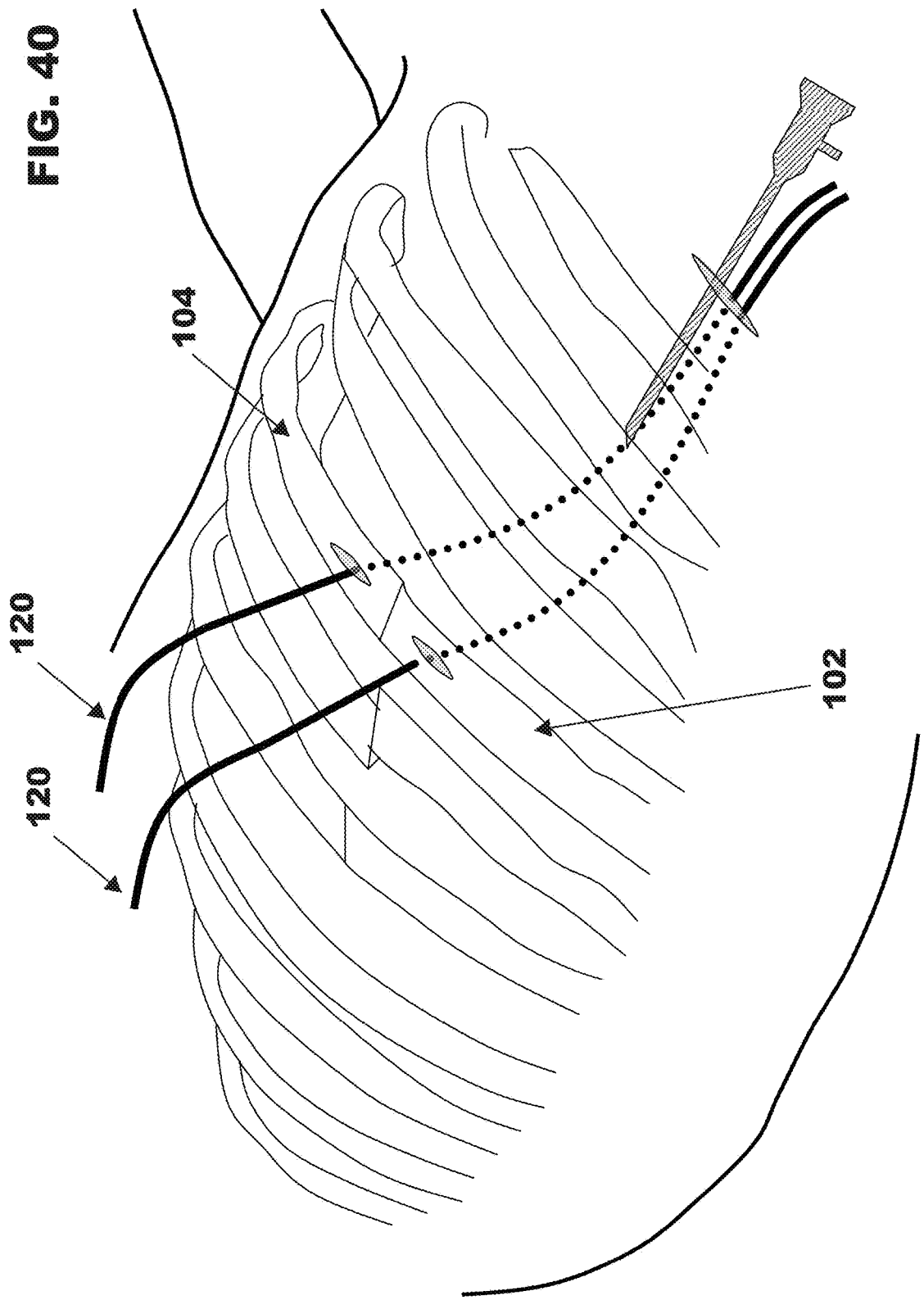
FIG. 40 is an illustration showing the guide tubes after the ends of the guide tubes have been removed from an incision away from the patient's ribs in accordance with an aspect of an illustrative embodiment.
Figure 41:
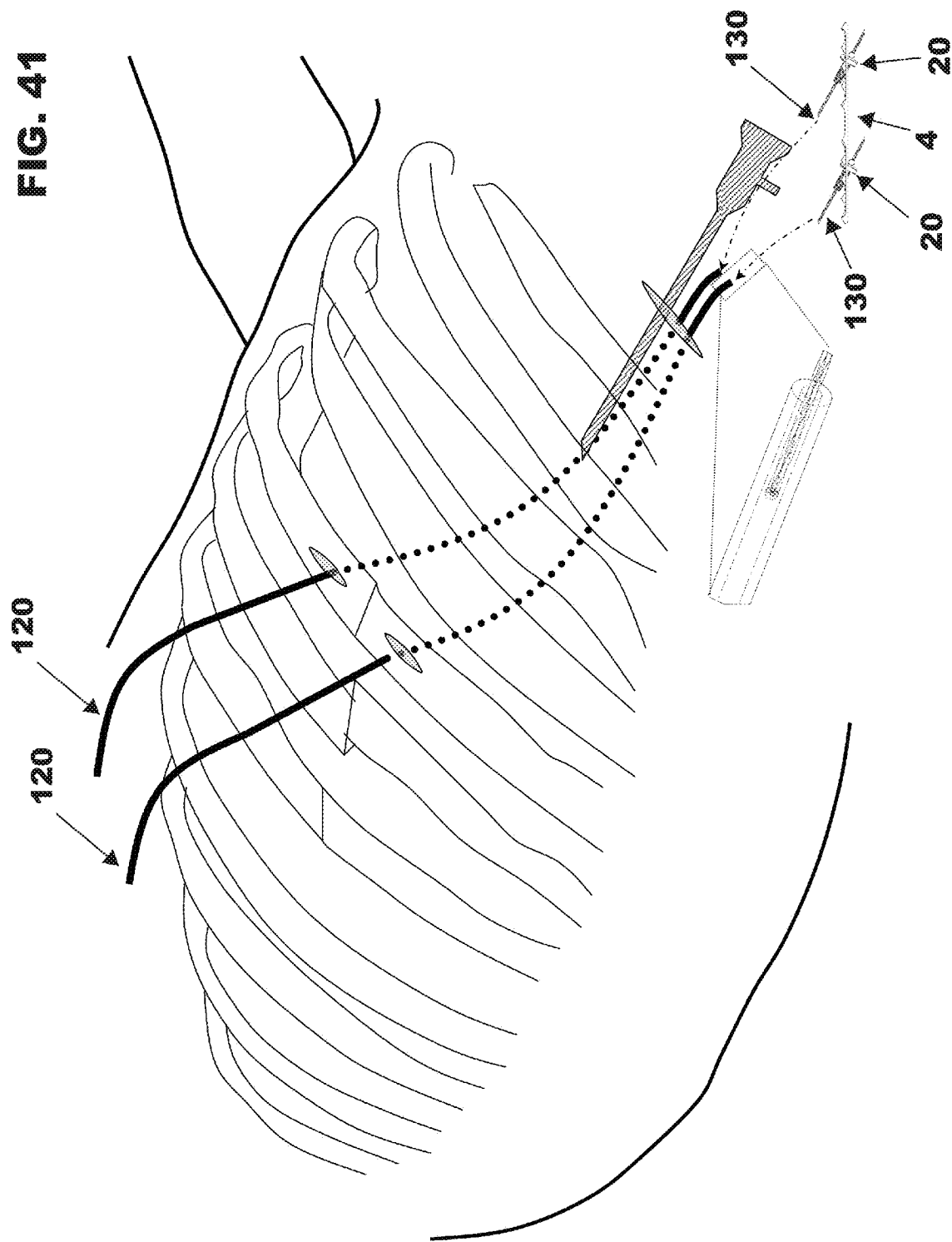
FIG. 41 is an illustration of a tether inserted through the pivoting locking posts of the longitudinal member being inserted into the guide tubes in accordance with an aspect of an illustrative embodiment.
Figure 42:
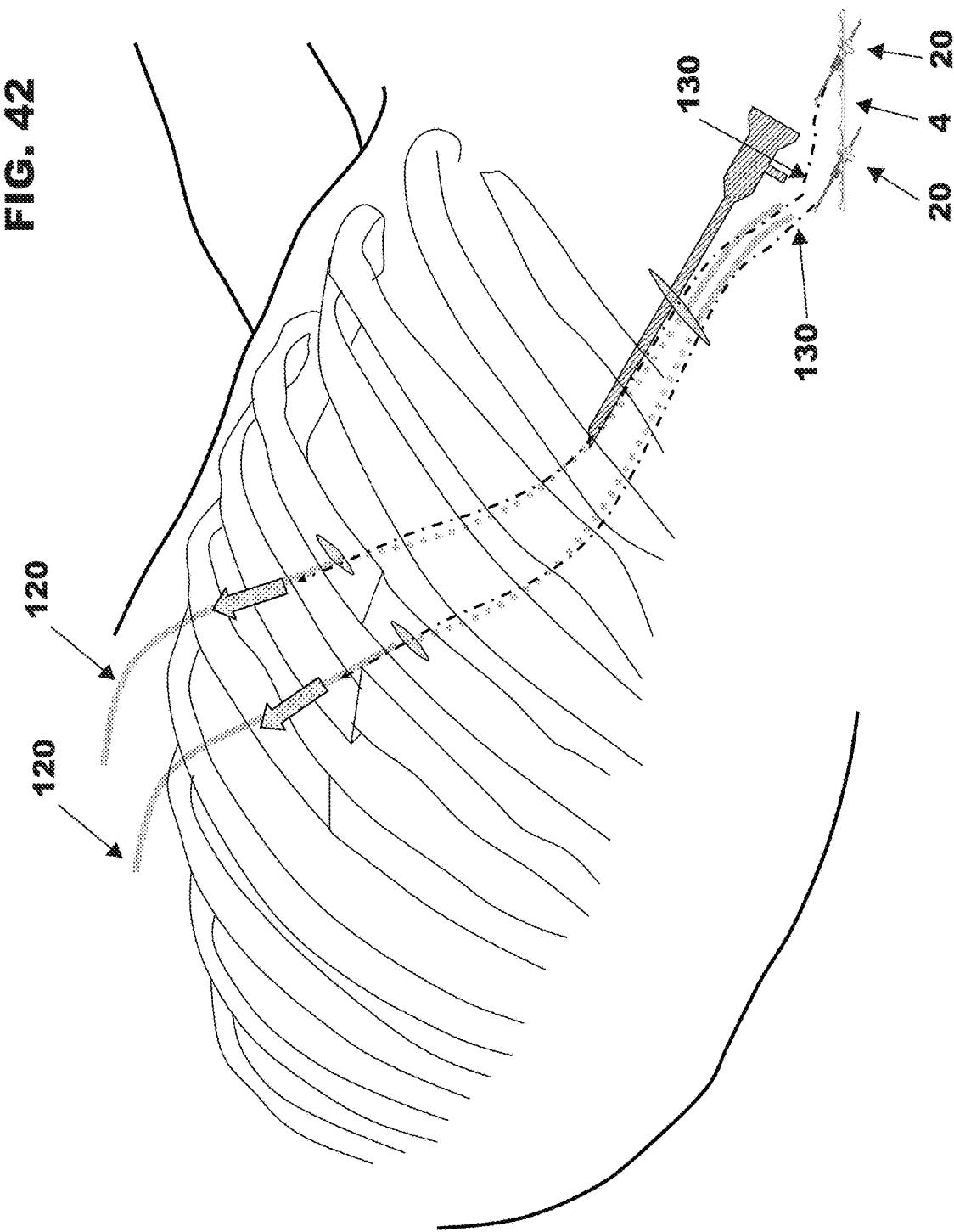
FIG. 42 is an illustration of the ends of the tether being removed from the ends of the guide tubes opposite to the ends in which the tethers were inserted in accordance with an aspect of an illustrative embodiment.
Figure 43:
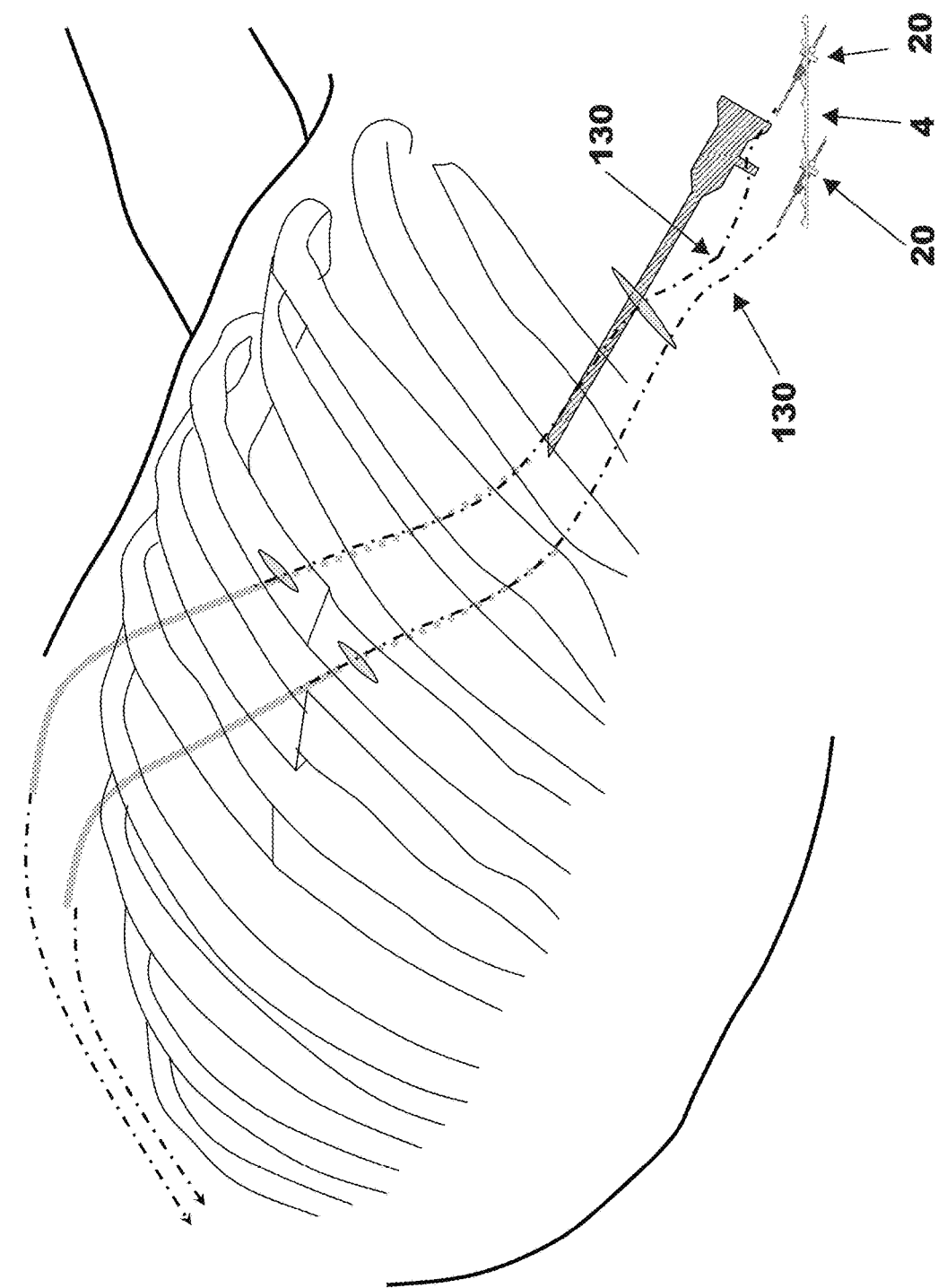
FIG. 43 is an illustration showing the tethers remaining in the patient's body after the guide tubes have been removed in accordance with an aspect of an illustrative embodiment.

FIG. 40 shows guide tubes 120 inserted into the patient's body after removal of the positioning forceps 40. FIG. 41 shows tethers 130 being inserted into one end of the guide tubes 120. The tethers have been passed through pivoting locking posts 20. Pivoting locking posts 20 have been engaged in longitudinal member 4. In FIG. 42, are tethers 130 are shown passing through guide tubes 120 so that they are now outside each end of guide tube 120. In FIG. 43, guide tubes 120 are removed from the body while leaving tethers 130 in the body. Tethers 130 are most preferably made of stainless steel but could also be made of titanium or cobalt chrome. Tethers 130 preferably have as their dimensions 0.1 to 5 mm in diameter (if they round), and most preferably 0.9 mm. The length of the tether is preferably 1000 mm. It should be understood that a "tether" may include a cable or wire or flexible rod including a rod made of plastic or metal.

Figure 44:
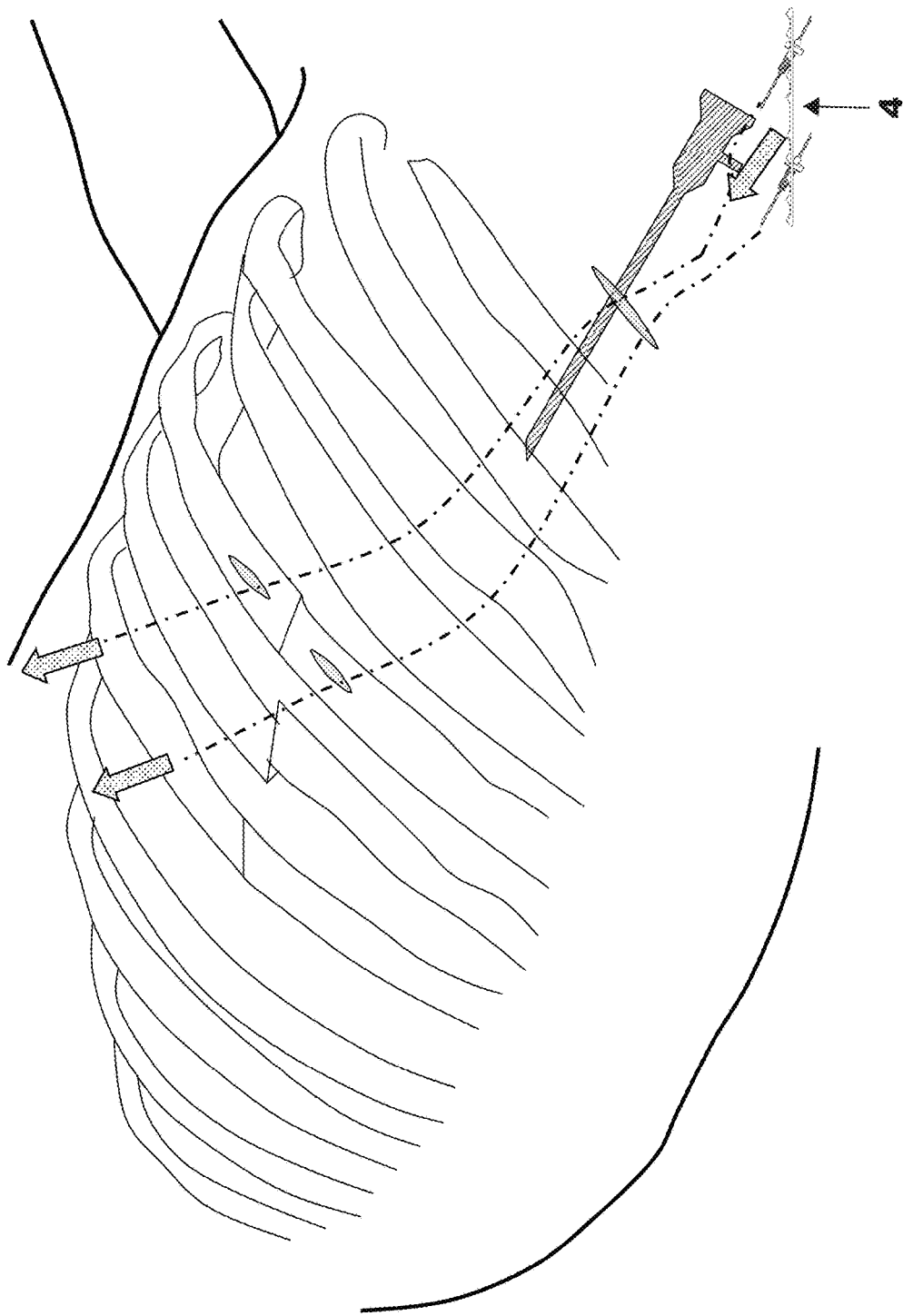
FIG. 44 is an illustration showing the longitudinal member being pulled into the patient's body.
Figure 45:
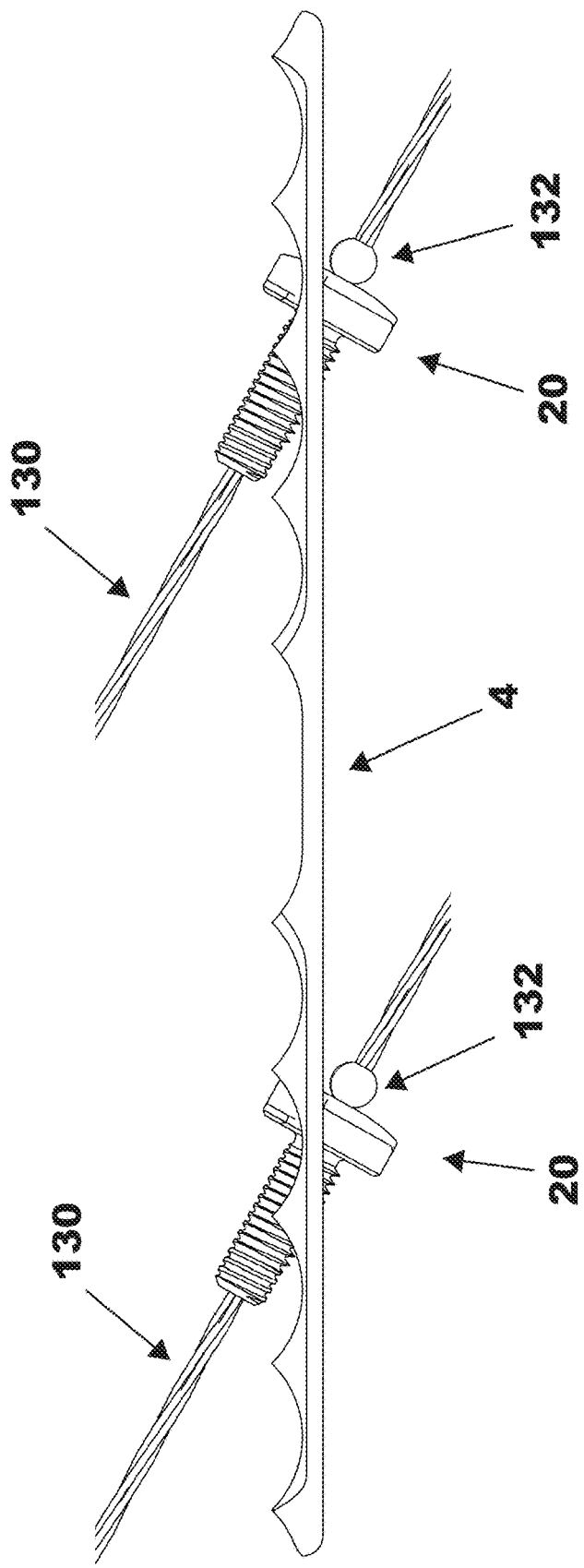
FIG. 45 is a close up view of the longitudinal member with the pivoting locking posts collapsed in the member in accordance with an aspect of an illustrative embodiment.

In FIG. 44, longitudinal member 4 is pulled into the body using tethers 130. FIG. 45 shows a preferred embodiment of the arrangement of the longitudinal member as it is pulled into the patient's body. Specifically, pivoting locking posts 20 are collapsed into longitudinal member 4 so as to facilitate passage of the longitudinal member through the body to the bone segments to be repaired. Tether 130 passes through a longitudinal cavity in pivoting locking post 20. Ball 132 is attached to tether 130 and pulls the pivoting locking post 20 and longitudinal member 4 into the body. The locking posts can pivot between a collapsed position and an extended position. Pivoting locking posts 20 are engaged into longitudinal member 4 by inserting insertion tab 22 into slot 14. When pivoting locking posts 20 are moved away from slot 14, they are effectively fixed into longitudinal member 4.

Figure 46:
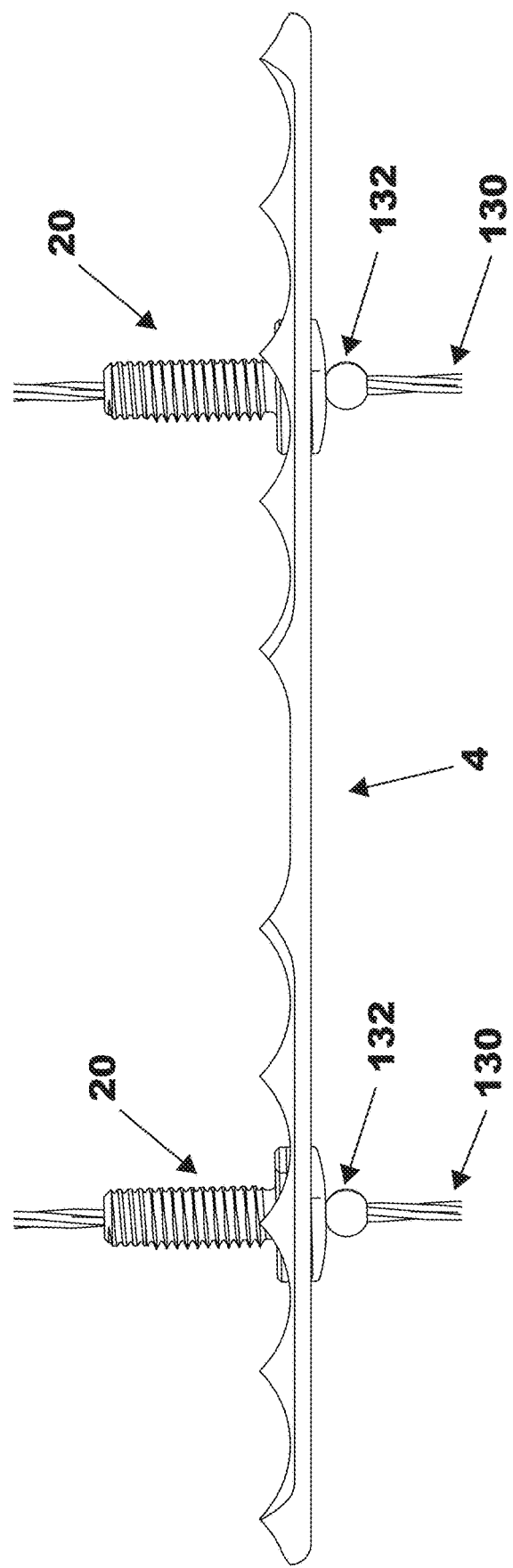
FIG. 46 is a close up view of the longitudinal member with the pivoting locking posts in an upright position in accordance with an aspect of an illustrative embodiment.
Figure 47:
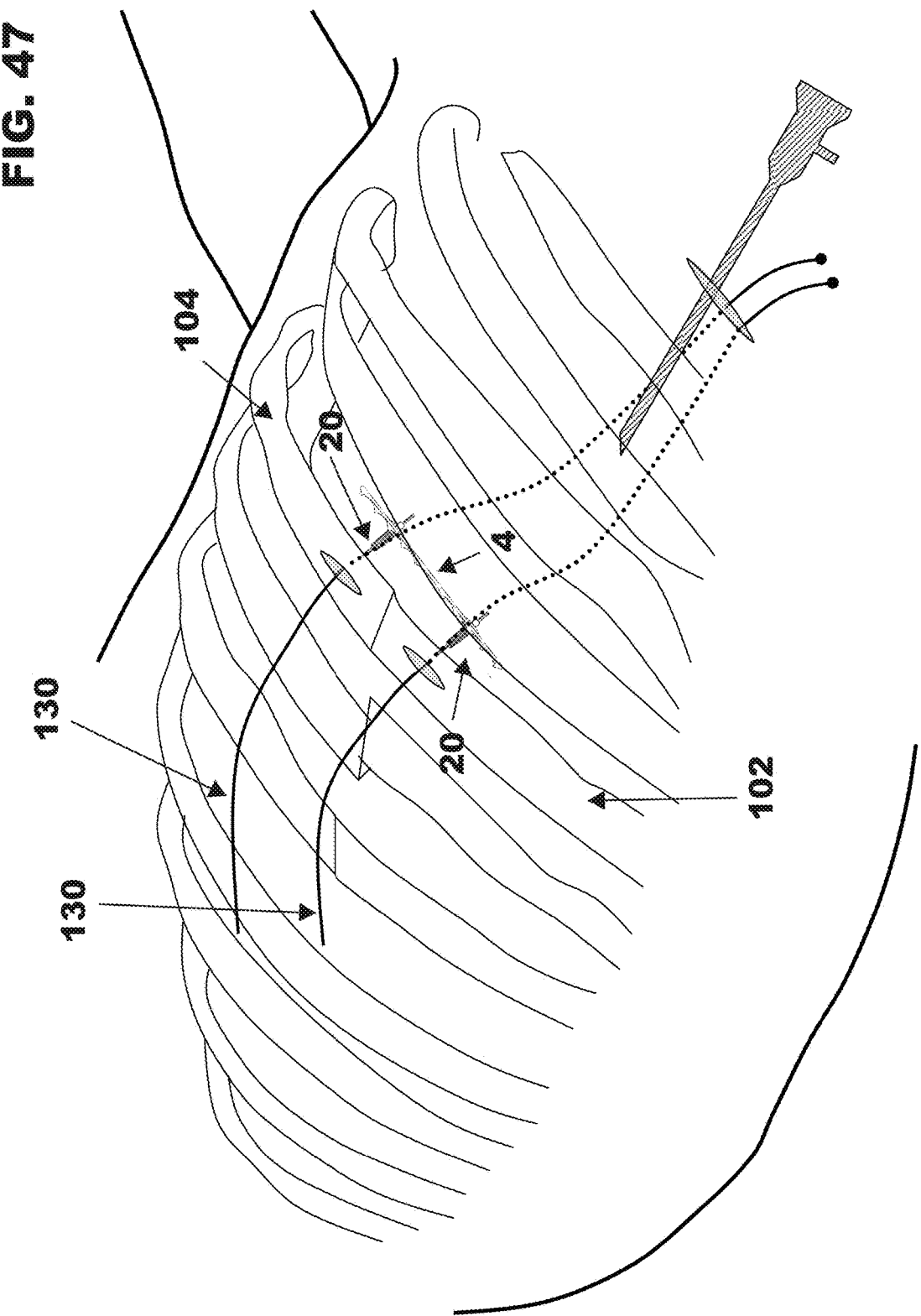
FIG. 47 is an illustration of the longitudinal member about to be inserted into holes in the patient's ribs in accordance with an aspect of an illustrative embodiment.

In FIG. 46, a preferred arrangement for the longitudinal member 4 and pivoting locking posts 20 is shown just prior to its insertion into the holes 118 in the bone segments. This embodiment permits the pivoting locking posts 20 to pivot into a position generally perpendicular to longitudinal member 4 just prior to insertion into holes in the bone segment. FIG. 47 shows the assembly of FIG. 46 about to be inserted into the holes 118 in bone segments 102 and 104

Figure 48:
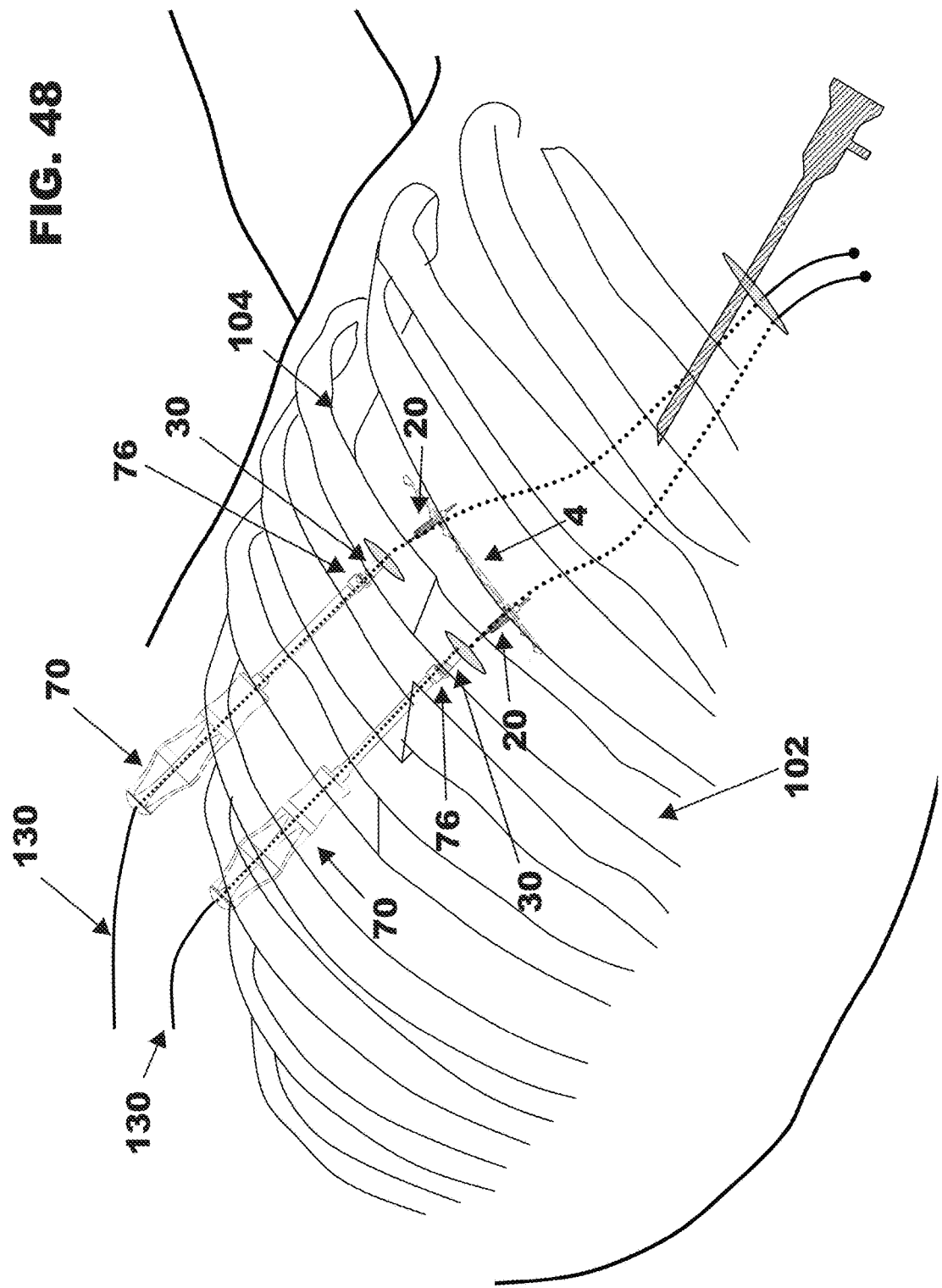
FIG. 48 is an illustration of an external drive tool with the tethers inserted in a longitudinal cavity in the hex drive in accordance with an aspect of an illustrative embodiment.
Figure 49:
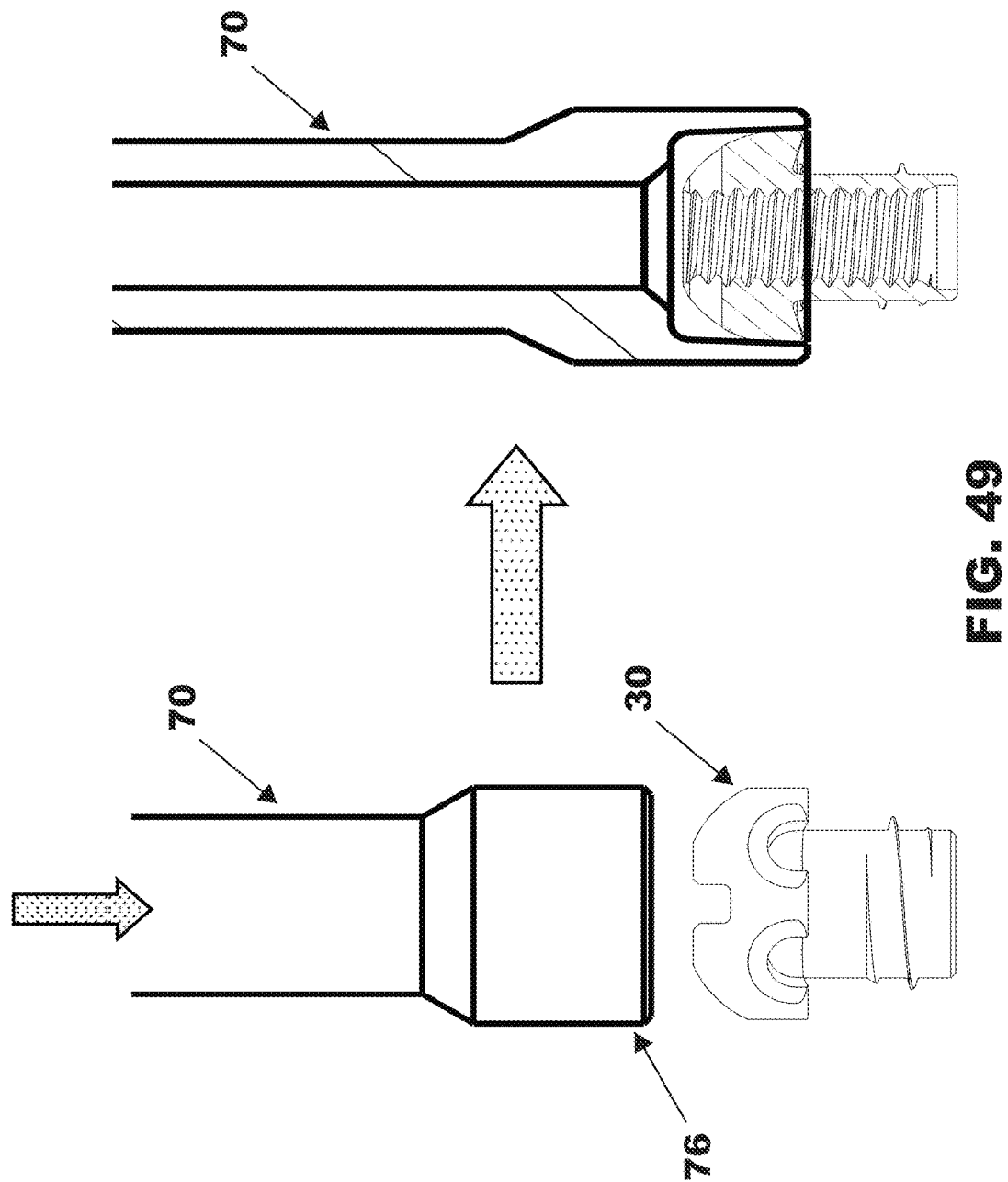
FIG. 49 is an illustration of an external drive tool engaging a locking cap in the bone repair system in an aspect of an illustrative embodiment.
Figure 50:
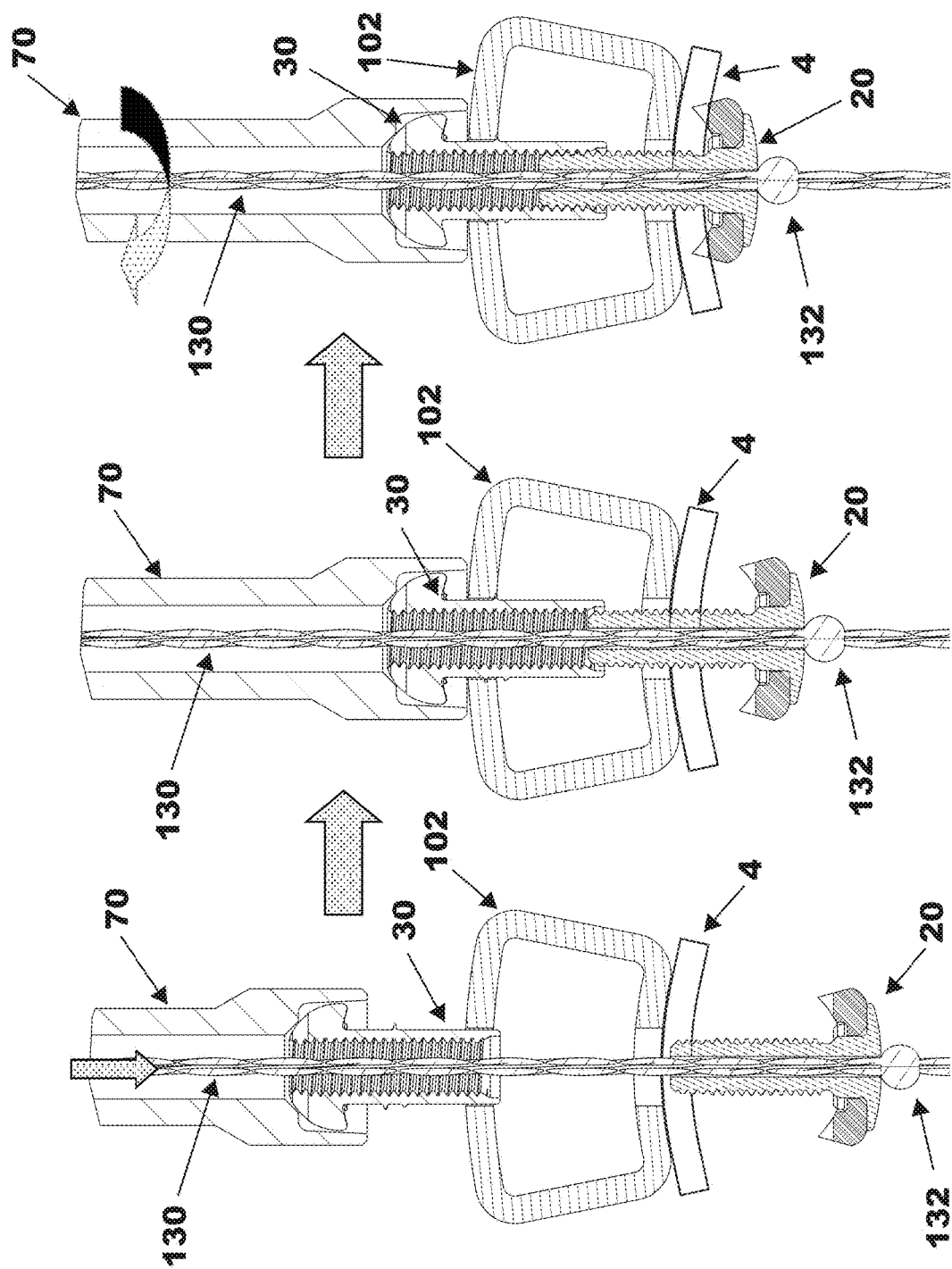
FIGS. 50 A, B, and C show the locking cap and the pivoting locking post in varying degrees of engagement in accordance with an aspect of an illustrative embodiment.

In FIG. 48, an external drive tool 70 has locking cap inserted in end 76. Tether 130 is passed through this assembly to facilitate passage of locking cap 30 to bone segments 102 and 104 where it will receive pivoting locking post 20. FIG. 49 further illustrates the process of inserting locking cap 30 into external drive tool 70.

Figure 51:
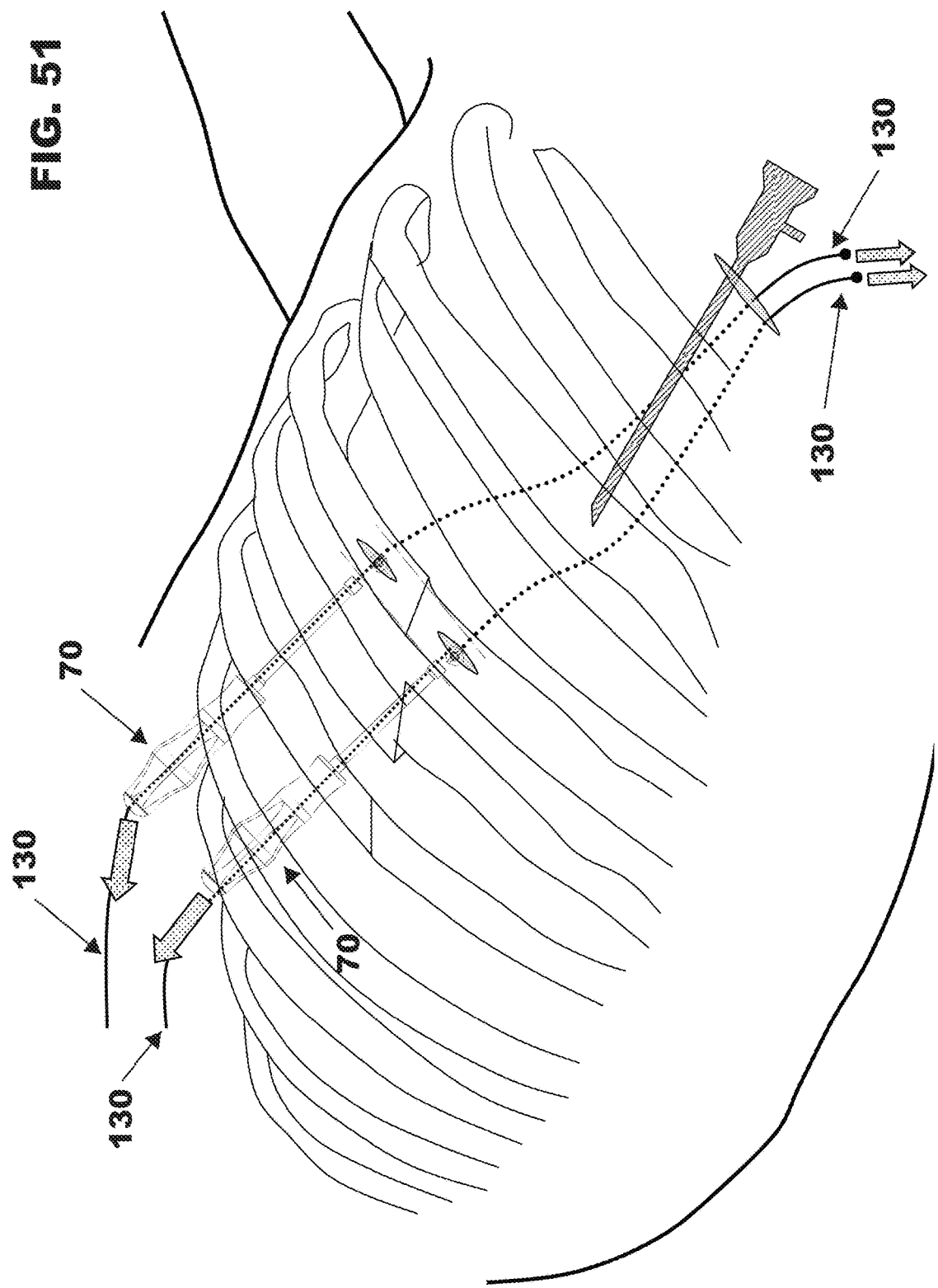
FIG. 51 shows an illustration of the external drive tool being removed from the body in accordance with an aspect of an illustrative embodiment.

FIGS. 50A, 50B, and 50C show the process of tightening pivoting locking post 20 and locking cap 30. In FIG. 51, removal of external drive tool 70 is shown along tethers 130. After external drive tool 70 is removed from the body, guide wires 130 are removed from the body.

Figure 52:
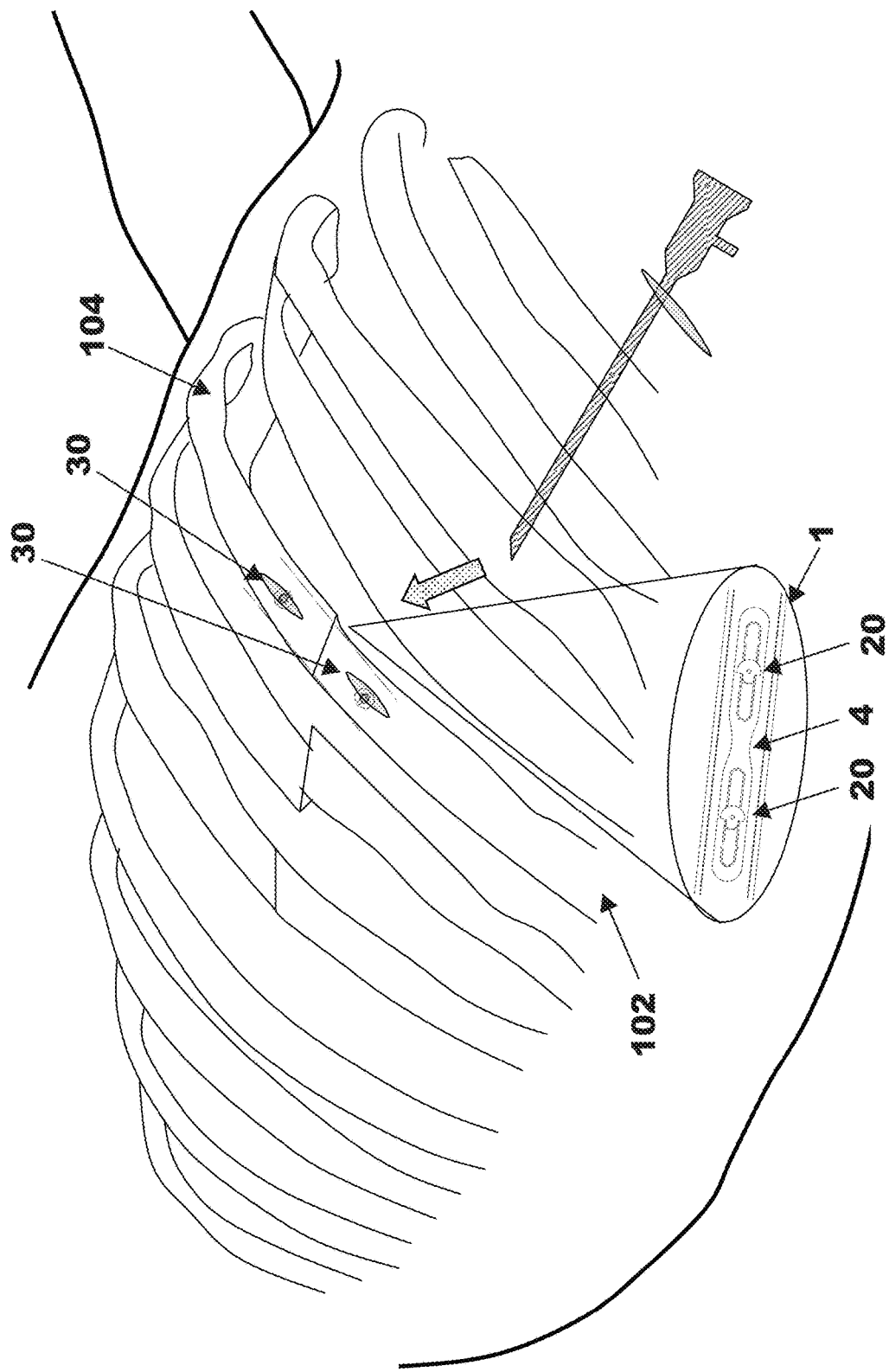
FIG. 52 shows the patient's broken ribs joined by the bone repair system in an aspect of an illustrative embodiment in accordance with an aspect of an illustrative embodiment.

FIG. 52 shows bone segments 102 and 104 joined using the bone repair system 1 in an aspect of an illustrative embodiment.

Figure 53:
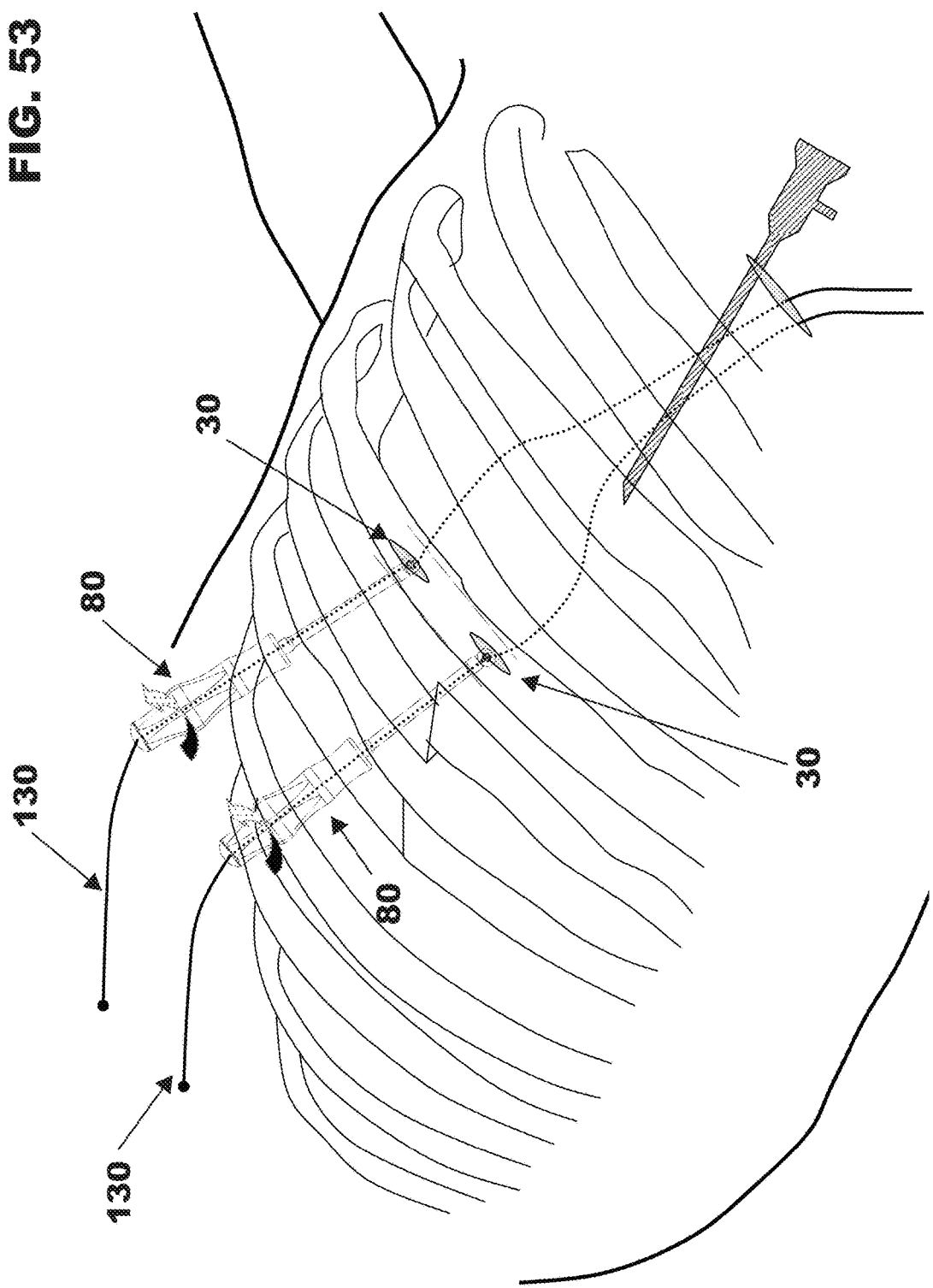
FIG. 53 shows a removal driver being inserted over tethers prior to removal of the bone repair system in an aspect of an illustrative embodiment in accordance with an aspect of an illustrative embodiment.

The bone repair system is removable in an aspect of an illustrative embodiment. FIG. 53 provides a high level overview of the process. Removal driver 80 is inserted along tethers 130 to engage locking cap 30. After engagement, locking cap 30 can be removed from pivoting locking post 20 (not shown) and the bone repair system can be removed from the body in a conventional manner. Removal driver is most preferably made of the same materials external drive tool 70.

Any or all of the components described herein for completing the bone repair in accordance with an aspect of the illustrative embodiments can be assembled for ease of use as a surgical kit. A tray can be provided where the components can be conveniently and securely positioned for ease of access and use during a surgery.

The system and method described herein allow for the rapid fixation of broken rib segments with less blood loss, and reduced post-operative pain and discomfort for the patient. Disruption of the surrounding musculature, soft tissue, cartilage, periosteum and neural structures could be significantly reduced when compared to conventional surgical techniques. This differs from some existing techniques which can be quite lengthy, utilize a wide exposure, use large muscle dissection and often have a complicated recovery.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for the percutaneous repair of a first bone segment and a second bone segment of a fractured bone having a drill hole in each bone segment in a patient comprising:
    a longitudinal member configured to contact the first bone segment and the second bone segment and having at least one opening and cleats on a bottom side of the longitudinal member adapted to contact the first bone segment and the second bone segment;
    a first fastener assembly configured to be disposed through the at least one opening of the longitudinal member to hold the longitudinal member in place through the opening and the hole in the first bone segment, the first fastener assembly including a first inner fastener and a first outer fastener, wherein the first inner fastener is a pivoting locking post having a shaft and a head flange integrally formed with the shaft, the head flange having an insertion tab; and
    a second fastener assembly configured to be disposed through the at least one opening of the longitudinal member to hold the longitudinal member in place through the opening and the hole in the second bone segment, the second fastener assembly including a second inner fastener and a second outer fastener, wherein the second inner fastener is a pivoting locking post having a shaft and a head flange integrally formed with the shaft, the head flange having an insertion tab;
    wherein the longitudinal member has slots in each opening adapted to receive a respective insertion tab to engage the pivoting locking posts into the longitudinal member, and wherein each pivoting locking post can pivot between a collapsed position with its head flange rotated below the bottom side of the longitudinal member and an extended position such that its shaft moves while its head flange remains fixed in position along the longitudinal member.

2. The system of claim 1, wherein the longitudinal member contains a first opening and a second opening and the first fastener assembly is configured to be disposed through the first opening of the longitudinal member to hold the longitudinal member in place through the first opening and the hole in the first bone segment; and
    wherein the second fastener assembly is configured to be disposed through the second opening of the longitudinal member to hold the longitudinal member in place through the second opening and the hole in the second bone segment.

3. The system of claim 1, wherein the first outer fastener is a locking cap and the second outer fastener is a locking cap.

4. The system of claim 3, wherein the first and second outer fasteners are shaped so as to be turnable by an external drive.

5. The system of claim 3, wherein either the locking caps or the pivoting locking posts have lobed locking threads.

6. The system of claim 3, wherein the locking caps have cutouts spaced around the cap so as to grip and dig into the outer cortex of a bone segment when contacted against a bone segment and wherein the cutouts are of sufficient depth to restrain the caps from being overtightened.

7. The system of claim 3, wherein a portion of each of the locking caps is rounded in shape and has at least one external drive feature.

8. A kit for surgical repair of a fractured bone involving a first bone segment and a second bone segment, comprising:
    a first tether and a second tether each having a proximal end and a distal end configured to be inserted into a first guide tube and a second guide tube respectively;
    a longitudinal member having at least one opening configured to receive a first fastener assembly and a second fastener assembly wherein the longitudinal member is configured to be in contact with the first and second bone segments and has cleats on a bottom side of the longitudinal member configured to be in contact with the first and second bone segments;

a first fastener assembly having a longitudinal channel configured for passing the first tether therethrough and further configured to hold the longitudinal member against the first bone segment, the first fastener assembly including a first inner fastener and a first outer fastener, wherein the first inner fastener is a pivoting locking post having a shaft and a head flange integrally formed with the shaft, the head flange having an insertion tab; and a second fastener assembly having a longitudinal channel configured for passing the second tether therethrough and further configured to hold the longitudinal member against the second bone segment, the second fastener assembly including a second inner fastener and a second outer fastener, wherein the second inner fastener is a pivoting locking post having a shaft and a head flange integrally formed with the shaft, the head flange having an insertion tab;

wherein the longitudinal member has slots in each opening adapted to receive a respective insertion tab to engage the pivoting locking posts into the longitudinal member, and wherein each pivoting locking post can pivot between a collapsed position with its head flange rotated below the bottom side of the longitudinal member and an extended position such that its shaft moves while its head flange remains fixed in position along the longitudinal member.

9. The kit of claim 8, wherein the longitudinal member has a first opening configured to receive the first fastener assembly and a second opening configured to receive the second fastener assembly.

10. The kit of claim 8, further comprising a first guide tube and a second guide tube.

11. The kit of claim 8, further comprising an incision template.

12. The kit of claim 8, further comprising a positioning forceps configured to engage a bone segment and a drill guide configured to be received through the positioning forceps for facilitating drilling a hole in a bone segment.

13. The kit of claim 8, further comprising a drive tool having a longitudinal channel configured to pass a tether therethrough.

14. The kit of claim 8, wherein the kit contains a plurality of outer fasteners configured to fit in bone segments of various thicknesses.

15. The kit of claim 8, wherein the first outer fastener is a locking cap and the second outer fastener is a locking cap.

16. The kit of claim 8, further comprising a removal driver.

17. The kit of claim 8, further comprising packaging containing the kit components.

18. The kit of claim 8, further comprising packaging containing the longitudinal member, the first tether, the second tether, the first fastener assembly, and the second fastener assembly and wherein the longitudinal member, the first tether, the second tether, the first fastener assembly and the second fastener assembly have been sterilized.

* * * * *